(12) United States Patent
Butuner

(10) Patent No.: US 9,949,942 B2
(45) Date of Patent: *Apr. 24, 2018

(54) SUSTAINED RELEASE DELIVERY OF ACTIVE AGENTS TO TREAT GLAUCOMA AND OCULAR HYPERTENSION

(75) Inventor: Zuhal Butuner, Oakville (CA)

(73) Assignee: Mati Therapeutics Inc., Austin, TX (US)

( * ) Notice: Subject to any disclaimer, the term of this patent is extended or adjusted under 35 U.S.C. 154(b) by 216 days.

This patent is subject to a terminal disclaimer.

(21) Appl. No.: 12/463,279

(22) Filed: May 8, 2009

(65) Prior Publication Data

US 2009/0280158 A1 Nov. 12, 2009

Related U.S. Application Data

(60) Provisional application No. 61/052,068, filed on May 9, 2008, provisional application No. 61/052,113, filed on May 9, 208, provisional application No. 61/108,777, filed on Oct. 27, 2008.

(51) Int. Cl.
*A61K 31/216* (2006.01)
*A61F 9/00* (2006.01)
*A61F 9/007* (2006.01)
*A61K 9/00* (2006.01)
*A61K 31/5575* (2006.01)

(52) U.S. Cl.
CPC .......... *A61K 31/216* (2013.01); *A61F 9/0017* (2013.01); *A61F 9/00781* (2013.01); *A61K 9/0051* (2013.01); *A61K 31/5575* (2013.01)

(58) Field of Classification Search
None
See application file for complete search history.

(56) References Cited

U.S. PATENT DOCUMENTS

| 3,865,108 A | 2/1975 | Hartop |
| 3,949,750 A | 4/1976 | Freeman |
| 4,014,335 A | 3/1977 | Arnold |

(Continued)

FOREIGN PATENT DOCUMENTS

| AU | 20023644336 | 7/2003 |
| EP | 0442745 A1 | 8/1991 |

(Continued)

OTHER PUBLICATIONS

"U.S. Appl. No. 10/825,047, Response filed Apr. 22, 2009 to Non Final Office Action dated Oct. 22, 2008", 17 pgs.

(Continued)

*Primary Examiner* — Patricia Duffy
*Assistant Examiner* — Garen Gotfredson
(74) *Attorney, Agent, or Firm* — Koren Anderson; Mati Therapeutics Inc.

(57) ABSTRACT

The methods described herein provide treatment of glaucoma, ocular hypertension, and elevated intraocular pressure with latanoprost or other therapeutic agent(s). Implant devices for insertion into a punctum of a patient provide sustained release of latanoprost or other therapeutic agent(s) that is maintained for 7, 14, 21, 30, 45, 60, or 90 days or more, thus avoiding patient noncompliance and reducing or lowering adverse events associated with eye drop administration of latanoprost or other therapeutic agent(s) and other therapeutic agent(s).

18 Claims, 18 Drawing Sheets

(56) References Cited

U.S. PATENT DOCUMENTS

| | | |
|---|---|---|
| 4,281,654 A | 8/1981 | Shell et al. |
| 4,660,546 A | 4/1987 | Herrick et al. |
| 4,886,488 A | 12/1989 | White |
| 4,915,684 A | 4/1990 | MacKeen et al. |
| 4,959,048 A | 9/1990 | Seder et al. |
| 5,041,081 A | 8/1991 | Odrich |
| 5,049,142 A | 9/1991 | Herrick et al. |
| 5,053,030 A | 10/1991 | Herrick et al. |
| 5,098,443 A | 3/1992 | Parel et al. |
| 5,128,058 A | 7/1992 | Ishii et al. |
| 5,133,159 A | 7/1992 | Nelson |
| 5,163,959 A | 11/1992 | Herrick |
| 5,171,270 A | 12/1992 | Herrick |
| 5,283,063 A | 2/1994 | Freeman |
| 5,318,513 A | 6/1994 | Leib |
| 5,334,137 A | 8/1994 | Freeman |
| 5,395,618 A | 3/1995 | Darougar et al. |
| 5,417,651 A | 5/1995 | Guena et al. |
| 5,423,777 A | 6/1995 | Tajiri et al. |
| 5,466,233 A | 11/1995 | Weiner et al. |
| 5,556,633 A | 9/1996 | Haddad et al. |
| 5,707,643 A | 1/1998 | Ogura et al. |
| 5,723,005 A | 3/1998 | Herick |
| 5,766,243 A | 6/1998 | Christensen et al. |
| 5,770,589 A | 6/1998 | Billson et al. |
| 5,773,019 A | 6/1998 | Ashton et al. |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano et al. |
| 5,961,370 A | 10/1999 | Valle et al. |
| 5,962,383 A | 10/1999 | Doyel et al. |
| 5,993,407 A | 11/1999 | Moazed |
| 6,010,391 A | 1/2000 | Lewellen et al. |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson et al. |
| 6,149,684 A | 11/2000 | Herrick |
| 6,196,993 B1 | 3/2001 | Cohan et al. |
| 6,234,175 B1 | 5/2001 | Zhou et al. |
| 6,238,363 B1 | 5/2001 | Kurihashi |
| 6,254,562 B1 | 7/2001 | Fouere |
| 6,264,971 B1 | 7/2001 | Darougar et al. |
| 6,290,684 B1 | 9/2001 | Herrick |
| 6,306,114 B1 | 10/2001 | Freeman et al. |
| 6,331,313 B1 | 12/2001 | Wong et al. |
| 6,371,122 B1 | 4/2002 | Mandelkorn |
| 6,375,972 B1 | 4/2002 | Guo et al. |
| 6,383,192 B1 | 5/2002 | Kurihashi |
| 6,428,502 B1 | 8/2002 | Lang |
| 6,455,062 B1 | 9/2002 | Olejnik et al. |
| 6,605,108 B2 | 8/2003 | Mendius et al. |
| 6,629,533 B1 | 10/2003 | Webb et al. |
| 6,706,275 B1 | 3/2004 | Camp |
| 6,729,939 B2 | 5/2004 | Wrue |
| 6,756,049 B2 | 6/2004 | Brubaker et al. |
| 6,780,164 B2 | 8/2004 | Bergheim et al. |
| 6,840,931 B2 | 1/2005 | Peterson et al. |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker et al. |
| 6,994,684 B2 | 2/2006 | Murray et al. |
| 7,017,580 B2 | 3/2006 | Prescott et al. |
| 7,117,870 B2 | 10/2006 | Prescott |
| 7,135,009 B2 | 11/2006 | Tu et al. |
| 7,204,253 B2 | 4/2007 | Mendius et al. |
| 7,204,995 B2 | 4/2007 | El-Sherif et al. |
| 8,702,643 B2 * | 4/2014 | Rapacki .............. A61F 9/0017 424/427 |
| 2002/0032400 A1 | 3/2002 | Moazed |
| 2002/0055701 A1 | 5/2002 | Fischell et al. |
| 2002/0151960 A1 | 10/2002 | Mendius et al. |
| 2002/0198453 A1 | 12/2002 | Herrick, II |
| 2003/0130612 A1 | 7/2003 | Moazed |
| 2004/0102729 A1 | 5/2004 | Haffner et al. |
| 2004/0121014 A1 | 6/2004 | Guo et al. |
| 2004/0127843 A1 | 7/2004 | Tu et al. |
| 2004/0137068 A1 | 7/2004 | Bhushan |
| 2004/0141151 A1 | 7/2004 | Gillespie |
| 2004/0147870 A1 | 7/2004 | Burns |
| 2004/0170685 A1 | 9/2004 | Carpenter et al. |
| 2004/0175410 A1 | 9/2004 | Ashton et al. |
| 2004/0210182 A1 | 10/2004 | Fouere et al. |
| 2004/0249333 A1 | 12/2004 | Bergheim et al. |
| 2004/0265356 A1 | 12/2004 | Mosack |
| 2005/0048121 A1 | 3/2005 | East et al. |
| 2005/0095269 A1 | 5/2005 | Ainpour et al. |
| 2005/0107734 A1 * | 5/2005 | Coroneo .............. 604/9 |
| 2005/0129731 A1 | 6/2005 | Horres et al. |
| 2005/0197614 A1 | 9/2005 | Pritchard et al. |
| 2005/0220882 A1 | 10/2005 | Pritchard et al. |
| 2005/0232972 A1 | 10/2005 | Odrich et al. |
| 2005/0244469 A1 | 11/2005 | Whitcup et al. |
| 2005/0266047 A1 | 12/2005 | Tu et al. |
| 2005/0271704 A1 | 12/2005 | Tu et al. |
| 2005/0283109 A1 | 12/2005 | Peyman |
| 2006/0013835 A1 | 1/2006 | Anderson et al. |
| 2006/0020248 A1 | 1/2006 | Prescott |
| 2006/0020253 A1 | 1/2006 | Prescott |
| 2006/0074370 A1 | 4/2006 | Zhou |
| 2006/0100700 A1 | 5/2006 | Bernard et al. |
| 2006/0106352 A1 | 5/2006 | Kurihashi |
| 2006/0122553 A1 | 6/2006 | Hanna |
| 2007/0083146 A1 | 4/2007 | Murray |
| 2007/0123924 A1 | 5/2007 | Becker |
| 2007/0132125 A1 | 6/2007 | Rastogi et al. |
| 2007/0135914 A1 | 6/2007 | Herrick, II |
| 2007/0243230 A1 | 10/2007 | de Juan et al. |
| 2007/0269487 A1 | 11/2007 | de Juan et al. |
| 2007/0298075 A1 | 12/2007 | Borgia et al. |
| 2007/0299515 A1 | 12/2007 | Herrick, II |
| 2007/0299516 A1 | 12/2007 | Cui |
| 2008/0038317 A1 | 2/2008 | Chang et al. |
| 2008/0045878 A1 | 2/2008 | Bergheim et al. |
| 2008/0045911 A1 | 2/2008 | Borgia et al. |
| 2009/0092654 A1 | 4/2009 | Juan, Jr. et al. |
| 2009/0104243 A1 | 4/2009 | Utkhede et al. |
| 2009/0104248 A1 | 4/2009 | Rapacki et al. |
| 2009/0105749 A1 | 4/2009 | De Juan et al. |
| 2009/0118702 A1 | 5/2009 | Lazar |

FOREIGN PATENT DOCUMENTS

| | | |
|---|---|---|
| EP | 0621022 A1 | 10/1994 |
| JP | 10-33584 | 2/1998 |
| JP | 2004-202276 | 7/2004 |
| JP | 2005-000628 | 1/2005 |
| JP | 2005-058622 | 3/2005 |
| JP | 2005-110765 | 4/2005 |
| JP | 2005-110930 | 4/2005 |
| JP | 2005-312835 | 11/2005 |
| JP | 2005-319190 | 11/2005 |
| JP | 2005-328922 | 12/2005 |
| JP | 2007-195819 | 8/2007 |
| WO | WO 98/33461 A1 | 8/1998 |
| WO | WO-98/42282 A1 | 10/1998 |
| WO | WO-99/37260 A1 | 7/1999 |
| WO | WO-99/44553 A1 | 9/1999 |
| WO | WO-99/64089 A1 | 12/1999 |
| WO | WO-99/65544 A1 | 12/1999 |
| WO | WO-00/27321 A1 | 5/2000 |
| WO | WO-00/62760 A1 | 10/2000 |
| WO | WO-02/11783 A1 | 2/2002 |
| WO | WO-02/058667 A2 | 8/2002 |
| WO | WO-02/083198 A2 | 10/2002 |
| WO | WO 02/089767 | 11/2002 |
| WO | WO 03/017897 A2 | 3/2003 |
| WO | WO-03/022242 A1 | 3/2003 |
| WO | WO 03/057101 A1 | 7/2003 |
| WO | WO 2004/004614 A2 | 1/2004 |

(56) References Cited

FOREIGN PATENT DOCUMENTS

| WO | WO 2004/024043 A2 | 3/2004 |
|---|---|---|
| WO | WO 2004/105658 A1 | 12/2004 |
| WO | WO-2004/112639 A2 | 12/2004 |
| WO | WO-2005/000154 A2 | 1/2005 |
| WO | WO-2005/086694 A2 | 9/2005 |
| WO | WO-2006/014434 A2 | 2/2006 |
| WO | WO-2006/031658 A2 | 3/2006 |
| WO | WO-2006/044669 A2 | 4/2006 |
| WO | WO-2006/057859 A1 | 6/2006 |
| WO | WO-2006/096586 A1 | 9/2006 |
| WO | WO-2007/008262 A2 | 1/2007 |
| WO | WO-2007/115259 A2 | 10/2007 |
| WO | WO-2007/115261 A2 | 10/2007 |
| WO | WO-2007/149771 A2 | 12/2007 |
| WO | WO-2007/149832 A2 | 12/2007 |
| WO | WO 2008/056060 A2 | 5/2008 |
| WO | WO-2008/094989 A2 | 8/2008 |
| WO | WO-2009/035562 A2 | 3/2009 |
| WO | WO 2010/008883 | 1/2010 |

OTHER PUBLICATIONS

"U.S. Appl. No. 10/825,047, Preliminary Amendment and Response filed Aug. 18, 2008 to Restriction Requirement dated Jul. 17, 2008", 10 pgs.
"U.S. Appl. No. 10/825,047, Final Office Action dated Jun. 9, 2009", 14 pgs.
"U.S. Appl. No. 10/825,047, Non-Final Office Action dated Oct. 22, 2008", 13 pgs.
"U.S. Appl. No. 11/695,537, Notice dated Nov. 28, 2008 Regarding a Noncompliant or Nonresponsive Amendment filed on Nov. 3, 2008", 3 pgs.
"U.S. Appl. No. 11/695,537, Restriction Requirement dated Oct. 3, 2008", 10 pgs.
"U.S. Appl. No. 11/695,537, Amendment and Response filed Nov. 3, 2008 to Restriction Requirement dated Oct. 3, 2008", 15 pgs.
"U.S. Appl. No. 11/695,537, Response filed Dec. 17, 2008 to Office Communication dated Nov. 28, 2008", 8 pgs.
"U.S. Appl. No. 11/695,545, Preliminary Amendment and Response filed Nov. 6, 2008 to Restriction Requirement dated Oct. 6, 2008", 14 pgs.
"U.S. Appl. No. 11/695,545, Restriction Requirement dated Oct. 6, 2008", 10 pgs.
"Chinese Application No. 200580028979.2, First Office Action dated Dec. 12, 2008", 7 pgs.

"European Application Serial No. 05768122.3 , Office Action dated Mar. 31, 2009", 3 pgs.
"International Application Serial No. PCT/US07/65792, International Search Report dated Nov. 20, 2008", 2 pgs.
"International Application Serial No. PCT/US07/65792, International Written Opinion dated Nov. 20, 2008", 5 pgs.
"International Application Serial No. PCT/US2007/065789, International Search Report dated Aug. 13, 2008", 3 pgs.
"International Application Serial No. PCT/US2007/065789, Written Opinion dated Aug. 13, 2008", 5 pgs.
"International Application Serial No. PCT/US2008/010479, International Search Report dated Dec. 15, 2008", 6 pgs.
"International Application Serial No. PCT/US2008/010479, Written Opinion dated Dec. 15, 2008", 7 pgs.
"International Application Serial No. PCT/US2008/010487, International Search Report dated May 25, 2009", 5 pgs.
"International Application Serial No. PCT/US2008/010487, Written Opinion dated May 25, 2009", 8 pgs.
"Israel Application No. 194515, Office Action dated Apr. 5, 2009", 1 pg.
De Juan, Jr., E., et al., "Expandable Nasolacrimal Drainage System Implants", U.S. Appl. No. 60/970,696, filed Sep. 7, 2007, 82 pgs.
De Juan, Jr., E., et al., "Manufacture of Expandable Nasolacrimal Drainage System Implants", U.S. Appl. No. 60/970,720, filed Sep. 7, 2007, 57 pgs.
De Juan, Jr., E., et al., "Multiple Drug Delivery Systems and Combinations of Drugs With Punctal Implants", U.S. Appl. No. 60/970,820, filed Sep. 7, 2007, 67 pgs.
Lazar, E., "Treatent Medium Delivery Device and Methods for Delivery of Such Treatment Mediums To The Eye Using Such A Delivery Device", U.S. Appl. No. 11/571 147, filed Dec. 21 2006, 32 pgs.
Reich, C., et al., "Nasolacriminal Drainage System Implants for Drug Delivery", U.S. Appl. No. 60/970,709, filed Sep. 7, 2007, 103 pgs.
Reich, Jr., Carl J., et al., "Manufacture of Drug Cores for Sustained Release of Therapeutic Agents", U.S. Appl. No. 60/970,699, filed Sep. 7, 2007, 66 pgs.
International Preliminary Report on Patentability as issued for PCT/US2009/002854, dated Nov. 18, 2010.
International Search Report and Written Opinion as issued for PCT/US2009/002854, dated May 3, 2010.
Examination Report, issued by the New Zealand Intellectual Property Office dated Apr. 26, 2012, in related New Zealand Application No. 588938.

* cited by examiner

|  | 3.5 μg | 14 μg | 21 μg |
|---|---|---|---|
| WEEK 4 | N=20<br>-3.9± 2.7 | N=19<br>-3.4± 3.1 | N=21<br>-3.2± 3.3 |
| WEEK 8 | N=17<br>-3.6± 2.4 | N=15<br>-4.2± 3.7 | N=15<br>-4.4± 2.4 |
| WEEK 12 | N=13<br>-5.4± 2.7 | N=12<br>-4.8± 3.2 | N=13<br>-4.9± 2.1 |

ALL MEAN IOP CHANGES FROM BASELINE ARE STATISTICALLY SIGNIFICANT (P<.001)

CORE MEAN IOP CHANGE FROM BASELINE

FIG. 10

| IOP REDUCTION | LATANOPROST (8AM/MEAN DIURNAL) | TIMOLOL (MEAN DIURNAL) | BIMATOPROST (8AM) | CORE (9AM) |
|---|---|---|---|---|
| ≥15% | 72-82% | 67% | 89% | 71% |
| ≥20% | 62-75% | 43% | 79% | 55% |
| ≥25% | 52% | 28% | -- | 37% |

PERCENT IOP REDUCTION: CORE VS. LATANOPROST EYE DROP STUDIES

FIG. 13

| OCULAR ADVERSE EVENTS | N (%) OF PATIENTS | | | |
|---|---|---|---|---|
| | 3.5 μg (N=21) | 14 μg (N=19) | 21 μg (N=21) | ALL DOSES (N=61) |
| LACRIMATION INCREASED | 2 (9.5) | 4 (21.1) | 3 (14.3) | 9 (14.8) |
| OCULAR DISCOMFORT | 2 (9.5) | 3 (15.8) | 1 (4.8) | 6 (9.8) |
| CONJUNCTIVAL HYPEREMIA | 1 (4.8) | 0 | 1 (4.8) | 2 (3.3) |
| DEVICE MIGRATION | 0 | 1 (5.3) | 1 (4.8) | 2 (3.3) |
| FOREIGN BODY SENSATION | 1 (4.8) | 1 (5.3) | 0 | 2 (3.3) |
| GRANULOMA | 0 | 2 (10.5) | 0 | 2 (3.3) |
| EYE ITCHING | 0 | 1 (5.3) | 0 | 1 (1.6) |
| EYELID MARGIN CRUSTING | 0 | 0 | 1 (4.8) | 1 (1.6) |
| OCULAR HYPEREMIA | 1 (4.8) | 0 | 0 | 1 (1.6) |
| PUNCTATE KERATITIS | 0 | 1 (5.3) | 0 | 1 (1.6) |

CORE: ALL OCULAR ADVERSE EVENTS

FIG. 16

| OCULAR ADVERSE EVENTS | % PATIENTS | | |
|---|---|---|---|
| | CORE (3M FOLLOW-UP) (N=61) | LATANOPROST EYE DROP STUDIES (6M FOLLOW-UP) | |
| | | XALATAN PIVOTAL TRIALS* (N=460) | NOECKER ET AL** (N=136) |
| CONJUNCTIVAL HYPEREMIA | 3.3 | 8.0 | 20.6 |
| FOREIGN BODY SENSATION | 3.3 | 13.3 | – |
| PUNCTATE KERATITIS | 1.6 | 7.1*** | – |
| BURNING | 0 | 7.4 | 5.9 |
| STINGING | 0 | 9.3 | – |
| DISCOMFORT | 9.8 | 1.3 | – |
| LACRIMATION INCREASED | 14.8 | 4.1 | – |
| ITCHING | 1.6 | 7.6 | 2.9 |
| BLURRED VISION/VISION ABNORMAL | 0 | 7.6 | – |
| INCREASED PIGMENTATION | 0 | 7.2 | – |

FIG. 17

MAIN OCULAR ADVERSE EVENTS: CORE VS. LATANOPROST EYE DROP STUDIES

| OCULAR AE | CORE (N=61) | TRAVOPROST 0.0015% (N=205) (1) | TRAVOPROST 0.004% (N=200) (1) | TIMOLOL (N=200) (1) | TIMOLOL (N=241) (3) | LATAN. (N=196) (1) | LATAN. (N=136) (2) | BIMAT. (N=133) (2) | BIMAT.QD (N=474) (3) |
|---|---|---|---|---|---|---|---|---|---|
| CONJUNCTIVAL HYPEREMIA | 2 (3.3) | | | | 32 (13.3) | | 28 (20.6) | 59 (44.4) | 212 (44.7) |
| EYE PRURITUS | 1 (1.6) | 8 (3.9) | 15 (7.5) | 4 (2.0) | 8 (3.3) | 12 (6.1) | 4 (2.9) | 13 (9.8) | 69 (14.6) |
| EYELID MARGIN CRUSTING | 1 (1.6) | | | | | | | | |
| FOREIGN BODY SENSATION | 2 (3.3) | 2 (2.4) | 14 (7.0) | 2 (1.0) | 5 (2.1) | 6 (3.1) | | | 26 (5.5) |
| LACRIMATION INCREASED | 9 (14.8) | | | | | | | | |
| OCULAR BURNING | 0 | | | | 25 (10.4) | | 8 (5.9) | 7 (5.3) | 33 (7.0) |
| OCULAR DISCOMFORT | 6 (9.8) | 11 (5.4) | 15 (7.5) | 15 (7.5) | | 5 (2.6) | | | |
| OCULAR HYPEREMIA | 1 (1.6) | 78 (38.0) | 99 (49.5) | 28 (14.0) | | 54 (27.6) | | | |
| PUNCTATE KERATITIS | 1 (1.6) | 5 (2.4) | 7 (3.5) | 5 (2.5) | | 4 (2.0) | | | |
| VA DECREASE | 0 | 12 (5.9) | 17 (8.5) | 19 (9.5) | 11 (4.6) vd | 9 (4.6) | | | 24 (5.1) vd |

CORE OCULAR AEs COMPARED WITH EYE DROPS

FIG. 18

SUSTAINED RELEASE DELIVERY OF ACTIVE AGENTS TO TREAT GLAUCOMA AND OCULAR HYPERTENSION

CLAIM OF PRIORITY

Benefit of priority is hereby claimed to U.S. Provisional Patent Application Ser. No. 61/052,068 filed on May 9, 2008 and entitled Sustained Release Delivery of Latanoprost to Treat Glaucoma; U.S. Provisional Patent Application Ser. No. 61/052,113 filed on May 9, 2008 and entitled Sustained Release Delivery of Latanoprost to Treat Glaucoma; and U.S. Provisional Patent Application Ser. No. 61/108,777 filed on Oct. 27, 2008 and entitled Sustained Release Delivery of Latanoprost to Treat Glaucoma, the specifications of which are herein incorporated by reference in their entirety.

BACKGROUND OF THE INVENTION

Glaucoma is a collection of disorders characterized by progressive visual field loss due to optic nerve damage. It is the leading cause of blindness in the United States, affecting 1-2% of individuals aged 60 and over. Although there are many risk factors associated with the development of glaucoma (age, race, myopia, family history, and injury), elevated intraocular pressure, also known as ocular hypertension, is the only risk factor successfully manipulated and correlated with the reduction of glaucomatous optic neuropathy. Public health figures estimate that 2.5 million Americans manifest ocular hypertension.

In order to treat glaucoma and ocular hypertension, drugs are often required to be administered to the eye. A conventional method of drug delivery is by topical drop application to the eye's surface. Topical eye drops, though effective, can be inefficient. For instance, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can treat the eye. Further, in many cases, topically applied medications have a peak ocular effect within about two hours, after which additional applications of the medications should be performed to maintain the therapeutic benefit. PCT Publication WO 06/014434 (Lazar), which is incorporated herein by reference in its entirety, may be relevant to these or other issues associated with eye drops.

To compound ocular management difficulty, patients often do not use their eye drops as prescribed. Noncompliance rates of at least 25% commonly have been reported. This poor compliance can be due to, for example, an initial stinging or burning sensation caused by the eye drop and experience by a patient. Instilling eye drops in one's own eye can be difficult, in part because of the normal reflex to protect the eye. Therefore, one or more drops may miss the eye. Older patients may have additional problems instilling drops due to arthritis, unsteadiness, and decreased vision. Pediatric and psychiatric populations pose difficulties as well.

In light of the above, what is needed are improved drug delivery systems that overcome at least some of the above shortcomings.

SUMMARY OF THE INVENTION

The present invention provides methods for sustained release delivery of a therapeutic agent from a punctum of a patient into ocular tissues for the treatment of a disease, particularly a disease of the eye, using an implant. In one embodiment, the therapeutic agent is latanoprost. In one aspect, the present invention provides a method of delivering latanoprost and/or one or more other therapeutic agent(s) to an eye having associated tear fluid, the method comprises placing a topical formulation comprising latanoprost and/or one or more other therapeutic agent(s) into a punctum of the eye. In one embodiment, the topical formulation is in a form of a drug core which is optionally disposed in a punctal implant body configured for at least partial insertion into a punctum or canaliculus of the eye. In some embodiments, the drug core can comprise a matrix and inclusions of a therapeutic agent, in some embodiments latanoprost, within the matrix. A portion of the drug core can be exposed to the tear in order to release the latanoprost or other therapeutic agent(s) to the tear. The latanoprost or other therapeutic agent(s) may be dissolved into or dispersed in the matrix and the latanoprost or other therapeutic agent(s) is released through the exposed portion of the core at therapeutic levels over a sustained period. In another aspect, the present invention provides a method of delivering latanoprost or other therapeutic agent(s) to an eye having associated tear fluid, the method comprises placing a topical formulation consisting essentially of latanoprost or other therapeutic agent(s) and a polymer into a punctum of the eye. In one embodiment, the topical formulation is impregnated within a pre-formed punctal implant, or is made in the form of a punctal implant composed of a mixture of latanoprost or other therapeutic agent(s) and a polymer.

In some embodiments, the latanoprost or other therapeutic agent(s) can be released through the exposed portion of the drug core or impregnated body at therapeutic levels for about 90 days. The latanoprost or other therapeutic agent(s) may comprise an oil. The latanoprost or other therapeutic agent(s) can be encapsulated within the matrix, and the matrix may comprise a non-bioabsorbable polymer.

The present invention provides the use of latanoprost or another therapeutic agent or agents for the treatment of elevated intraocular pressure. In some embodiments, the invention provides the use of latanoprost for treatment of glaucoma. In some embodiments, the invention provides the use of a therapeutic agent or agents other than latanoprost for treatment of glaucoma. In some embodiments, the use of latanoprost for reducing intraocular pressure is provided. Certain embodiments provide the use of latanoprost or another therapeutic agent or agents for treating diseases of the eye. In some embodiments, combinations of therapeutic agents are provided for use in treatment of diseases of the eye. The present invention also provides the use of an anti-glaucoma drug for treatment of glaucoma and/or elevated intraocular pressure. In some embodiments, the present invention provides the use of a prostaglandin or prostaglandin analogue for treatment of diseases of the eye.

The present invention further provides the use of an intraocular pressure-reducing therapeutic agent in the manufacture of a medicament for the reduction of intraocular pressure in an eye of a patient in need thereof. In some embodiments, the medicament is a sustained release topical formulation. In some embodiments, the intraocular pressure-reducing therapeutic agent is capable of being continuously released over time to the eye. In certain embodiments, the intraocular pressure of the patient is reduced at least 10% from baseline. In certain embodiments, the intraocular pressure is reduced at least 15% from baseline, at least 20% from baseline, or at least 25% from baseline.

In specific embodiments, the intraocular pressure-reducing therapeutic agent is released for a period of time of at least about 30 days, at least about 60 days, or at least about 90 days. In some embodiments, the intraocular pressure-reducing therapeutic agent is an anti-glaucoma drug, for example an adrenergic agonist, an adrenergic antagonist, a beta blocker, a carbonic anhydrase inhibitor, a parasympathomimetic, a prostaglandin analog, a hypotensive lipid, a neuroprotectant, or combinations thereof. In one embodiment, the anti-glaucoma drug is latanoprost.

In many embodiments, the formulation is disposed in and eluted from an ocular implant, such as a punctal implant. In some embodiments, the formulation is impregnated within the punctal implant such that at least one surface of the implant is coated with the formulation. In some embodiments, the formulation is contained within a sustained release core disposed in the punctal implant.

It is contemplated that the punctal implant can contain an amount of intraocular pressure-reducing therapeutic agent consisting of about 3.5 micrograms, about 14 micrograms, about 21 micrograms or about 44 micrograms. In some embodiments, the punctal implant is inserted into one punctum of each of both eyes of the patient.

The formulation can be administered approximately once every 90 days, and the intraocular pressure-reducing therapeutic agent can be continuously released to the eye for a period of consisting of approximately 180 days, approximately 270 days, approximately 360 days, approximately 450 days, approximately 540 days, approximately 630 days, approximately 720 days, approximately 810 days or approximately 900 days.

In certain embodiments, between about 25 ng/day and about 250 ng/day of the intraocular pressure-reducing therapeutic agent is released. In one embodiment, the intraocular pressure is at least about 20 mm Hg before administering the intraocular pressure-reducing therapeutic agent. In some embodiments, the reduction in intraocular pressure is maintained for a continuous period of time consisting of: up to about 7 days, up to about 14 days, up to about 21 days, up to about 28 days, up to about 56 days, up to about 84 days, or up to about 105 days.

In some embodiments, patient noncompliance is significantly reduced compared to eye drop formulations of intraocular pressure-reducing therapeutic agents.

In certain embodiments, the intraocular pressure is associated with ocular hypertension. In some embodiments, the intraocular pressure is associated with glaucoma.

Also provided herein is the use of an intraocular pressure-reducing agent in the manufacture of a medicament for the reduction of intraocular pressure in an eye of a patient in need thereof, wherein the medicament is adapted for use in an implant that is inserted into at least one punctum of the eye, wherein the implant comprises a sustained release core comprising the intraocular pressure-reducing agent, wherein the intraocular pressure-reducing therapeutic agent is capable of being continuously released over time to the eye, and wherein the intraocular pressure is reduced at least about 10% from baseline.

In some embodiments, the intraocular pressure is reduced an amount selected from the group consisting of at least 15% from baseline, at least 20% from baseline and at least 25% from baseline. In certain embodiments, the intraocular pressure-reducing therapeutic agent is released for a period of time selected from the group consisting of at least about 30 days, at least about 60 days, and at least about 90 days.

In some embodiments, the sustained release core is disposed in an implant body. In certain embodiments, the patient is suffering from glaucoma. In certain embodiments, the implant, the sustained release core, or both are at least partially coated by an impermeable coating. In some embodiments, the impermeable coating comprises parylene. In one embodiment, the intraocular pressure-reducing therapeutic agent is latanoprost.

The present invention also provides a method to reduce intraocular pressure by inserting an implant into at least one punctum of a patient, wherein the implant is at least partially impregnated with latanoprost or other therapeutic agent(s) or includes a sustained release core containing at least latanoprost or other therapeutic agent(s), and wherein the implant releases latanoprost or other therapeutic agent(s) continuously for at least about 90 days. In one embodiment, the method treats elevated glaucoma-associated intraocular pressure by the insertion of an implant including latanoprost or other therapeutic agent(s) at least partially into a punctum of a subject to effect the sustained release of latanoprost or other therapeutic agent(s) to the subject, resulting in a reduction in the intraocular pressure of the associated eye of at least 6 mm Hg.

In some embodiments, the implant releases latanoprost or other therapeutic agent(s) during a continuous period of time from at least about 7 days, at least about 28 days, at least about 52 days, at least about 88 days, or at least about 90 days following insertion of the implant. In some embodiments, the implant releases between about 25 ng/day and about 250 ng/day of latanoprost or other therapeutic agent(s). In other embodiments the implant can release at least 250 ng/day of latanoprost or other therapeutic agent(s). In other other embodiments, the implant can release at least 350 ng/day or more of latanoprost or other therapeutic agent(s). In certain embodiments, the implant can release about 0.75 micrograms per day, about 1.0 micrograms per day, or about 1.5 micrograms or more per day of latanoprost or other therapeutic agent(s). In some embodiments, the topical formulation of an implant comprising latanoprost or other therapeutic agent(s) is administered to the eyes of a subject less than 10 times, less than 5 times, or less than 3 times during the continuous period of time.

In an embodiment, the invention provides a method to reduce intraocular pressure by inserting an implant into at least one punctum of a patient having an intraocular pressure (IOP) of about 22 mm Hg. The implant can be at least partially impregnated with latanoprost or other therapeutic agent(s) or can comprise a sustained release core containing at least latanoprost or other therapeutic agent(s), and the release of latanoprost or other therapeutic agent(s) from the implant results in the reduction of the IOP from about 22 mm Hg to about 16 mm Hg.

In certain embodiments, the invention provides a method to reduce intraocular pressure by inserting an implant into at least one punctum of a patient having an intraocular pressure (IOP) of about 21 mm Hg, about 20 mm Hg, about 19 mm Hg, about 18 mm Hg, about 17 mm Hg, about 16 mm Hg, about 15 mm Hg, about 14 mm Hg, about 13 mm Hg, about 12 mm Hg, about 11 mm Hg, or about 10 mm Hg. In an embodiment, the invention provides a method to treat primary open angle glaucoma. In other embodiments, the invention provides a method to treat angle closure glaucoma. In further embodiments, the invention provides a method to treat normal tension glaucoma. In still further embodiments, the invention provides a method to treat secondary glaucoma.

In certain embodiments, the reduction in intraocular pressure is maintained for a continuous period of time of up to about 7 days, up to about 14 days, up to about 21 days, up to about 28 days, up to about 52 days, up to about 88 days, or up to about 105 days. In an embodiment, the reduction in intraocular pressure is maintained for a continuous period of time of at least about 90 days. Another embodiment provides a course of treatment of about 90 days.

In certain embodiments, the variability in intraocular pressure over the course of treatment after one week is less than about 1 mm Hg. In other embodiments, the variability in intraocular pressure over the course of treatment after one week is less than about 2 mm Hg. In other embodiments, the variability in intraocular pressure over the course of treatment after one week is less than about 3 mm Hg. In an embodiment, once the intraocular pressure is reduced by about 6 mm Hg, the variability in intraocular pressure at any given time point during the remainder of the course of treatment is less than about 1 mm Hg.

The invention described herein also provides a method to reduce intraocular pressure by inserting a sustained release implant into at least one punctum of a patient wherein the intraocular pressure of the associated eye is reduced by at least about 25%.

In some embodiments, the invention provides a method to treat a patient having ocular hypertension by administering a topical formulation consisting of latanoprost or other therapeutic agent(s) eluted from a drug core or other implant body that is configured for at least partial insertion into at least one punctum of a patient, wherein the formulation is capable of reducing intraocular pressure for at least 90 days. In an embodiment, the drug core is configured for insertion into an ocular implant. In still further embodiment, the ocular implant is a punctal implant, for example a punctal plug.

In an embodiment, the methods of the invention result in a reduction in the intraocular pressure of at least 10% by 1 day after inserting the implant or at least 20% within 7 days after inserting the implant. In some embodiments, the reduction in intraocular pressure is maintained for at least 75 days. In other embodiments, the reduction in intraocular pressure is maintained for at least 90 days. In other embodiments, the reduction in intraocular pressure is maintained for at least 120 days. In still other embodiments, about 20% reduction, about 25% reduction, about 30% reduction, about 35% reduction, about 40% reduction, about 45% reduction, or about 50% or greater reduction in the intraocular pressure is present at about 90 days or less after insertion of the punctal implant.

In an embodiment, the intraocular pressure prior to inserting the punctal implant is at least 20 mm Hg. In some embodiments, the intraocular pressure is about 16 mm Hg about 7 days after inserting the implant.

The methods of the invention described herein also provide an implant at least partially impregnated with a therapeutic agent or having a sustained release core that includes a non-biodegradable polymer. In some embodiments, the sustained release core includes silicone.

The implant can be inserted into the upper punctum or the lower punctum, or implants can be inserted into both the upper and lower puncta. The implant may be inserted into one punctum of one eye or implants may be inserted into each punctum of both eyes.

The implant may contain at least 3 micrograms, at least 10 micrograms, at least 20 micrograms, at least 30 micrograms, at least 40 micrograms, or between about 3.5 and 135 micrograms of latanoprost or other therapeutic agent(s). In other embodiments, the implant may contain more than 40 micrograms of latanoprost or other therapeutic agent(s). In other embodiments, the implant may contain a therapeutic agent, for example one or more prostaglandin derivatives, such as travoprost, bimatoprost, etc or other therapeutic agent(s) useful in the treatment of elevated intraocular pressure, such as beta blockers, carbonic anhydrase inhibitors, alpha adrenergic antagonists, and the like. In some embodiments, the amount of the therapeutic agent or agents released from the implant is sufficient to treat an ocular condition for a sustained period of time, for example about 7 days or longer, about 30 days or longer, about 45 days or longer, about 60 days or longer, about 75 days or longer, about 90 days, or longer. In some embodiments, the implant contains about 3.5 micrograms, about 14 micrograms, about 21 micrograms, about 42 micrograms or about 44 micrograms of latanoprost or other therapeutic agent(s). In other embodiments, the implant contains about 50, about 60, about 70 or about 80 micrograms of latanoprost or other therapeutic agent(s). In other embodiments, the implant contains sufficient quantities of therapeutic agent for sustained release at therapeutic levels over the desired treatment period.

The invention further provides a method to treat elevated intraocular pressure by inserting an implant into at least one punctum of a patient, wherein the implant is impregnated with or has a sustained release core containing about 14 micrograms of latanoprost or other therapeutic agent(s), wherein the implant remains inserted for at least 90 days, and wherein the intraocular pressure is reduced substantially as shown in FIG. 1.

In some embodiments, a topical formulation consisting essentially of latanoprost or other therapeutic agent(s) and a pharmaceutically acceptable vehicle is provided, wherein the formulation is eluted from a solid drug core or other implant body configured for at least partial insertion into at least one punctum of a patient, wherein the formulation is capable of reducing intraocular pressure for at least 90 days.

The invention further provides a reduction in patient noncompliance compared to eye drop formulations of latanoprost and other therapeutic agent(s). A single insertion procedure provides continuous administration of latanoprost or other therapeutic agent(s) for a sustained period of time, avoiding patient noncompliance that is associated with eye drop administration.

The invention further provides a method of reducing intraocular pressure and in some embodiments, lowering the occurrence of adverse effects due to topical administration of therapeutic agents for treating eye diseases, for example prostaglandins including but not limited to latanoprost, travoprost, and bimatoprost, and as a further example, timolol, comprising delivering said therapeutic agents to the eye from an implant including but not limited to the implants as disclosed herein. In an embodiment such implant may be partially or completely impregnated with said therapeutic agents. For instance, the implant body can comprise a matrix of a polymeric component and one or more therapeutic agents. The one or more therapeutic agents can be distributed substantially thought the matrix and released over time. In another embodiment, such implant may comprise a sustained release drug core containing said therapeutic agents.

BRIEF DESCRIPTION OF THE FIGURES

In the drawings, like numerals can be used to describe similar components throughout the several views. The drawings illustrate generally, by way of example, but not by way of limitation, various embodiments discussed in the present document.

FIG. 10 illustrates mean IOP changes from baseline in the CORE study.

FIG. 13 illustrates percent reduction in IOP in the CORE study compared to published latanoprost, timolol and bimatoprost eye drop studies (References: Rate of Response to Latanoprost or Timolol in Patients with Ocular Hypertension or Glaucoma. J Glaucoma 2003; 12:466-469; A Six-month Randomized Clinical Trial Comparing the Intraocular Pressure—lowering efficacy of Bimatoprost and Latanoprost in Patients With Ocular Hypertension or Glaucoma. Am J Opthalmol 2003; 135:55-63). Percentages for latanoprost and timolol are estimates from graphs.

FIG. 16 illustrates ocular adverse events (AEs) in the CORE study.

FIG. 17 illustrates ocular adverse events in the CORE study compared to latanoprost eye drop studies. *Xalatan Ophthalmic Solution 0.005% (50 mg/mL) (Pharmacia) Jun. 5, 1996 Approval: Medical Officers Review, pp. 93, 98-100. Provided by FOI Services. **A Six-month Randomized Clinical Trial Comparing the Intraocular Pressure—lowering efficacy of Bimatoprost and Latanoprost in Patients with Ocular Hypertension or Glaucoma. Am J Opthalmol 2003; 135:55-63. *Other adverse events included eyelash growth. ***Of 198 patients (p. 98 of Xalatan Ophthalmic Solution 0.005% (50 mg/mL) (Pharmacia) Jun. 5, 1996 Approval: Medical Officers Review).

FIG. 18 illustrates ocular adverse events in the CORE study compared to eye drop studies of latanoprost, travoprost, timolol, and bimatoprost. (1) Travoprost Compared With Latanoprost and Timolol in Patients With Open-angle Glaucoma or Ocular Hypertension. Am J Opthalmol 2001; 132:472-484. *Other AEs included ocular pain, cataract, dry eye, blepharitis, blurred vision. (2) A Six-month Randomized Clinical Trial Comparing the Intraocular Pressure—lowering efficacy of Bimatoprost and Latanoprost in Patients With Ocular Hypertension or Glaucoma. Am J Opthalmol 2003; 135:55-63. *Other AEs included eyelash growth. (3) One-Year, Randomized Study Comparing Bimatoprost and Timolol in Glaucoma and Ocular Hypertension. Arch Opthalmol V120 October 2002 1286-1293. *Other AEs included eyelash growth, eye dryness, eye pain. Also included bimatoprost BID group (higher AE incidence).

DETAILED DESCRIPTION OF THE INVENTION

Definitions

Figure 1:
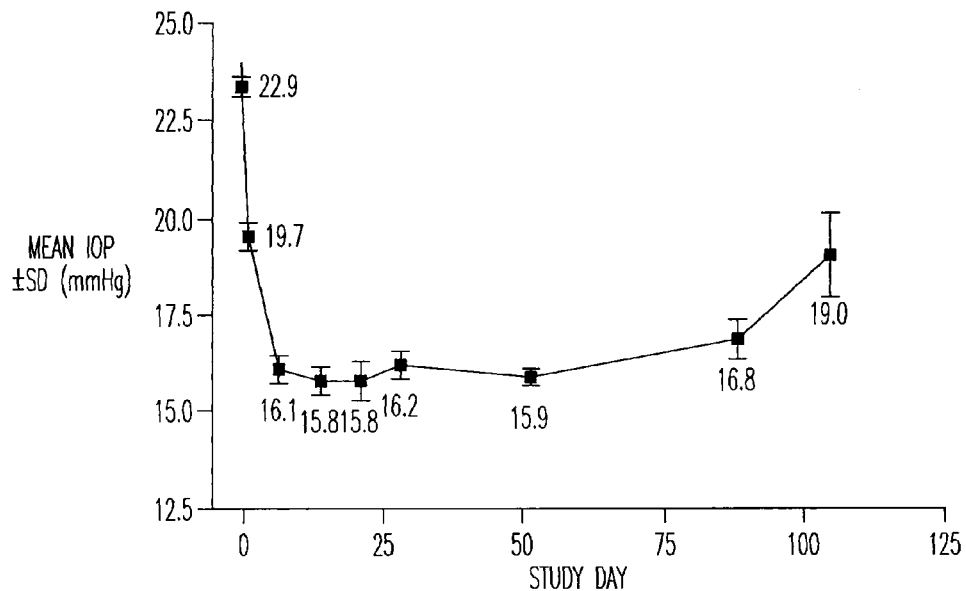
FIG. 1 illustrates mean intraocular pressure in subjects treated with 14 μg Latanoprost Punctal Plug Delivery System.

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to a stated amount.

As used herein, the term "adverse event" refers to any undesirable clinical event experienced by a patient undergoing a therapeutic treatment including a drug and/or a medical device, whether in a clinical trial or a clinical practice. Adverse events include a change in the patient's condition or laboratory results, which has or could have a deleterious effect on the patient's health or well-being. For example, adverse events include but are not limited to: device malfunction identified prior to placement, device malposition, device malfunction after placement, persistent inflammation, endophthalmitis, corneal complications (corneal edema, opacification, or graft decompensation), chronic pain, iris pigmentation changes, conjunctival hyperemia, eyelash growth (increased length, thickness, pigmentation, and number of lashes), eyelid skin darkening, intraocular inflammation (iritis/uveitis), macular edema including cystoid macular edema, blurred vision, burning and stinging, foreign body sensation, itching, punctate epithelial keratopathy, dry eye, excessive tearing, eye pain, lid crusting, lid discomfort/pain, lid edema, lid erythema, photophobia, VA decrease, conjunctivitis, diplopia, discharge from the eye, retinal artery embolus, retinal detachment, vitreous hemorrhage from diabetic retinopathy, upper respiratory tract infection/cold/flu, chest pain/angina pectoris, muscle/joint/back pain, and rash/allergic skin reaction, eye pruritus, increase in lacrimation, ocular hyperemia and punctate keratitis.

As used herein, the phrase "consisting essentially of" limits a composition to the specified materials or steps and those additional, undefined components that do not materially affect the basic and novel characteristic(s) of the composition.

As used herein, the term "continuous" or "continuously" means unbroken or uninterrupted. For example, continuously administered active agents are administered over a period of time without interruption.

As used herein, the term "eye" refers to any and all anatomical tissues and structures associated with an eye. The eye is a spherical structure with a wall having three layers: the outer sclera, the middle choroid layer and the inner retina. The sclera includes a tough fibrous coating that protects the inner layers. It is mostly white except for the transparent area at the front, the cornea, which allows light to enter the eye. The choroid layer, situated inside the sclera, contains many blood vessels and is modified at the front of the eye as the pigmented iris. The biconvex lens is situated just behind the pupil. The chamber behind the lens is filled with vitreous humour, a gelatinous substance. The anterior and posterior chambers are situated between the cornea and iris, respectively and filled with aqueous humour. At the back of the eye is the light-detecting retina. The cornea is an optically transparent tissue that conveys images to the back of the eye. It includes avascular tissue to which nutrients and oxygen are supplied via bathing with lacrimal fluid and aqueous humour as well as from blood vessels that line the junction between the cornea and sclera. The cornea includes one pathway fro the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

As used herein, the term "implant" refers to a structure that can be configured to contain or be impregnated with a drug, for example via a drug core or a drug matrix, such as those as disclosed in this patent document and in WO 07/115,261, which is herein incorporated by reference in its entirety, and which is capable of releasing a quantity of active agent, such as latanoprost or other therapeutic agent(s), into tear fluid for a sustained release period of time when the structure is implanted at a target location along the path of the tear fluid in the patient. The terms "implant," "plug," "punctal plug," and "punctal implant" are meant herein to refer to similar structures. Likewise, the terms "implant body" and "plug body" are meant herein to refer to similar structures. The implants described herein may be inserted into the punctum of a subject, or through the punctum into the canaliculus. The implant may be also the drug core or drug matrix itself, which is configured for insertion into the punctum without being housed in a carrier such as a punctal implant occluder, for example having a polymeric component and a latanoprost or other therapeutic agent(s) component with no additional structure surrounding the polymeric component and latanoprost or other therapeutic agent(s) component.

As used herein, "loss of efficacy" (LoE) is defined as an IOP increase to baseline (post-washout) IOP in either or both eyes while wearing an L-PPDS continuously from Day 0. Subjects were followed for at least 4 weeks before the subject could complete the study due to LoE and LoE was confirmed at 2 sequential visits.

As used herein, a "pharmaceutically acceptable vehicle" is any physiological vehicle known to those of ordinary skill in the art useful in formulating pharmaceutical compositions. Suitable vehicles include polymeric matrices, sterile distilled or purified water, isotonic solutions such as isotonic sodium chloride or boric acid solutions, phosphate buffered saline (PBS), propylene glycol and butylene glycol. Other suitable vehicular constituents include phenylmercuric nitrate, sodium sulfate, sodium sulfite, sodium phosphate and monosodium phosphate. Additional examples of other suitable vehicle ingredients include alcohols, fats and oils, polymers, surfactants, fatty acids, silicone oils, humectants, moisturizers, viscosity modifiers, emulsifiers and stabilizers. The compositions may also contain auxiliary substances, i.e. antimicrobial agents such as chlorobutanol, parabans or organic mercurial compounds; pH adjusting agents such as sodium hydroxide, hydrochloric acid or sulfuric acid; and viscosity increasing agents such as methylcellulose. The final composition should be sterile, essentially free of foreign particles, and have a pH that allows for optimum drug stability.

As used herein, the term "punctum" refers to the orifice at the terminus of the lacrimal canaliculus, seen on the margins of the eyelids at the lateral extremity of the lacus lacrimalis. Puncta (plural of punctum) function to reabsorb tears produced by the lacrimal glands. The excretory part of the lacrimal drainage system includes, in flow order of drainage, the lacrimal puncta, the lacrimal canaliculi, the lacrimal sac and the lacrimal duct. From the lacrimal duct, tears and other flowable materials drain into a passage of the nasal system. The lacrimal canaliculi include an upper (superior) lacrimal canaliculus and a lower (inferior) lacrimal canaliculus, which respectively terminate in an upper and lower lacrimal punctum. The upper and lower punctum are slightly elevated at the medial end of a lid margin at the junction of the ciliary and lacrimal portions near a conjunctival sac. The upper and lower punctum are generally round or slightly ovoid openings surrounded by a connective ring of tissue. Each of the puncta leads into a vertical portion of their respective canaliculus before turning more horizontal at a canaliculus curvature to join one another at the entrance of the lacrimal sac. The canaliculi are generally tubular in shape and lined by stratified squamous epithelium surrounded by elastic tissue, which permits them to be dilated.

The terms "subject" and "patient" refer to animals such as mammals, including, but not limited to, primates (e.g., humans), cows, sheep, goats, horses, dogs, cats, rabbits, rats, mice and the like. In many embodiments, the subject or patient is a human.

A "therapeutic agent" can comprise a drug and may be any of the following or their equivalents, derivatives or analogs, including anti-glaucoma medications (e.g. adrenergic agonists, adrenergic antagonists (beta blockers), carbonic anhydrase inhibitors (CAIs, systemic and topical), parasympathomimetics (e.g. cholinergic drug), prostaglandins and hypotensive lipids, and combinations thereof), antimicrobial agents (e.g., antibiotic, antiviral, antiparacytic, antifungal, etc.), a corticosteroid or other anti-inflammatory (e.g., an NSAID), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic or the like. Examples of conditions that may be treated with the therapeutic agent(s) include but are not limited to glaucoma, pre and post surgical treatments, ocular hypertension, dry eye and allergies. In some embodiments, the therapeutic agent may be a lubricant or a surfactant, for example a lubricant to treat dry eye.

Exemplary therapeutic agents include, but are not limited to thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; anti-platelet agents; antimitotics; microtubule inhibitors; antisecretory agents; active inhibitors; remodeling inhibitors; antisense nucleotides; anti-metabolites; antiproliferatives (including antiangiogenesis agents); anticancer chemotherapeutic agents; anti-inflaTnmatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs, such as salicylate, indomethacin, ibuprofen, diclofenac, flurbiprofen, piroxicam indomethacin, ibuprofen, naxopren, piroxicam and nabumetone). Such anti inflammatory steroids contemplated for use in the methodology of the present invention, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, pholpholine iodine, demecarium bromide); antineoplastics (such as carmustine, cisplatin, fluorouracil3; immunological drugs (such as vaccines and immune stimulants); hormonal agents (such as estrogens, -estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agent(s) such as prostaglandins, antiprostaglandins, prostaglandin precursors, including antiglaucoma drugs including beta-blockers such as Timolol, betaxolol, levobunolol, atenolol, and prostaglandin analogues such as Bimatoprost, travoprost, Latanoprost, etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

The term "topical" refers to any surface of a body tissue or organ. A topical formulation is one that is applied to a body surface, such as an eye, to treat that surface or organ. Topical formulations as used herein also include formulations that can release therapeutic agents into the tears to result in topical administration to the eye.

As used herein, the term "treating" or "treatment" of a disease includes: (1) preventing the disease, i.e., causing the clinical symptoms of the disease not to develop in a subject that may be exposed to or predisposed to the disease but who does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The implants described herein are contemplated to be useful for treatment of various diseases including, but not limited to, diseases or malconditions of the eye. These diseases or malconditions include diabetic retinopathy, uveitis, intraocular inflammation, keratitis, dry eye, macular edema including cystoid macular edema, infection, macular degeneration, blurred vision, herpetic conjunctivitis, blepharitis, retinal or choroidal neovascularizaton, and other proliferative eye diseases. Also contemplated herein is the treatment of additional diseases including, but not limited to, rheumatic disease, dizziness, infectious diseases including upper respiratory tract infections (cold/flu), chest pain/angina pectoris, heart disease, muscle/joint/back pain, autoimmune disease, inflammatory conditions, cancer or other proliferative diseases, infections, vascular disease, diabetes and diseases of the central nervous system including migraine headache. Both local and systemic delivery of therapeutic agents from the plugs described herein may be employed.

The invention provides the use of latanoprost or another active agent or agents for treatment of diabetic retinopathy, uveitis, intraocular inflammation, keratitis, dry eye, macular edema including cystoid macular edema, infection, macular degeneration, blurred vision, herpetic conjunctivitis, blepharitis, retinal or choroidal neovascularizaton, and other proliferative eye diseases. Also provided herein is the use of latanoprost or other active agent(s) for treatment of rheumatic disease, dizziness, infectious diseases including upper respiratory tract infections (cold/flu), chest pain/angina pectoris, heart disease, muscle/joint/back pain, autoimmune disease, inflammatory conditions, cancer or other proliferative disease, infections, vascular disease, diabetes and diseases of the central nervous system including migraine headache. In some embodiments, the invention provides the use of an anti-glaucoma drug for treatment of the above diseases. In certain embodiments, the use of a prostaglandin or prostaglandin analogue for treatment of the above diseases is provided.

Elevated Intraocular Pressure:

Ocular hypertension (OH) and primary open angle glaucoma (POAG) are caused by a build-up of aqueous humor in the anterior chamber primarily due to the eye's inability to properly drain aqueous fluid. The ciliary body, situated at the root of the iris, continuously produces aqueous humor. It flows into the anterior chamber and then drains via the angle between the cornea and iris through the trabecular meshwork and into a channel in the sclera. In the normal eye, the amount of aqueous humor being produced is equal to the amount that is draining out. However, in an eye in which this mechanism is compromised, intraocular pressure (IOP) rises. Elevated IOP represents a major risk factor for glaucomatous field loss. Results from several studies indicate that early intervention targeted at lowering intraocular pressure retards the progression of optic nerve damage and loss of visual fields that lead to decreased vision and blindness.

Latanoprost:

A preferred therapeutic agent for use in the methods described herein is latanoprost. Latanoprost is a prostaglandin $F_{2\alpha}$ analogue. Its chemical name is isopropyl-(Z)-7[(1R, 2R,3R,5S)3,5-dihydroxy-2-[(3R)-3-hydroxy-5-phenylpentyl]cyclopentyl]-5-heptenoate. Its molecular formula is $C_{26}H_{40}O_5$ and its chemical structure is:

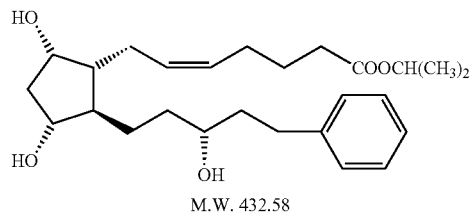

M.W. 432.58

Latanoprost is a colorless to slightly yellow oil that is very soluble in acetonitrile and freely soluble in acetone, ethanol, ethyl acetate, isopropanol, methanol and octanol. It is practically insoluble in water.

Latanoprost is believed to reduce intraocular pressure (IOP) by increasing the outflow of aqueous humor. Studies in animals and man suggest that the main mechanism of action is increased uveoscleral outflow of aqueous fluid from the eyes. Latanoprost is absorbed through the cornea where the isopropyl ester prodrug is hydrolyzed to the acid form to become biologically active. Studies in man indicate that the peak concentration in the aqueous humor is reached about two hours after topical administration.

Xalatan® latanoprost ophthalmic solution is a commercially available product indicated for the reduction of elevated IOP in patients with open-angle glaucoma or ocular hypertension. The amount of latanoprost in the commercially available product Xalatan® is approximately 1.5 micrograms/drop. As described above, eye drops, though effective, can be inefficient and require multiple applications to maintain the therapeutic benefit. Low patient compliance compounds these effects.

Patient Noncompliance:

Numerous studies have been published showing high noncompliance by patients using eye drops for treatment of various ocular disorders. One study showed only 64% of patients used the eye drops as directed (Winfield et al., 1990). Another study showed that 41% of patients using eye drops for glaucoma missed six or more doses over a 30-day period (Norell and Granstrom 1980).

The invention described herein provides methods to treat glaucoma that avoid the problem of noncompliance associated with eye drop administration. In some embodiments, the methods of the invention reduce patient noncompliance significantly compared to eye drop administration, by at least 10%, at least 20%, at least 30%, at least 40%, at least 50%, at least 60%, at least 70%, at least 80%, or at least 90%. In some embodiments, overall patient noncompliance with the methods described herein is about 5%, about 10%, about 15%, about 20%, or about 25%.

Patient noncompliance may occur if an implant of the invention is intentionally removed by a patient or if the patient does not seek reinsertion of the implant after such implant has been unintentionally lost from the punctum of the patient. Patient compliance is considered to be met if the implant is intentionally removed and the patient seeks reinsertion within less than about 48 hours. Patient compliance is also considered to be met if the implant is intentionally removed and the patient seeks reinsertion within less than about 24 hours of removal or loss of the implant.

Adverse Events in Clinical Trials and Clinical Practice:

Based on Xalatan® product information, the most frequently reported ocular adverse events associated with latanoprost in clinical trials were blurred vision, burning and stinging, conjunctival hyperemia, foreign body sensation, itching, increased pigmentation of the iris, and punctate keratopathy. These events occurred in 5% to 15% of subjects. Less than 1% of subjects required discontinuation of therapy because of intolerance to conjunctival hyperemia. Dry eye, excessive tearing, eye pain, lid crusting, lid discomfort/pain, lid edema, lid erythema, and photophobia were reported in 1% to 4% of subjects. Conjunctivitis, diplopia, and discharge from the eye were reported in <1% of subjects. Retinal artery embolus, retinal detachment, and vitreous hemorrhage from diabetic retinopathy were rarely reported.

The most common systemic adverse events in clinical trials were upper respiratory tract infection/cold/flu, which occurred at a rate of approximately 4%. Chest pain/angina pectoris, muscle/joint/back pain, and rash/allergic skin reaction each occurred at a rate of 1% to 2%.

In clinical practice, the following adverse events associated with latanoprost have been noted: asthma and exacerbation of asthma; corneal edema and erosions; dyspnea; eyelash and vellus hair changes (increased length, thickness, pigmentation, and number); eyelid skin darkening; herpes keratitis; intraocular inflammation (iritis/uveitis); keratitis; macular edema, including cystoid macular edema; misdirected eyelashes sometimes resulting in eye irritation; dizziness, headache, and toxic epidermal necrolysis.

Methods of Treatment:

The invention described herein provides methods to treat glaucoma, elevated intraocular pressure, and glaucoma-associated elevated intraocular pressure with a therapeutic agent. In many embodiments, a method of treating an eye with latanoprost is provided. In some embodiments, the therapeutic agent is released to the eye over a sustained period of time. In an embodiment, the sustained period of time is approximately 90 days. In some embodiments, the method comprises inserting through a punctum an implant having a body and a drug core so that the drug core is retained near the punctum. In some embodiments, the method comprises inserting through a punctum an implant having a body impregnated with a therapeutic agent. In some embodiments, an exposed surface of the drug core or impregnated body located near the proximal end of the implant contacts the tear or tear film fluid and the latanoprost or other therapeutic agent(s) migrates from the exposed surface to the eye over a sustained period of time while the drug core and body is at least partially retained within the punctum. In many embodiments, a method of treating an eye with latanoprost or other therapeutic agent(s) is provided, the method comprising inserting through a punctum into a canalicular lumen an implant having an optional retention structure so that the implant body is anchored to a wall of the lumen by the retention structure. The implant releases effective amounts of latanoprost or other therapeutic agent(s) from a drug core or other agent supply into a tear or tear film fluid of the eye. In some embodiments, the drug core may be removed from the retention structure while the retention structure remains anchored within the lumen. A replacement drug core can then be attached to the retention structure while the retention structure remains anchored. At least one exposed surface of the replacement drug core releases latanoprost or other therapeutic agent(s) at therapeutic levels over a sustained period.

A replacement implant, or in other embodiments, a replacement drug core which can in some embodiments be attached to or include its own retention structure, can be attached to the retention structure approximately every 90 days to result in continuous release of the drug to the eye for a period of time of approximately 180 days, approximately 270 days, approximately 360 days, approximately 450 days, approximately 540 days, approximately 630 days, approximately 720 days, approximately 810 days or approximately 900 days. In some embodiments, a replacement implant can be inserted into the punctum approximately every 90 days to achieve release of the drug to the eye for extended periods of time, including up to about 180 days, about 270 days, about 360 days, about 450 days, about 540 days, about 630 days, about 720 days, about 810 days or about 900 days.

In other embodiments, a method for treating an eye with latanoprost or other therapeutic agent(s) is provided, the method comprising inserting a drug core or other implant body at least partially into at least one punctum of the eye. The drug core may or may not be associated with a separate implant body structure. The drug core or agent-impregnated implant body provides sustained release delivery of latanoprost or other therapeutic agent(s) at therapeutic levels. In some embodiments, the sustained release delivery of latanoprost or other therapeutic agent(s) continues for up to 90 days.

In many embodiments, a method for treating an eye with latanoprost or other therapeutic agent(s) is provided, the method comprising inserting a distal end of an implant into at least one punctum of the eye. In some embodiment, a retention structure of the implant can be expanded so as to inhibit expulsion of the implant. The expansion of the retention structure can help to occlude a flow of tear fluid through the punctum. In some embodiments, the implant is configured such that, when implanted, an at least 45 degree angled intersection exists between a first axis, defined by a proximal end of the implant, and a second axis, defined by the distal end of the implant, to inhibit expulsion of the implant. Latanoprost or other therapeutic agent(s) is delivered from a proximal end of the implant to the tear fluid adjacent the eye. Delivery of the latanoprost or other therapeutic agent(s) is inhibited distally of the proximal end.

The methods of the invention provide sustained release of latanoprost or other therapeutic agent(s). In some embodiments, the active agent is released from the implant for at least one week, at least two weeks, at least three weeks, at least four weeks, at least five weeks, at least six weeks, at least seven weeks, at least eight weeks, at least nine weeks, at least ten weeks, at least eleven weeks, at least twelve weeks, at least thirteen weeks, at least fourteen weeks, at least fifteen weeks, or at least sixteen weeks. In some embodiments, the active agent is latanoprost. In an embodiment, the latanoprost or other therapeutic agent(s) is released for at least twelve weeks. In another embodiment, the methods of treatment according to the present invention as described above further comprises an adjunctive therapy with a latanoprost-delivering eye drop solution, for example, Xalatan®.

The amount of latanoprost or other therapeutic agent(s) associated with the implant may vary depending on the desired therapeutic benefit and the time during which the device is intended to deliver the therapy. Since the devices of the present invention present a variety of shapes, sizes and delivery mechanisms, the amount of drug associated with the device will depend on the particular disease or condition to be treated, and the dosage and duration that is desired to achieve the therapeutic effect. Generally, the amount of latanoprost or other therapeutic agent(s) is at least the amount of drug that, upon release from the device, is effective to achieve the desired physiological or pharmacological local or systemic effects.

Certain embodiments of the implants of the present invention can be configured to provide delivery of latanoprost or other therapeutic agent(s) at daily rates that are similar or equivalent to the therapeutically effective drop form of treatment. Other embodiments of the implants of the present invention can be configured to provide delivery of latanoprost or other therapeutic agent(s) at daily rates that exceed the therapeutically effective drop form of treatment.

Embodiments of the implants of the present invention can also be configured to provide delivery of latanoprost or other therapeutic agent(s) at a daily rate that is substantially below the therapeutically effective drop form of treatment so as to provide a large therapeutic range with a wide safety margin. For example, many embodiments treat the eye with therapeutic levels for extended periods that are no more than 5 or 10 percent of the daily drop dosage. In specific embodiments, the quantity can be less than 5% of the recommended drop-administered quantity. Consequently, during an initial bolus or washout period of about one to three days, the implant can elute latanoprost or other therapeutic agent(s) at a rate that is substantially higher than the sustained release levels and well below the daily drop form dosage. For example, with an average sustained release level of 100 ng per day, and an initial release rate of 1000 to 1500 ng per day, the amount of drug initially released is less than the 2500 ng of drug that may be present in a drop of drug delivered to the eye. This use of sustained release levels substantially below the amount of drug in one or more drops administered daily allows the device to release a therapeutically beneficial amount of drug to achieve the desired therapeutic benefit with a wide safety margin, while avoiding an inadequate or excessive amount of drug at the intended site or region.

For comparison purposes, standard treatment with drops such as Xalatan® drops delivers about 1.5 micrograms of latanoprost, assuming a 35 microliter drop volume. In contrast, in one embodiment, the implant of the instant invention can deliver an amount of drug that will be significantly less than conventional drop administration described above. In other embodiments, the sustained release of more than 100 ng per day, for example, up to 1.5 micrograms of latanoprost per day, can be administered. Although the sustained release amount of latanoprost released each day can vary, a sustained release of approximately 100 ng per day using the implant of the invention corresponds to about 6% of the latanoprost applied with a single drop of a 0.005% solution.

Methods of inserting and removing the implant are known to those of skill in the art. For instance, tools for insertion and removal/extraction of implants are described in U.S. Patent Application No. 60/970,840 (filed Sep. 7, 2007 and entitled Insertion and Extraction Tools for Punctal Implants), the disclosure of which is incorporated herein in its entirety. Generally, for placement, the size of a punctal implant to be used may be determined by using suitable magnification or, if provided, using a sizing tool that accompanies the punctal implant. The patient's punctum may be dilated if necessary to fit the punctal implant. A drop of lubricant may be applied if necessary to facilitate placement of the implant into the punctum. Using an appropriate placement instrument, the implant may be inserted into the superior or inferior punctum of the eye. After placement, the cap of the implant may be visible. This process may be repeated for the patient's other eye. For removal of the implant, small surgical forceps may be used to securely grasp the implant at the tube section below the cap. Using a gentle tugging motion the implant may be gently retrieved.

Implant:

In some embodiments, latanoprost or other therapeutic agent(s) is administered for a sustained period of time by a drug matrix core which may or may not be associated with a separate implant body structure. In certain embodiments, an implant for use in the methods described herein is provided. The implant can be configured, when implanted at a target location along the path of tear fluid in the patient, to release a quantity of latanoprost or other therapeutic agent(s) into the tear fluid each day for a sustained release period of days, weeks, or months. The implant can be one of any number of different designs that releases latanoprost or other therapeutic agent(s) for a sustained period of time. The disclosures of the following patent documents, which describe example implant structure or processing embodiments for use in the methods of the current invention and methods of making those implants, are incorporated herein by reference in their entirety: U.S. Application Ser. No. 60/871,864 (filed Dec. 26, 2006 and entitled Nasolacrimal Drainage System Implants for Drug Therapy); U.S. application Ser. No. 11/695,537 (filed Apr. 2, 2007 and entitled Drug Delivery Methods, Structures, and Compositions for Nasolacrimal System); U.S. Application Ser. No. 60/787,775 (filed Mar. 31, 2006 and entitled Nasolacrimal Drainage System Implants for Drug Therapy); U.S. application Ser. No. 11/695,545 (filed Apr. 2, 2007 and entitled Nasolacrimal drainage system implants for drug therapy); U.S. application Ser. No. 11/571,147 (filed Dec. 21, 2006 and entitled Treatment Medium Delivery Device and Methods for Delivery of Such Treatment Mediums to the Eye Using Such a Delivery Device); U.S. Application Ser. No. 60/970,696 (filed Sep. 7, 2007 and entitled Expandable Nasolacrimal Drainage System Implants); U.S. Application Ser. No. 60/974,367 (filed Sep. 21, 2007 and entitled Expandable Nasolacrimal Drainage System Implants); U.S. Application Ser. No. 60/970,699 (filed Sep. 7, 2007 and entitled Manufacture of Drug Cores for Sustained Release of Therapeutic Agents); U.S. Application Ser. No. 60/970,709 (filed Sep. 7, 2007 and entitled Nasolacrimal Drainage System Implants for Drug Delivery); U.S. Application Ser. No. 60/970,720 (filed Sep. 7, 2007 and entitled Manufacture of Expandable Nasolacrimal Drainage System Implants); U.S. Application Ser. No. 60/970,755 (filed Sep. 7, 2007 and entitled Prostaglandin Analogues for Implant Devices and Methods); U.S. Application Ser. No. 60/970,820 (filed Sep. 7, 2007 and entitled Multiple Drug Delivery Systems and Combinations of Drugs with Punctal Implants); U.S. Application Ser. No. 61/049,347 (filed Apr. 30, 2008 and entitled Lacrimal Implants and Related Methods); U.S. Application Ser. No. 61/049,360 (filed Apr. 30, 2008 and entitled Lacrimal Implants and Related Methods); U.S. Application Ser. No. 61/052,595 (filed May 12, 2008 and entitled Lacrimal Implants and Related Methods); U.S. Application Ser. No. 61/075,309 (filed Jun. 24, 2008 and entitled Lacrimal Implants and Related Methods); U.S. Application Ser. No. 61/154,693 (filed Feb. 23, 2009 and entitled Lacrimal Implants and Related Methods); U.S. Application Ser. No. 61/209,036 (filed Mar. 2, 2009 and entitled Lacrimal Implants and Related Methods); U.S. Application Ser. No. 61/209,630 (filed Mar. 9, 2009 and entitled Lacrimal Implants and Related Methods); U.S. Application Ser. No. 61/036,816 (filed Mar. 14, 2008 and entitled Lacrimal Implants and Related Methods); U.S. Application Ser. No. 61/049,337 (filed Apr. 30, 2008 and entitled Lacrimal Implants and Related Methods); U.S. application Ser. No. 12/432,553 (filed Apr. 29, 2009 and entitled Composite Lacrimal Insert and Related Methods); U.S. Application Ser. No. 61/049,317 (filed Apr. 30, 2008 and entitled Drug-Releasing Polyurethane Lacrimal Insert); U.S. application Ser. No. 12/378,710 (filed Feb. 17, 2009 and entitled Lacrimal Implants and Related Methods); U.S. application Ser. No. 12/283,002 (filed Sep. 5, 2008 and entitled Surface Treated Implantable Articles and Related Methods); U.S. application Ser. No. 12/231,989 (filed Sep. 5, 2008 and entitled Lacrimal Implants and Related Methods); U.S. application Ser. No. 12/231,986 (filed Sep. 5, 2008 and entitled Drug Cores for Sustained Release of Therapeutic Agents); U.S. application Ser. No. 12/231,987 (filed Sep. 5, 2008 and entitled Lacrimal Implant Detection); U.S. application Ser. No. 10/825,047 (filed Apr. 15, 2004 and entitled Drug Delivery via Punctal Plug); International Published Application WO 2006/014434; and International Application Serial No. PCT/US2007/065789 (filed Mar. 31, 2006, published as WO 2007/115259 and entitled Nasolacrimal Drainage System Implants for Drug Therapy).

Generally, the implant comprises a body. In some embodiments, the implant body has a distal end portion and a proximal end portion. The distal end portion of the body is at least partially insertable into the punctum to the canalicular lumen of the patient. The implant body may be at least impregnated with latanoprost or other therapeutic agent(s) or otherwise comprise latanoprost or other therapeutic agent(s), such as within a matrix drug core that is inserted into the implant body. Exposure of the matrix drug core or impregnated body to the tear fluid causes an effective release of latanoprost or other active agent into the tear fluid over a sustained period. The implant may include a sheath disposed over at least a portion of the drug core to inhibit release of latanoprost or other therapeutic agent(s) from certain portions thereof. The implant body may have an outer surface configured to engage luminal wall tissues so as to inhibit expulsion when disposed therein. In many embodiments, an integral feedback or other projection is connected around the sheath near the proximal end of the drug core. In an embodiment, the feedback or other projection includes one or more wings sized to remain outside the punctum so as to retain the proximal end of the drug core near the punctum. In other embodiments, the feedback or other projection includes a full or partial (e.g., trimmed) head portion connected around the sheath near the proximal end of the drug core. The head portion can be sized to remain outside the punctum so as to retain the proximal end of the drug core near the punctum.

In some embodiments, the implant comprises a drug core alone, lacking an additional structure surrounding the core. For example, in some embodiments, the implant may comprise a body formed of a drug eluting matrix, such as silicone, and a prostaglandin or other therapeutic agent, in some embodiments, latanoprost, wherein the therapeutic agent is impregnated in part or all of implant body, such as those described in U.S. application Ser. No. 10/825,047 (filed Apr. 15, 2004 and entitled Drug Delivery via Punctal Plug). In some embodiments, the drug core comprises a latanoprost or other therapeutic agent(s) matrix comprising a pharmaceutically acceptable vehicle, for example, a non-bioabsorbable polymer, for example silicone in a non-homogenous mixture with the latanoprost or other therapeutic agent(s). The non-homogeneous mixture in the drug core may comprise a silicone matrix saturated with the latanoprost or other therapeutic agent(s) or with inclusions of latanoprost or other therapeutic agent(s). The inclusions in the drug core are a concentrated form of latanoprost or other therapeutic agent(s), and the silicone matrix encapsulates the inclusions in the drug core. In specific embodiments, the latanoprost or other therapeutic agent(s) inclusions encapsulated within the silicone matrix comprise an inhomogeneous mixture of the inclusions encapsulated within the silicone matrix. The drug core inclusions can comprise latanoprost oil.

It is also within the scope of this invention to modify or adapt the implant device to deliver a high release rate, a low release rate, a bolus release, a burst release, or combinations thereof. A bolus of the drug may be released by the formation of an erodable polymer cap that is immediately dissolved in the tear or tear film. As the polymer cap comes in contact with the tear or tear film, the solubility properties of the polymer enable the cap to erode and the latanoprost or other therapeutic agent(s) is released all at once. A burst release of latanoprost or other therapeutic agent(s) can be performed using a polymer that also erodes in the tear or tear film based on the polymer solubility. In this example, the drug and polymer may be stratified along the length of the device so that as the outer polymer layer dissolves, the drug is immediately released. A high or low release rate of the drug could be accomplished by changing the solubility of the erodable polymer layer so that the drug layer released quickly or slowly. Other methods to release the latanoprost or other therapeutic agent(s) could be achieved through porous membranes, soluble gels (such as those in typical ophthalmic solutions), microparticle encapsulations of the drug, or nanoparticle encapsulation.

Sheath Body:

The sheath body can comprise appropriate shapes and materials to control the migration of latanoprost or other therapeutic agent(s) from the drug core. In some embodiments, the sheath body houses the drug core and can fit snugly against the core. The sheath body is made from a material that is substantially impermeable to the latanoprost or other therapeutic agent(s) so that the rate of migration of latanoprost or other therapeutic agent(s) may be largely controlled by the exposed surface area of the drug core that is not covered by the sheath body. In many embodiments, migration of the latanoprost or other therapeutic agent(s) through the sheath body can be about one tenth of the migration of latanoprost or other therapeutic agent(s) through the exposed surface of the drug core, or less, often being one hundredth or less. In other words, the migration of the latanoprost or other therapeutic agent(s) through the sheath body is at least about an order of magnitude less that the migration of latanoprost or other therapeutic agent(s) through the exposed surface of the drug core. Suitable sheath body materials include polyimide, polyethylene terephthalate (hereinafter "PET"). In some embodiments, the sheath body has a thickness, as defined from the sheath surface adjacent the core to the opposing sheath surface away from the core, from about 0.00025" to about 0.0015". In some embodiments, the total diameter of the sheath that extends across the core ranges from about 0.2 mm to about 1.2 mm. The core may be formed by dip coating the core in the sheath material. Alternatively or in combination, the sheath body can comprise a tube and the core introduced into the sheath, for example as a liquid or solid that can be slid, injected or extruded into the sheath body tube. The sheath body can also be dip coated around the core, for example dip coated around a pre-formed core.

The sheath body can be provided with additional features to facilitate clinical use of the implant. For example, the sheath may receive a drug core that is exchangeable while the implant body, retention structure and sheath body remain implanted in the patient. The sheath body is often rigidly attached to the retention structure as described above, and the core is exchangeable while the retention structure retains the sheath body. In specific embodiments, the sheath body can be provided with external protrusions that apply force to the sheath body when squeezed and eject the core from the sheath body. Another drug core can then be positioned in the sheath body. In many embodiments, the sheath body or retention structure may have a distinguishing feature, for example a distinguishing color, to show placement such that the placement of the sheath body or retention structure in the canaliculus or other body tissue structure can be readily detected by the patient. The retention element or sheath body may comprise at least one mark to indicate the depth of placement in the canaliculus such that the retention element or sheath body can be positioned to a desired depth in the canaliculus based on the at least one mark.

Retention Structure:

In many embodiments, a retention structure is employed to retain the implant in the punctum or canaliculus. The retention structure is attached to or integral with the implant body. The retention structure comprises an appropriate material that is sized and shaped so that the implant can be easily positioned in the desired tissue location, for example, the punctum or canaliculus. In some embodiments, the drug core may be attached to the retention structure via, at least in part, the sheath. In some embodiments, the retention structure comprises a hydrogel configured to expand when the retention structure is placed in the punctum. The retention structure can comprise an attachment member having an axially oriented surface. In some embodiments, expansion of the hydrogel can urge against the axially oriented surface to retain the hydrogel while the hydrogel is hydrated. In some embodiments, the attachment member can comprise at least one of a protrusion, a flange, a rim, or an opening through a portion of the retention structure. In some embodiments, the retention structure includes an implant body portion size and shape to substantially match an anatomy of the punctum and canaliculus.

The retention structure may have a size suitable to fit at least partially within the canalicular lumen. The retention structure can be expandable between a small profile configuration suitable for insertion and a large profile configuration to anchor the retention structure in the lumen, and the retention structure can be attached near the distal end of the drug core. In specific embodiments, the retention structure can slide along the drug core near the proximal end when the retention structure expands from the small profile configuration to the large profile configuration. A length of the retention structure along the drug core can be shorter in the large profile configuration than the small profile configuration.

In some embodiments, the retention structure is resiliently expandable. The small profile may have a cross section of no more than about 0.2 mm, and the large profile may have a cross section of no more than about 2.0 mm. The retention structure may comprise a tubular body having arms separated by slots. The retention structure can be disposed at least partially over the drug core.

In some embodiments, the retention structure is mechanically deployable and typically expands to a desired cross sectional shape, for example with the retention structure comprising a super elastic shape memory alloy such as Nitinol™. Other materials in addition to Nitinol™ can be used, for example resilient metals or polymers, plastically deformable metals or polymers, shape memory polymers, and the like, to provide the desired expansion. In some embodiments polymers and coated fibers available from Biogeneral, Inc. of San Diego, Calif. may be used. Many metals such as stainless steels and non-shape memory alloys can be used and provide the desired expansion. This expansion capability permits the implant to fit in hollow tissue structures of varying sizes, for example canaliculae ranging from 0.3 mm to 1.2 mm (i.e. one size fits all). Although a single retention structure can be made to fit canaliculae from 0.3 to 1.2 mm across, a plurality of alternatively selectable retention structures can be used to fit this range if desired, for example a first retention structure for canaliculae from 0.3 to about 0.9 mm and a second retention structure for canaliculae from about 0.9 to 1.2 mm. The retention structure has a length appropriate to the anatomical structure to which the retention structure attaches, for example a length of about 3 mm for a retention structure positioned near the punctum of the canaliculus. For different anatomical structures, the length can be appropriate to provide adequate retention force, e.g. 1 mm to 15 mm lengths as appropriate.

Although the implant body may be attached to one end of the retention structure as described above, in many embodiments the other end of the retention structure is not attached to the implant body so that the retention structure can slide over the implant body including the sheath body and drug core while the retention structure expands. This sliding capability on one end is desirable as the retention structure may shrink in length as the retention structure expands in width to assume the desired cross sectional width. However, it should be noted that many embodiments may employ a sheath body that does not slide in relative to the core.

In many embodiments, the retention structure can be retrieved from tissue. A projection, for example a hook, a loop, or a ring, can extend from a portion of the implant body to facilitate removal of the retention structure.

In some embodiments the sheath and retention structure can comprise two parts.

Occlusive Element:

An occlusive element can be mounted to and expandable with the retention structure to inhibit tear flow. An occlusive element may inhibit tear flow through the lumen, and the occlusive element may cover at least a portion of the retention structure to protect the lumen from the retention structure. The occlusive element comprises an appropriate material that is sized and shaped so that the implant can at least partially inhibit, even block, the flow of fluid through the hollow tissue structure, for example lacrimal fluid through the canaliculus. The occlusive material may be a thin walled membrane of a biocompatible material, for example silicone, that can expand and contract with the retention structure. The occlusive element is formed as a separate thin tube of material that is slid over the end of the retention structure and anchored to one end of the retention structure as described above. Alternatively, the occlusive element can be formed by dip coating the retention structure in a biocompatible polymer, for example silicone polymer. The thickness of the occlusive element can be in a range from about 0.01 mm to about 0.15 mm, and often from about 0.05 mm to 0.1 mm.

Drug Core:

In some embodiments, the drug core may be inserted into an implant body, or may serve as the implant itself, without any additional structural components, or may be configured to adopt the shape of a punctal plug or the like. The drug core comprises latanoprost or other therapeutic agent(s) and materials to provide sustained release of the latanoprost or other therapeutic agent(s). In some embodiments, the drug core comprises a sustained release formulation, which formulation consists of or consists essentially of latanoprost or other therapeutic agent(s) and silicone as a carrier. The latanoprost or other therapeutic agent(s) migrates from the drug core to the target tissue, for example ciliary muscles of the eye. The drug core may optionally comprise latanoprost or other therapeutic agent(s) in a matrix, wherein the latanoprost or other therapeutic agent(s) is dispersed or dissolved within the matrix. The latanoprost or other therapeutic agent(s) may be only slightly soluble in the matrix so that a small amount is dissolved in the matrix and available for release from the surface of the drug core. As the latanoprost or other therapeutic agent(s) diffuses from the exposed surface of the core to the tear or tear film, the rate of migration from the core to the tear or tear film can be related to the concentration of latanoprost or other therapeutic agent(s) dissolved in the matrix. In addition or in combination, the rate of migration of latanoprost or other therapeutic agent(s) from the core to the tear or tear film can be related to properties of the matrix in which the latanoprost or other therapeutic agent(s) is dissolved.

In an embodiment, the topical formulation or the drug core does not contain a preservative. Preservatives include, for example, benzalkonium chloride and EDTA. In an embodiment, the implants of the invention may be less allergenic and may reduce chemical sensitivity compared to formulations containing these preservatives.

In specific embodiments, the rate of migration from the drug core to the tear or tear film can be based on a silicone formulation. In some embodiments, the concentration of latanoprost or other therapeutic agent(s) dissolved in the drug core may be controlled to provide the desired rate of release of the latanoprost or other therapeutic agent(s). The latanoprost or other therapeutic agent(s) included in the core can include liquid (such as oil), solid, solid gel, solid crystalline, solid amorphous, solid particulate, or dissolved forms of latanoprost or other therapeutic agent(s). In a some embodiments, the drug core may comprise liquid or solid inclusions, for example liquid Latanoprost or other therapeutic agent(s) droplets dispersed in the silicone matrix.

Table 1 shows drug insert silicones that may be used and associated cure properties, according to embodiments of the present invention. The drug core insert matrix material can include a base polymer comprising dimethyl siloxane, such as MED-4011, MED 6385 and MED 6380, each of which is commercially available from NuSil. The base polymer can be cured with a cure system such as a platinum-vinyl hydride cure system or a tin-alkoxy cure system, both commercially available from NuSil. In many embodiments, the cure system may comprise a known cure system commercially available for a known material, for example a known platinum vinyl hydride cure system with known MED-4011. In a specific embodiment shown in Table 1, 90 parts of MED-4011 can be combined with 10 parts of the crosslinker, such that the crosslinker comprises 10% of the mixture. A mixture with MED-6385 may comprise 2.5% of the crosslinker, and mixtures of MED-6380 may comprise 2.5% or 5% of the crosslinker.

TABLE 1

Drug Insert Silicone Selections

| Material | Base Polymer | Cure System | Crosslinker Percent |
| --- | --- | --- | --- |
| MED-4011 | Dimethyl siloxane Silica filler material | Platinum vinyl hydride system 10% | 10% |
| MED-6385 | Dimethyl siloxane Diatomaceous earth filler material | Tin-Alkoxy 2.5% | 2.5% |
| MED-6380 | Dimethyl siloxane without filler material | Tin-Alkoxy | 2.5 to 5% |

It has been determined according to the present invention that the cure system and type of silicone material can affect the curing properties of the solid drug core insert, and may potentially affect the yield of therapeutic agent from the drug core matrix material. In specific embodiments, curing of MED-4011 with the platinum vinyl hydride system can be inhibited with high concentrations of drug/prodrug, for example over 20% drug, such that a solid drug core may not be formed. In specific embodiments, curing of MED-6385 or MED 6380 with the tin alkoxy system can be slightly inhibited with high concentrations, e.g. 20%, of drug/prodrug. This slight inhibition of curing can be compensated by increasing the time or temperature of the curing process. For example, embodiments of the present invention can make drug cores comprising 40% drug and 60% MED-6385 with the tin alkoxy system using appropriate cure times and temperatures. Similar results can be obtained with the MED-6380 system the tin-alkoxy system and an appropriate curing time or temperature. Even with the excellent results for the tin alkoxy cure system, it has been determined according to the present invention that there may be an upper limit, for example 50% drug/prodrug or more, at which the tin-alkoxy cure system may not produce a solid drug core. In many embodiments, the latanoprost or other therapeutic agent(s) in the solid drug core may be at least about 5%, for example a range from about 5% to 50%, and can be from about 20% to about 40% by weight of the drug core.

The drug core or other agent supply (e.g., implant impregnated body) can comprise one or more biocompatible materials capable of providing sustained release of latanoprost or other therapeutic agent(s). Although the drug core is described above with respect to an embodiment comprising a matrix with a substantially non-biodegradable silicone matrix with inclusions of latanoprost or other therapeutic agent(s) located therein that dissolve, the drug core can include structures that provide sustained release of latanoprost or other therapeutic agent(s), for example a biodegradable matrix, a porous drug core, liquid drug cores and solid drug cores.

A matrix that contains latanoprost or other therapeutic agent(s) can be formed from either biodegradable or non-biodegradable polymers. A non-biodegradable drug core can include silicone, acrylates, polyethylenes, polyurethane, polyurethane, hydrogel, polyester (e.g., DACRON™ from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY™ from Elgin Specialty Metals, Elgin, Ill.; CONICHROME™ from Carpenter Metals Corp., Wyomissing, Pa.).

A biodegradable drug core can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some embodiments the drug core can comprise at least one hydrogel polymer.

Specific Implant Embodiments

Various embodiments of the implant that may be employed in the methods described herein are as follows (see also the Example section below). In some embodiments, the drug insert includes a thin-walled polyimide tube sheath body that is filled with latanoprost or other therapeutic agent(s) dispersed in Nusil 6385, a cured medical grade solid silicone. The cured silicone serves as the solid, non-erodible matrix from which latanoprost or other therapeutic agent(s) slowly elutes. The drug insert is sealed at the distal end with a cured film of solid Loctite 4305 medical grade adhesive (cyanoacrylate). The polyimide tube sheath body is inert and, together with the adhesive, provides structural support and a barrier to both lateral drug diffusion and drug diffusion through the distal end of the drug insert. The drug insert is seated in the bore of the punctal implant and is held in place via an interference fit. In some embodiments, a body of the implant is at least partially impregnated with a therapeutic agent, such as latanoprost or other therapeutic agent(s).

Figure 2A:
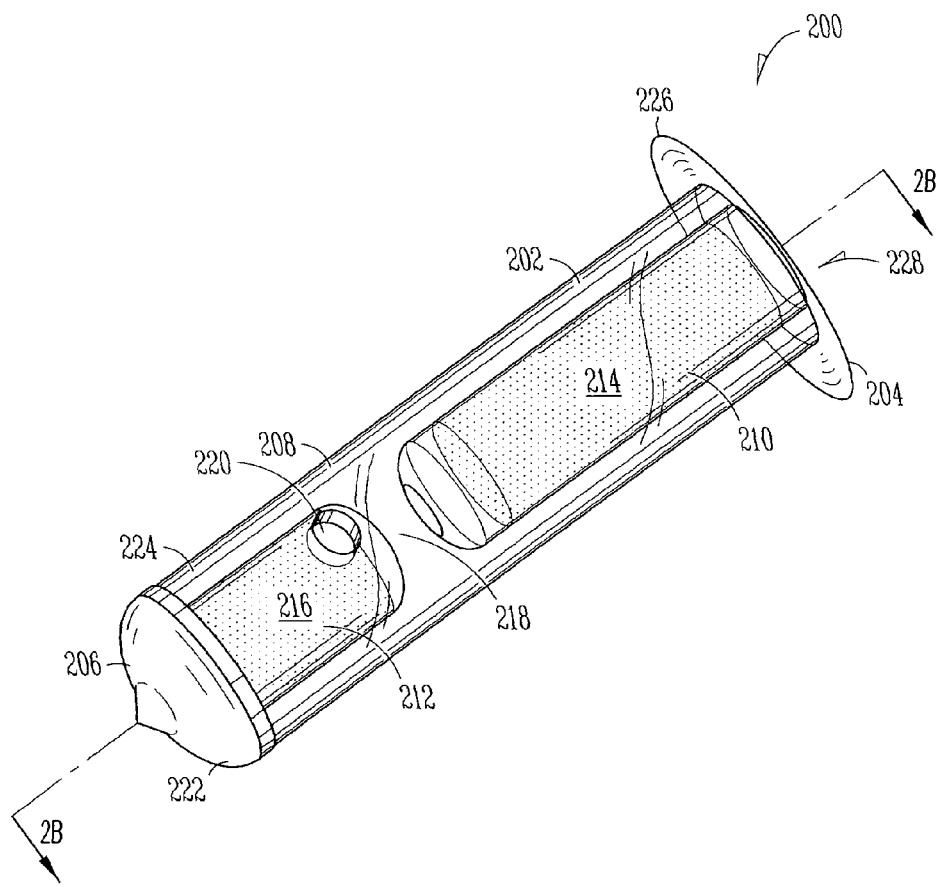
FIG. 2A illustrates an example of an isometric view of a punctal implant configured to be retained at least partially within a lacrimal punctum or canalicular anatomy.

FIG. 2A illustrates an example embodiment of a punctal implant 200 that is insertable into a lacrimal punctum. The insertion of the punctal implant 200 into the lacrimal punctum allows for one or more of inhibition or blockage of tear flow therethrough (e.g., to treat dry eyes) or the sustained delivery of a therapeutic agent to an eye (e.g., to treat one or more of infection, inflammation, glaucoma or other ocular diseases). In this embodiment, the punctal implant 200 comprises an implant body 202 extending from a proximal end portion 204 to a distal end portion 206 and having a retention structure 208.

In various embodiments, the implant body 202 can comprise an elastic material, such as silicone, polyurethane or other urethane-based material, or an acrylic of a non-biodegradable, partially biodegradable or biodegradable nature (i.e., erodeable within the body) allowing at least one portion of the retention structure to deform outward. In some embodiments, the biodegradable elastic materials include cross-linked polymers, such as poly (vinyl alcohol). In some embodiments, different portions of the implant body 202 are made of different materials. For instance, the implant body proximal end portion 204 can comprise a silicone/polyurethane co-polymer and the implant body distal end portion 206 can comprise a polyurethane hydrogel or other solid hydrogel. In certain embodiments, the implant body proximal end portion 204 can comprise silicone and the implant body distal end portion 206 can comprise a hydrophilic silicone mixture. Other co-polymers that can be used to form the implant body 302 include silicone/urethane, silicone/poly(ethylene glycol) (PEG), and silicone/2hydroxyethyl methacrylate (HEMA).

In certain embodiments, the implant body 202 can include a cylindrical-like structure having a first chamber 210 at or near the proximal end and a second chamber 212 at or near the distal end. A latanoprost or other therapeutic agent(s) drug core 214 can be disposed in the first chamber 210, while a hydrogel or other expandable retention element 216 of a biodegradable or non-biodegradable nature can be disposed in the second chamber 216. In some embodiments, the biodegradable retention elements include salt and cellulose based mixtures. In some embodiments, the non-biodegradable retention elements include hydrogels or other synthetic polymers. An implant body septum 218 can be positioned between the first chamber 210 and the second chamber 216 and can be used to inhibit or prevent communication of a material between the drug core 214 and the hydrogel retention element 216.

In various ways, the expandable, hydrogel retention element 216 can be substantially encapsulated, such as within a portion of the retention structure 208. In various embodiments, the retention structure 208 can include a fluid permeable retainer allowing fluid to be received into and absorbed or otherwise retained by the hydrogel retention element 216, such as upon its insertion into the punctum. The hydrogel retention element 216 can be configured to expand, such as to a size or shape that urges one or more outer surface portions of the retention structure 208 to contact a wall of the lacrimal canaliculus, thereby retaining or helping retain a least a portion of the punctal implant within the punctum. In some embodiments, the fluid permeable retainer can include a fluid permeable aperture 220, such as disposed in a lateral wall of the retention structure 208. In some embodiments, the fluid permeable retainer can include a fluid permeable or hydrophilic cap member 222 or other membrane. In some embodiments, the fluid permeable retainer can include a fluid permeable or hydrophilic implant body portion 224. These examples of fluid permeable retainers 220, 222, and 224 can also inhibit the hydrogel retention element 216 from appreciably protruding out of the retention structure 208 during and upon expansion.

The implant body 202 can include a feedback or other projection 226, such as extending laterally at least partially from or around (e.g., a removal loop) a proximal end portion 204 of the implant body 202. In some embodiments, the projection 226 can include a removal loop. In some embodiments, the projection 226 can be configured to seat against or near (e.g., via a ramped portion 260) the punctum opening, such as for inhibiting or preventing the punctal implant 200 from passing completely within the canaliculus, or for providing tactile or visual feedback information to an implanting user regarding the same. In some embodiments, a proximal end of the projection 226 can include a convex such as for helping provide comfort to a patient when implanted. In some embodiments, the projection 226 can include a convex radius of about 0.8 millimeters. In some embodiments, the projection 226 is between about 0.7 millimeters to about 0.9 millimeters in diameter. In some embodiments, the projection 226 can include a non-concave shape of about 0.5 millimeters to about 1.5 millimeters in diameter, and 0.1 millimeters to about 0.75 millimeters in thickness. In some embodiments, the projection 226 has a wing-like shape, in which a column-like projection extends from opposite sides of the implant body proximal end 204. In some examples, the projection 226 includes a partially trimmed head portion extending 360 degrees around the proximal end 204 from an outer implant body surface. In some examples, such the projection 226 includes a full head portion extending 360 degrees around the proximal end 204 from an outer implant body surface. In an example, the projection 226 includes a cross-sectional shape similar to a flat disk (i.e., relatively flat top and bottom surfaces). A drug or other agent elution port 228 can extend though the projection 226, such as to provide sustained release of a drug core 214 agent onto an eye.

Figure 2B:
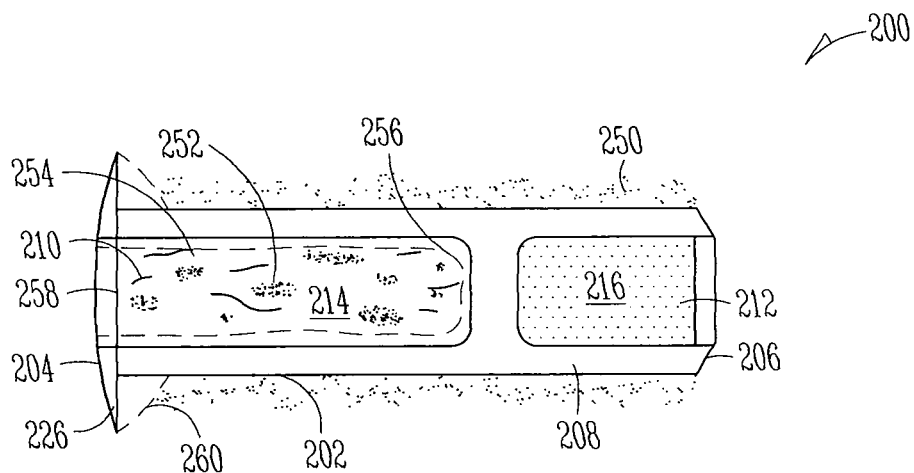
FIG. 2B illustrates an example of a cross-sectional view of a punctal implant taken along a line parallel to a longitudinal axis of the implant, such as along line 2B-2B of FIG. 2A.

FIG. 2B illustrates a cross-sectional view of an example embodiment of a punctal implant 200 taken along a line parallel to a longitudinal axis of the implant, such as along line 2B-2B of FIG. 2A. As shown in FIG. 2B, the punctal implant can include an implant body 202 having a retention structure 208 substantially encapsulating a hydrogel retention element 216 at or near an implant body distal end portion 206, and a latanoprost or other therapeutic agent(s) drug core 214 disposed within the implant body, for example at or near a proximal end portion 204. In this embodiment, the drug core 214 is disposed in a first implant body chamber 210 and the hydrogel retention element 216 is disposed in a second implant body chamber 212. As discussed above, the hydrogel retention element 216 can be configured to expand to a size or shape that retains or helps retain at least a portion of the implant 200 within the lacrimal punctum. In some embodiments, a hydrogel retention element 250 can also be coated or otherwise provided on an outer surface portion of the implant body 202 providing another (e.g., secondary) mechanism for retaining or helping to retain at least a portion of the implant 200 at least partially within the lacrimal punctum.

The retention structure 208, which can be used to substantially encapsulate the hydrogel retention element 216, can be of varying sizes relative to an implant body 202 size. In some embodiments, the retention structure 208 is at least about one fifth the length of the implant body 202. In some embodiments, the retention structure 208 is at least about one fourth the length of the implant body 202. In some embodiments, the retention structure 208 is at least about one third the length of the implant body 202. In some embodiments, the retention structure 208 is at least about one half the length of the implant body 202. In some embodiments, the retention structure 208 is at least about three quarters the length of the implant body 202. In some embodiments, the retention structure 208 is about the full length of the implant body 202.

As shown in the example embodiment of FIG. 2B, the hydrogel retention element 216 can have a non-expanded, "dry" state, which aids insertion through the punctum and into the lacrimal canaliculus. Once placed in the canaliculus, the hydrogel retention element 216 can absorb or otherwise retain canalicular or other fluid, such as via a fluid permeable retainer 220, 222, 224 (FIG. 2A) to form an expanded structure. In some embodiments, the hydrogel retention element 216 can include a material that is non-biodegradable. In some embodiments, the hydrogel retention element 216 can include a material that is biodegradable. Other options for the hydrogel retention element 216 can also be used. For instance, the hydrogel retention element 216 can be molded with the retention structure 208 in a single piece, or can be formed separately as one piece and subsequently coupled to the retention structure 208.

In some examples, the drug core 214 disposed at or near the proximal end portion 204 of the implant body 202 can include a plurality of latanoprost or other therapeutic agent(s) inclusions 252, which can be distributed in a matrix 254. In some embodiments, the inclusions 252 comprise a concentrated form of the latanoprost or other therapeutic agent(s) (e.g., a crystalline agent form). In some embodiments, the matrix 254 can comprise a silicone matrix or the like, and the distribution of inclusions 252 within the matrix can be non-homogeneous. In some embodiments, the agent inclusions 252 include droplets of an oil, such as latanoprost oil. In still other embodiments, the agent inclusions 252 comprise solid particles. The inclusions can be of many sizes and shapes. For instance, the inclusions can be microparticles having dimensions on the order of about 1 micrometers to about 100 micrometers.

In the embodiment shown, the drug core 214 has a sheath body 256 disposed over at least a portion thereof such as to define at least one exposed surface 258 of the drug core. The exposed surface 258 can be located at or near the proximal end portion 204 of the implant body such as to contact a tear or a tear film fluid and release the latanoprost or other therapeutic agent(s) at one or more therapeutic levels over a sustained time period when the punctal implant 200 is inserted into the punctum.

Figure 2C:
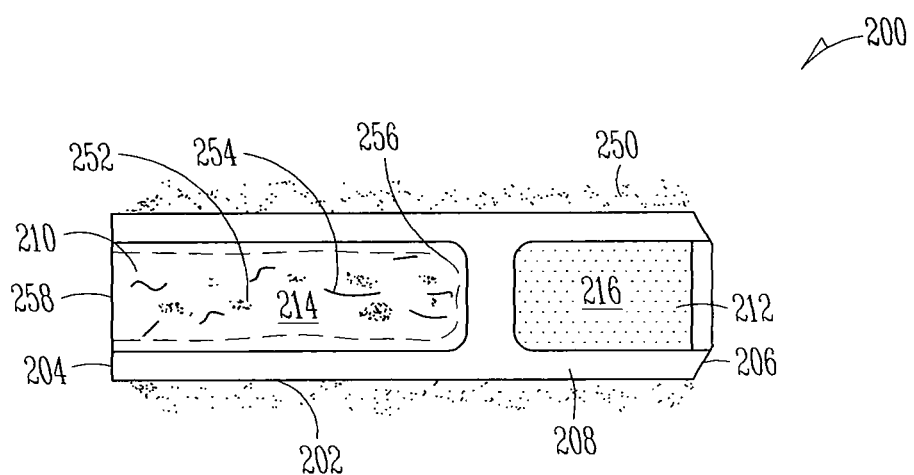
FIG. 2C illustrates an example of a cross-sectional view of another punctal implant taken along a line parallel to a longitudinal axis of the implant.

FIG. 2C illustrates a cross-sectional view of an example embodiment of a punctal implant 200 taken along a line parallel to a longitudinal axis of the implant. As shown in FIG. 2C, the punctal implant includes an implant body 202 without a feedback or other projection 226 (FIG. 2A). In this way, the implant 200 can be completely inserted inside the lacrimal punctum. In some embodiments, the first chamber 210 can include dimensions of about 0.013 inches×about 0.045 inches. In some embodiments, the second chamber 212 can include dimensions of about 0.013 inches by about 0.020 inches.

Figure 3A:
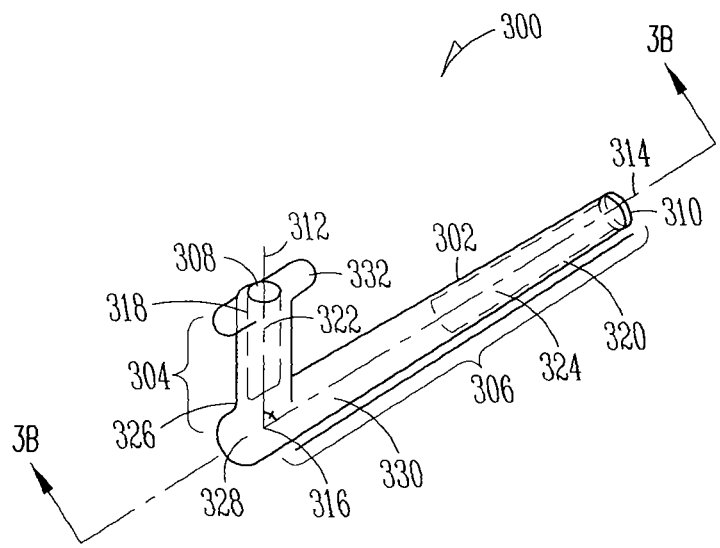
FIG. 3A illustrates an example of an isometric view of a punctal implant configured to be retained at least partially within a lacrimal punctum or canalicular anatomy.

FIG. 3A illustrates another embodiment of a punctal implant 300 that can be insertable into a lacrimal punctum. The insertion of the punctal implant 300 into the lacrimal punctum can allow for one or more of: inhibition or blockage of tear flow therethrough (e.g., to treat dry eyes) or the sustained delivery of a therapeutic agent to an eye (e.g., to treat an infection, inflammation, glaucoma or other ocular disease or disorder), a nasal passage (e.g., to treat a sinus or allergy disorder) or an inner ear system (e.g., to treat dizziness or a migraine).

In this embodiment, the punctal implant 300 comprises an implant body 302 including first 304 and second 306 portions. The implant body 302 extends from a proximal end 308 of the first portion 304 to a distal end 310 of the second portion 306. In various embodiments, the proximal end 308 can define a longitudinal proximal axis 312 and the distal end 310 can define a longitudinal distal axis 314. The implant body 300 can be configured such that, when implanted, an at least 45 degree angled intersection 316 exists between the proximal axis 312 and the distal axis 314 for biasing at least a portion of the implant body 302 against at least a portion of a lacrimal canaliculus located at or more distal to a canaliculus curvature. In some embodiments, the implant body 302 can be configured such that the angled intersection 316 is between about 45 degrees and about 135 degrees. In this embodiment, the implant body 302 is configured such that the angled intersection 316 is approximately about 90 degrees. In various embodiments, a distal end 326 of the first portion 304 can be integral with the second portion 306 at or near a proximal end 328 of the second portion 306.

In certain embodiments, the implant body 302 can include angularly disposed cylindrical-like structures comprising one or both of a first cavity 318 disposed near the proximal end 308 or a second cavity 320 disposed near the distal end 310. In this embodiment, the first cavity 318 extends inward from the proximal end 308 of the first portion 304, and the second cavity 320 extends inward from the distal end 310 of the second portion 306. A first drug-releasing drug supply 322 can be disposed in the first cavity 318 to provide a sustained drug release to an eye, while a second drug-releasing or other agent-releasing drug supply 324 can be disposed in the second cavity 320 to provide a sustained drug or other agent release to a nasal passage or inner ear system, for example. An implant body septum 330 can be positioned between the first cavity 318 and the second cavity 320, and can be used to inhibit or prevent communication of a material between the first drug supply 322 and the second drug supply 324.

In some embodiments, the drug or other agent release can occur, at least in part, via an exposed surface of the drug supply 322, 324. In some embodiments, by controlling geometry of the exposed surface, a predetermined drug or agent release rate can be achieved. For instance, the exposed surface can be constructed with a specific geometry or other technique appropriate to control the release rate of the drug or other agent onto an eye, such as on an acute basis, or on a chronic basis between outpatient doctor visits, for example. Further description regarding effective release rates of one or more drugs or other agents from a drug supply 322, 324 can be found in commonly-owned DeJuan et al., U.S. application Ser. No. 11/695,545 (filed Apr. 2, 2007 and entitled Nasolacrimal Drainage System Implants for Drug Therapy) which is herein incorporated by reference in its entirety, including its description of obtaining particular release rates. In some embodiments, the exposed surface of the drug supply 322, 324 can be flush or slightly below the proximal end 308 of the first portion 304 or the distal end 310 of the second portion 306, respectively, such that the drug supply does not protrude outside of the implant body 302. In some embodiments, the exposed surface of the drug supply 322, for instance, can be positioned above the proximal end 308 such that the drug supply 322 at least partially protrudes outside of the implant body 302.

The implant body 302 can include an integral feedback or other projection 332, such as projections extending laterally at least partially from or around a proximal end 308 of the first implant body portion 304. In some embodiments, the projection 332 can include a set of wings for use in removing the punctal implant 300 from an implant position. The removal set of wings can be configured without migration in mind, as the non-linear configuration of the implant body 302 can prevent migration by assuming a size or shape of the canaliculus curvature and optionally, the lacrimal canaliculus ampulla. In some embodiments, the projection 332 can be configured to seat against or near the punctal opening such as for inhibiting or preventing the punctal implant 300 from passing completely within the lacrimal canaliculus, or for providing tactile or visual feedback information to an implanting user, e.g., as to whether the implant is fully implanted. The projection 332 can extend laterally in a direction parallel to or away from an eye when implanted. This will reduce irritation to the eye as compared to a case in which a portion of the projection extends toward the eye.

In addition, a lateral extension direction of the projection 332 from the proximal end 308 can be substantially the same as a lateral extension direction of the second implant body portion 306 relative to the distal end 326 of the first implant body portion 304. This can also avoid extension toward the eye. A drug or other agent elution port can extend though a head portion-projection 332, such as to provide sustained release of the drug supply 322 agent onto an eye.

In various embodiments, the implant body 302 can be molded using an elastic material, such as silicone, polyurethane, NuSil (e.g., NuSil 4840 with 2% 6-4800) or an acrylic of a non-biodegradable, partially biodegradable or biodegradable nature (i.e., erodeable within the body) allowing a non-linear extending implant body 302 to be formed. In some embodiments, the biodegradable elastic materials can include cross-linked polymers, such as poly (vinyl alcohol). In some embodiments, the implant body 302 can comprise a silicone/polyurethane co-polymer. Other co-polymers that can be used to form the implant body 302 include, but are not limited to, silicone/urethane, silicone/poly (ethylene glycol) (PEG), and silicone/2hydroxyethyl methacrylate (HEMA). As discussed in commonly-owned Jain et al., Application Ser. No. 61/049,317 (filed Apr. 30, 2008 and entitled Drug-Releasing Polyurethane Lacrimal Insert), which is herein incorporated by reference in its entirety, urethane-based polymer and copolymer materials allow for a variety of processing methods and bond well to one another.

Figure 3B:
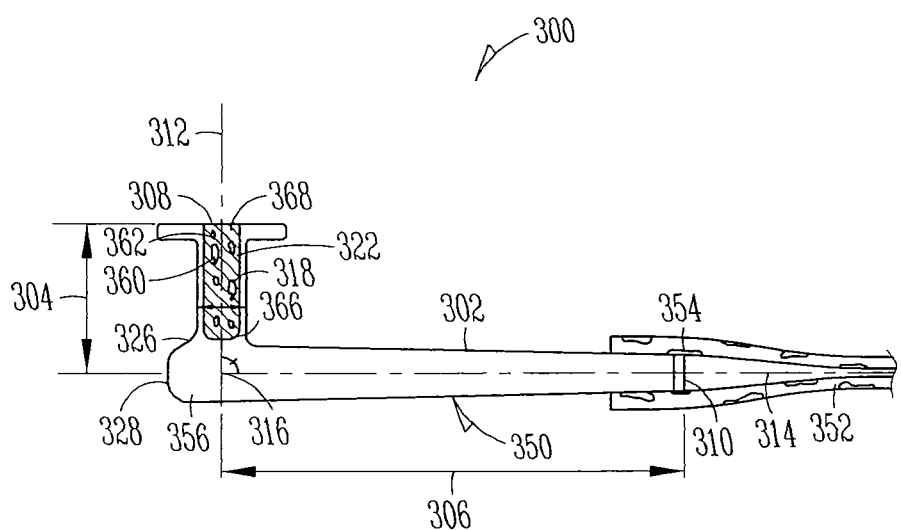
FIG. 3B illustrates an example of a cross-sectional view of a punctal implant taken along a line parallel to a longitudinal axis of the implant, such as along line 3B-3B of FIG. 3A, and a dilation of an implant-receiving anatomical tissue structure.

FIG. 3B illustrates an example embodiment of a cross-sectional view of a punctal implant 300 taken along a line parallel to a longitudinal axis of the implant, such as along line 3B-3B of FIG. 3A. As shown in FIG. 3B, the punctal implant 300 can include an implant body 302 including first 304 and second 306 portions. The implant body 302 extends from a proximal end 308 of the first portion 304 to a distal end 310 of the second portion 306. In various embodiments, the proximal end 308 can defines a longitudinal proximal axis 312 and the distal end 310 can define a longitudinal distal axis 314. The implant body 300 can be configured such that, when implanted, an at least 45 degree angled intersection 316 exists between the proximal axis 312 and the distal axis 314 for biasing at least a portion of the implant body 302 against at least a portion of a lacrimal canaliculus located at or more distal to a canaliculus curvature. In this embodiment, the implant body 300 is configured such that the angled intersection 316 is approximately about 90 degrees.

In various embodiments, a distal end 326 of the first portion 304 can be integral with the second portion 306 at or near a proximal end 328 of the second end 326. In some embodiments, the second portion 306 can include a length having a magnitude less than four times a length of the first portion 304. In one embodiment, the second portion 306 can include a length of less than about 10 millimeters, such as is shown in FIG. 3B. In another embodiment, the second portion 306 can include a length less than about 2 millimeters.

In certain embodiments, the second portion 306 can comprise an integral dilator 350 to dilate anatomical tissue 352, such one or both of a lacrimal punctum or canaliculus to a sufficient diameter as the punctal implant 300 is being implanted. In this way, the punctal implant 300 can be implanted in various size ocular anatomies without the need for pre-dilation via a separate enlarging tool. The dilator 350 can be formed so as to not be traumatic to an inner lining of the punctum and the canaliculus. In some embodiments, a lubricious coating disposed on, or impregnated in, an outer surface of the implant body 302 can be used to further aid insertion of the punctal implant 300 into the anatomical tissue 352. In one embodiment, the lubricious coating can include a silicone lubricant.

As shown, the dilator 350 can generally narrow from a location near the proximal end 328 of the second portion 306 to the distal end 310 of the second portion 306, such as from a diameter of about 0.6 millimeters to a diameter of about 0.2 millimeters. In some embodiments, an outer surface slope of the dilator 350, as measured from the location near the proximal end 328 of the second portion 306 to the distal end 310 of the second portion 306, can be between about 1 degree and about 10 degrees (e.g., 2 degrees, 3 degrees, 4 degrees, or 5 degrees) with respect to the longitudinal distal axis 314. In some embodiments, the slope of the dilator 350 can be less than 45 degrees with respect to the longitudinal distal axis 314. Among other factors, a determination of a desirable dilator 350 slope for a given implant situation can be made by balancing an implant body 302 strength desirable for implant with a desire to have a soft, flexible and conforming implant body (e.g., to conform to a lacrimal canaliculus anatomy) upon implantation. In some embodiments, a diameter of a dilator tip 354 can be between about 0.2 millimeters and about 0.5 millimeters.

In certain embodiments, the proximal end 328 of the second implant body portion 306 can include a lead extension 356 configured to bias against at least a portion of a lacrimal canaliculus ampulla when implanted. In this embodiment, the lead extension 356 projects proximally from the intersection between the first 304 and second 306 implant body portions, such as in an opposite direction as the extension of the dilator 350.

In certain embodiments, the implant body 302 can include a first cavity 318 disposed near the proximal end 308. In this embodiment, the first cavity 318 extends inward about 2 millimeters or less from the proximal end 308, and houses a first drug-releasing or other agent-releasing drug supply 322 to provide a sustained drug or other agent release to an eye. In some embodiments, the drug supply 322 can include a plurality of therapeutic agent inclusions 360, which can be distributed in a matrix 362. In some embodiments, the inclusions 360 can comprise a concentrated form of the therapeutic agent (e.g., a crystalline agent form). In some embodiments, the matrix 362 can comprise a silicone matrix or the like, and the distribution of inclusions 360 within the matrix can be non-homogeneous. In some embodiments, the agent inclusions 360 can include droplets of oil, such as latanoprost oil. In still other embodiments, the agent inclusions 360 can comprise solid particles, such as Bimatoprost particles in crystalline form. The inclusions can be of many sizes and shapes. For instance, the inclusions can include microparticles having dimensions on the order of about 1 micrometer to about 100 micrometers.

In the embodiment shown, the drug supply 322 includes a sheath body 366 disposed over at least a portion thereof such as to define at least one exposed surface 368 of the drug supply. The exposed surface 368 can be located at or near the proximal end 308 of the implant body 302 such as to contact a tear or a tear film fluid and release the therapeutic agent at one or more therapeutic levels over a sustained time period when the punctal implant 300 is inserted into the lacrimal punctum.

Figure 4A:
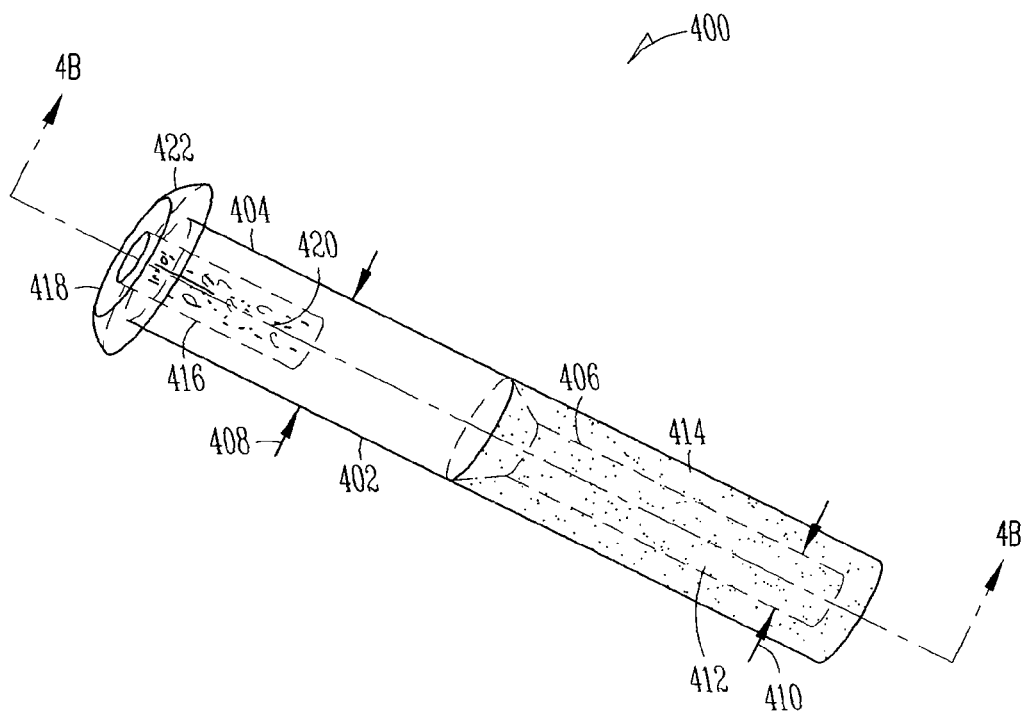
FIG. 4A illustrates an example of an isometric view of a punctal implant configured to be retained at least partially within a lacrimal punctum or canalicular anatomy.

FIG. 4A illustrates an embodiment of a punctal implant 400 that can be insertable into a lacrimal punctum. In various embodiments, the punctal implant 400 comprises an implant body 402, including first 404 and second 406 portions, which is sized and shaped for at least partial insertion into a lacrimal punctum. The first portion 404 is formed from a polymer and includes a first diameter 408. The second portion 406 is also formed from a polymer and includes a base member 412 (e.g., mandrel or spine-like member) having a second diameter 410, which is less than the first diameter 408. In an embodiment, the first 404 and second 406 portions are integrally coupled and comprise a unitary implant body 402. In an embodiment, the first 404 and second 406 portions are separate elements, which can be coupled to one another via an engagement between a coupling void and a coupling arm, for instance.

An expandable retention member 414, such as a swellable material, can be bonded or otherwise coupled over the base member 412 such that it envelops, at least in part, a portion of the base member 412. In an embodiment, the expandable retention member substantially envelops the base member 412. As the expandable retention member 414 absorbs or otherwise retains lacrimal or other fluid, such as upon insertion into a lacrimal punctum, its size increases and its shape may change thereby urging itself against and slightly biasing a wall of the associated canaliculus. It is believed that the expandable retention member 414 will provide retention comfort to a subject and may improve punctal implant 400 implant retention via controlled biasing of the canaliculus wall.

The positioning of the expandable retention member 414 over a portion of the implant body 402 allows the retention member 414 to be freely exposed to lacrimal fluid in situ, thereby allowing for a wide range of potential expansion rates. Further, the base member 412 provides an adequate coupling surface area to which the expandable retention member 414, for example, can adhere such that the material of the expandable retention member 414 does not remain in a lacrimal punctum after the punctal implant 400 is removed from the subject. As shown in this embodiment, the expandable retention member 414 can include a non-expanded, "dry or dehydrated" state, which aids insertion through a lacrimal punctum and into the associated lacrimal canaliculus. Once placed into a lacrimal canaliculus, the expandable retention member 414 can absorb or other retain lacrimal fluid to form an expanded structure.

In some embodiments, the implant body 402 can include a cylindrical-like structure comprising a cavity 416 disposed near a proximal end 418 of the first portion 404. In this embodiment, the cavity 416 extends inward from the proximal end 418 and includes a first drug-releasing or other agent-releasing drug supply 420 to provide a sustained drug or other agent release to an eye. The drug or other agent release can occur, at least in part, via an exposed surface of the drug supply 420. In an embodiment, the exposed surface of the drug supply 420 can be positioned above the proximal end 418 such that the drug supply 420 at least partially protrudes outside of the implant body 402. In some embodiments, the exposed surface of the drug supply 420 can be flush or slightly below the proximal end 418 such that the drug supply 420 does not protrude outside of the implant body 402.

In some embodiments, by controlling geometry or a drug concentration gradient near the exposed surface, a predetermined drug or agent release rate can be achieved. For instance, the exposed surface can be constructed with a specific geometry or other technique appropriate to control the release rate of the drug or other agent onto an eye, such as on an acute basis, or on a chronic basis between outpatient doctor visits, for example.

The implant body 402 can include an integral feedback or other projection 422, such as projections extending laterally at least partially from or around the proximal end 418 of the first implant body portion 404. In an embodiment, the projection 422 includes a partially trimmed head portion extending 360 degrees around the proximal end 418 from an outer implant body surface. In an embodiment, the projection 422 includes a full head portion extending 360 degrees around the proximal end 418 from an outer implant body surface. In an embodiment, the projection 422 includes a cross-sectional shape similar to a flat disk (i.e., relatively flat top and bottom surfaces). In various embodiments, the projection 422 can be configured to seat against or near a punctal opening when the second portion 406 of the implant body 402 is positioned within the associated canalicular lumen, such as for inhibiting or preventing the punctal implant 400 from passing completely within the canalicular lumen, for providing tactile or visual feedback information to an implanting user (e.g., as to whether the implant is fully implanted), or for removing the punctal implant 400 from an implant position. In an embodiment, the projection 422 includes a portion having a diameter of about 0.5-2.0 mm to prevent the punctal implant 400 from passing down into the canaliculus.

Figure 4B:
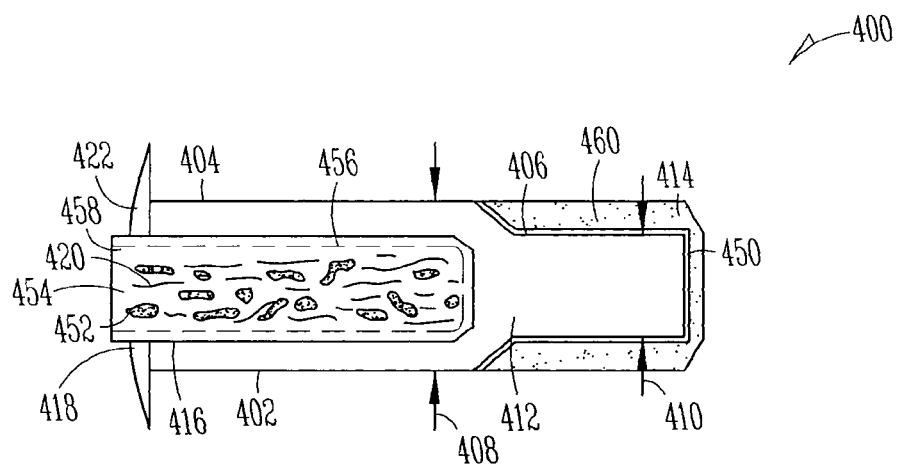
FIG. 4B illustrates an example of a cross-sectional view of a punctal implant taken along a line parallel to a longitudinal axis of the implant, such as along line 4B-4B of FIG. 4A.

FIG. 4B illustrates an example embodiment of a cross-sectional view of a punctal implant 400 taken along a line parallel to a longitudinal axis of the implant, such as along line 4B-4B of FIG. 4A. As shown in FIG. 4B, the punctal implant 400 comprises an implant body 402, including first 404 and second 406 portions, which is sized and shaped for at least partial insertion into a lacrimal punctum. The first portion 404 is formed from a polymer and includes a first diameter 408. The second portion 406 is also formed from a polymer and includes a base member 412 (e.g., mandrel or spine) having a second diameter 410, which is less than the first diameter 408. In an embodiment, the base member 412 is at least about one-third the total length of the implant body 402. In an embodiment, the base member 412 is at least about one-half the total length of the implant body 402. In the embodiment shown, the implant body 402 also includes an integral feedback or other projection 422, such as a projection extending laterally at least partially from or around a proximal end 418 of the first implant body portion 404.

In various embodiments, the implant body 402 can be molded or otherwise formed using an elastic material, such as silicone, polyurethane or other urethane-based material, or combinations thereof. In an embodiment, one or both of the first 404 and second 406 portions include a urethane-based material. In an embodiment, one or both of the first 404 and second 406 portions include a silicone-based material, such as 4840® or PurSil®. In an embodiment, one or both of the first 404 and second 406 portions include a copolymer material, such as polyurethane/silicone, urethane/carbonate, silicone/polyethylene glycol (PEG) or silicone/2hydroxyethyl methacrylate (HEMA). In various embodiments, the implant body 402 is configured to be non-absorbable in situ and is sufficiently strong to address issues of cutting strength (e.g., during insertion and removal of the punctal implant 400) and dimensional stability.

An expandable retention member 414, such as a swellable material, can be bonded or otherwise coupled over the base member 412 such that it envelops, at least in part, a portion of the base member 412. As the expandable retention member absorbs or otherwise retains lacrimal fluid, such as upon insertion into a lacrimal punctum, its size increases and its shape may change thereby urging itself against and slightly biasing a wall of the associated canaliculus. In various embodiments, the expandable retention member 414 can be molded or otherwise formed using a swellable material. In an embodiment, the expandable retention member 414 includes a polyurethane hydrogel, such as TG-2000®, TG-500®, or other urethane-based hydrogel. In an embodiment, the expandable retention member 414 includes a thermoset polymer, which may be configured to swell anisotropically. In an embodiment, the expandable retention member 414 includes a gel, which does not maintain its shape upon expansion, but rather conforms to fit the shape of a canaliculus lumen wall or other surrounding structure.

In some embodiments, the punctal implant 400 includes a base member 412 including polyurethane or other urethane-based material and an expandable retention member 414 including a polyurethane or other urethane-based swellable material. In an embodiments, a polyurethane hydrogel is coupled directly to an outer surface, such as a plasma-treated outer surface, of the base member 412.

In some embodiments, the punctal implant 400 includes an intermediate member 450 positioned between a portion of the implant body 402, such as the base member 412, and a portion of the expandable retention member 414. The intermediate member 450 can include a material configured to absorb, when implanted, a greater amount of lacrimal fluid than the polymer of the base member 412 but less lacrimal fluid than the swellable polymer of the expandable retention member 414. The intermediate member 450 can provide the punctal implant 400 with integrity, such as between a substantially non-swelling polymer of the implant body 402 and a swelling polymer of the expandable retention member 414. For instance, when the polymer of the expandable retention member 414 swells upon exposure to moisture, it is possible that the expanding polymer will, in the absence of the intermediate member 450, swell away from the underlying, non-swelling polymer of the base member 412. In an embodiment, the intermediate member 450 includes PurSil® and is dip or otherwise coated onto an outer surface of the base member 412. In an embodiment, the intermediate member 450 includes a polyurethane configured to absorb about 10% to about 500% water, such as Tecophilic® urethanes or Tecophilic® solution grade urethanes. Further discussion regarding the use of an intermediate member 450 positioned between a portion of a first polymer material and a portion of a second polymer material, typically different than the first polymer material, can be found in commonly-owned Sim et al., U.S. application Ser. No. 12/432,553 (filed Apr. 29, 2009 and entitled Composite Lacrimal Insert and Related Methods), which is herein incorporated by reference in its entirety.

In certain embodiments, the implant body 402 can include a cavity 416 disposed near the proximal end 418 of the first portion 404. In an embodiment, the first cavity 416 extends inward about 2 millimeters or less from the proximal end 418, and houses a first drug-releasing or other agent-releasing drug supply 420 to provide a sustained drug or other agent release to an eye. In an embodiment, the first cavity 416 extends through the implant body 402, and houses a first drug-releasing or other agent-releasing drug supply 420. In various embodiments, the drug supply 420 stores and slowly dispenses an agent to one or both of the eye or the nasolacrimal system as they are leached out, for example, by tear film fluid or other lacrimal fluid. In an embodiment, the drug supply 420 includes a plurality of therapeutic agent inclusions 452, which can be distributed in a matrix 454. In an embodiment, the inclusions 452 comprise a concentrated form of the therapeutic agent (e.g., a crystalline agent form). In an embodiment, the matrix 454 comprises a silicone matrix or the like, and the distribution of inclusions 452 within the matrix are homogeneous or non-homogeneous. In an embodiment, the agent inclusions 452 include droplets of oil, such as Latanoprost or other therapeutic agent(s) oil. In still another embodiment, the agent inclusions 452 include solid particles, such as Bimatoprost particles in crystalline form. The inclusions can be of many sizes and shapes. For instance, the inclusions can include microparticles having dimensions on the order of about 1 micrometer to about 100 micrometers.

In the embodiment shown, the drug supply 420 includes a sheath body 456 disposed over at least a portion thereof such as to define at least one exposed surface 458 of the drug supply. In an embodiment, the sheath body 456 comprises polyimide. The exposed surface 458 can be located at or near the proximal end 418 of the implant body 402 such as to contact a tear or a tear film fluid and release the therapeutic agent at one or more therapeutic levels over a sustained time period when the punctal implant 400 is inserted into a lacrimal punctum.

In certain embodiments, the expandable retention member can include a second drug-releasing or other agent-releasing drug supply 460 to provide a sustained drug or other agent release to one or both of a wall of a lacrimal canaliculus or a nasolacrimal system. The drug supply 460 can be configured to store and slowly dispense an agent after contact with lacrimal fluid within a lacrimal canaliculus. In an embodiment, the agent included in the expandable retention member can comprise medicaments, therapeutic agents, or antimicrobials (e.g., silver).

Figure 5:
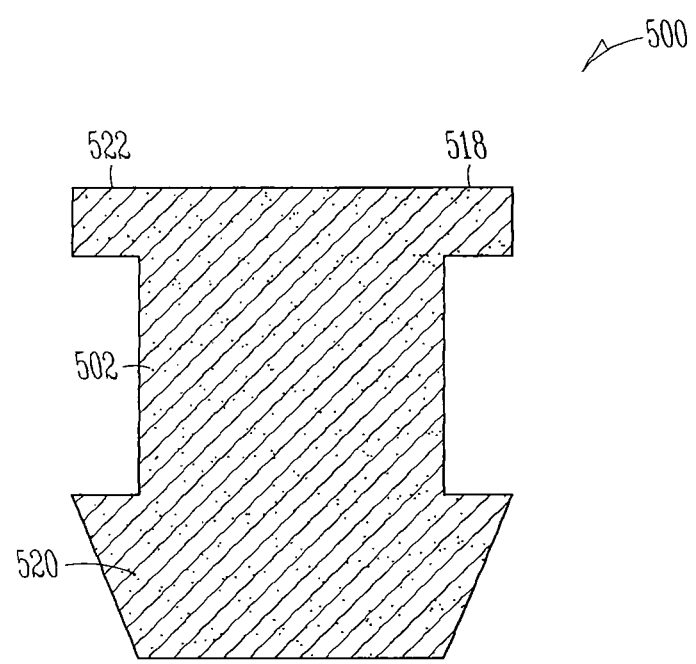
FIG. 5 illustrates an example of a cross-sectional view of a punctal implant configured to be retained at least partially within a lacrimal punctum or canalicular anatomy.
Figure 6:
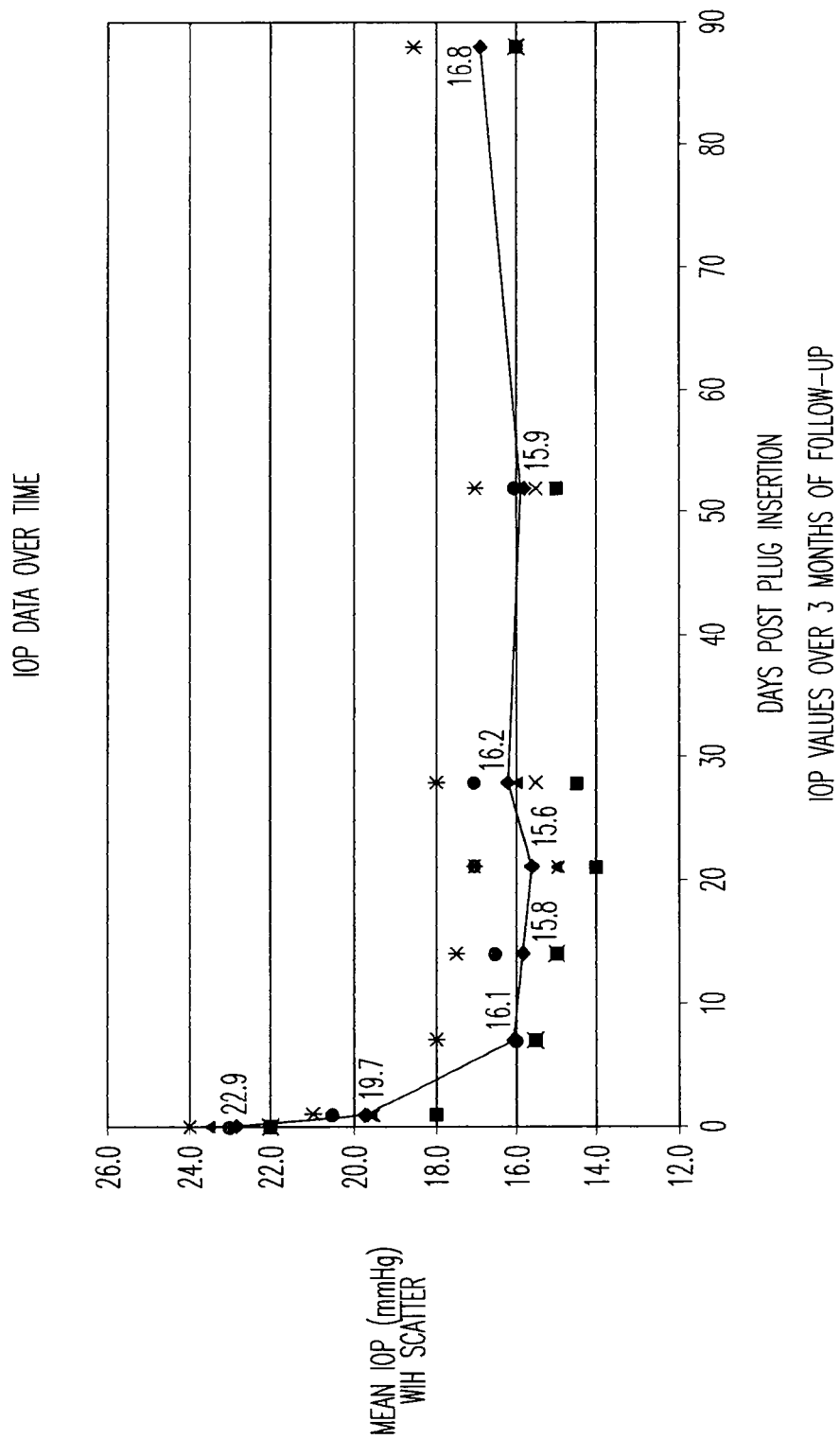
FIG. 6 illustrates intraocular pressure values over three months of follow-up.
Figure 7:
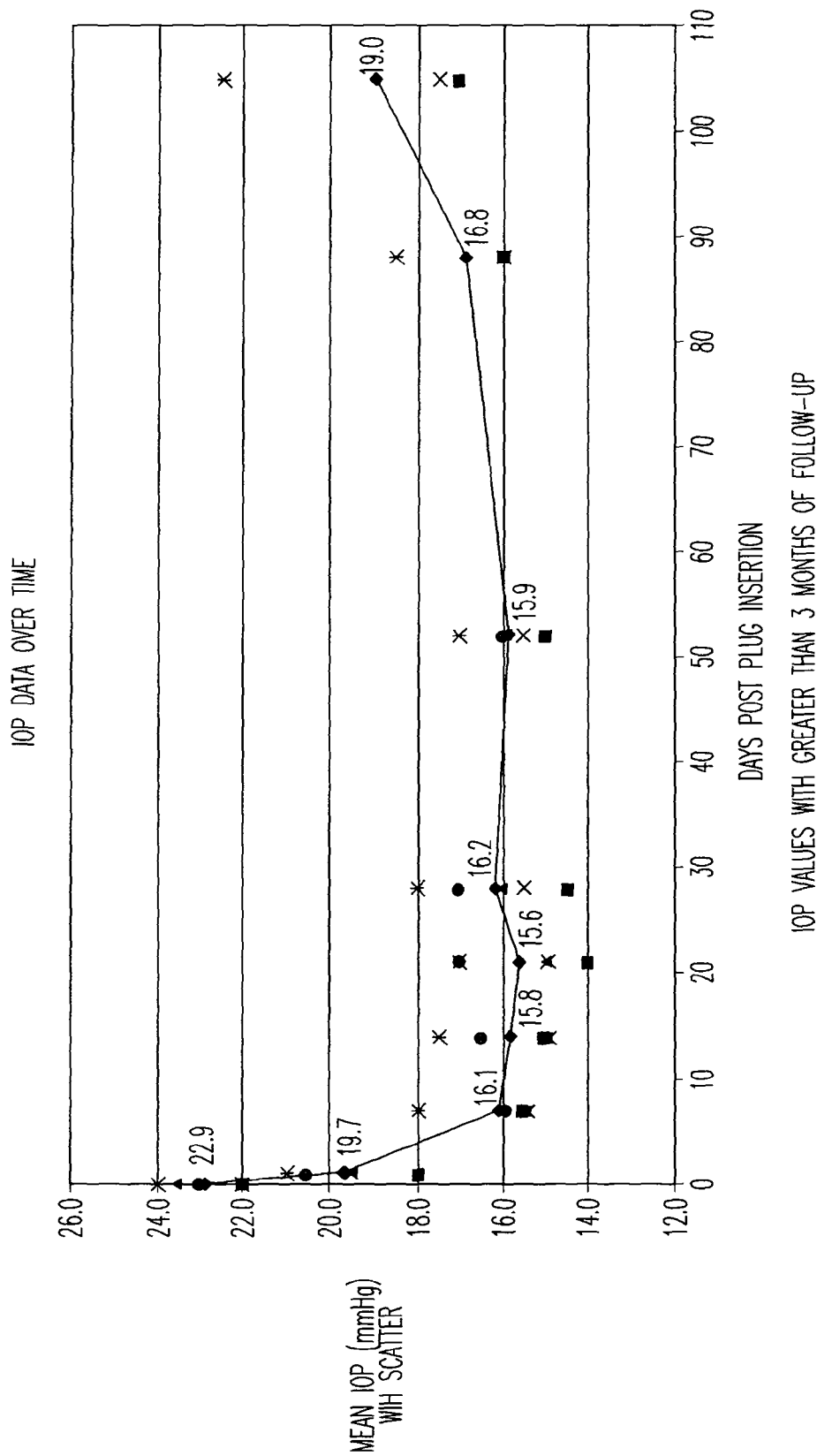
FIG. 7 illustrates intraocular pressure values with greater than three months of follow-up.
Figure 8:
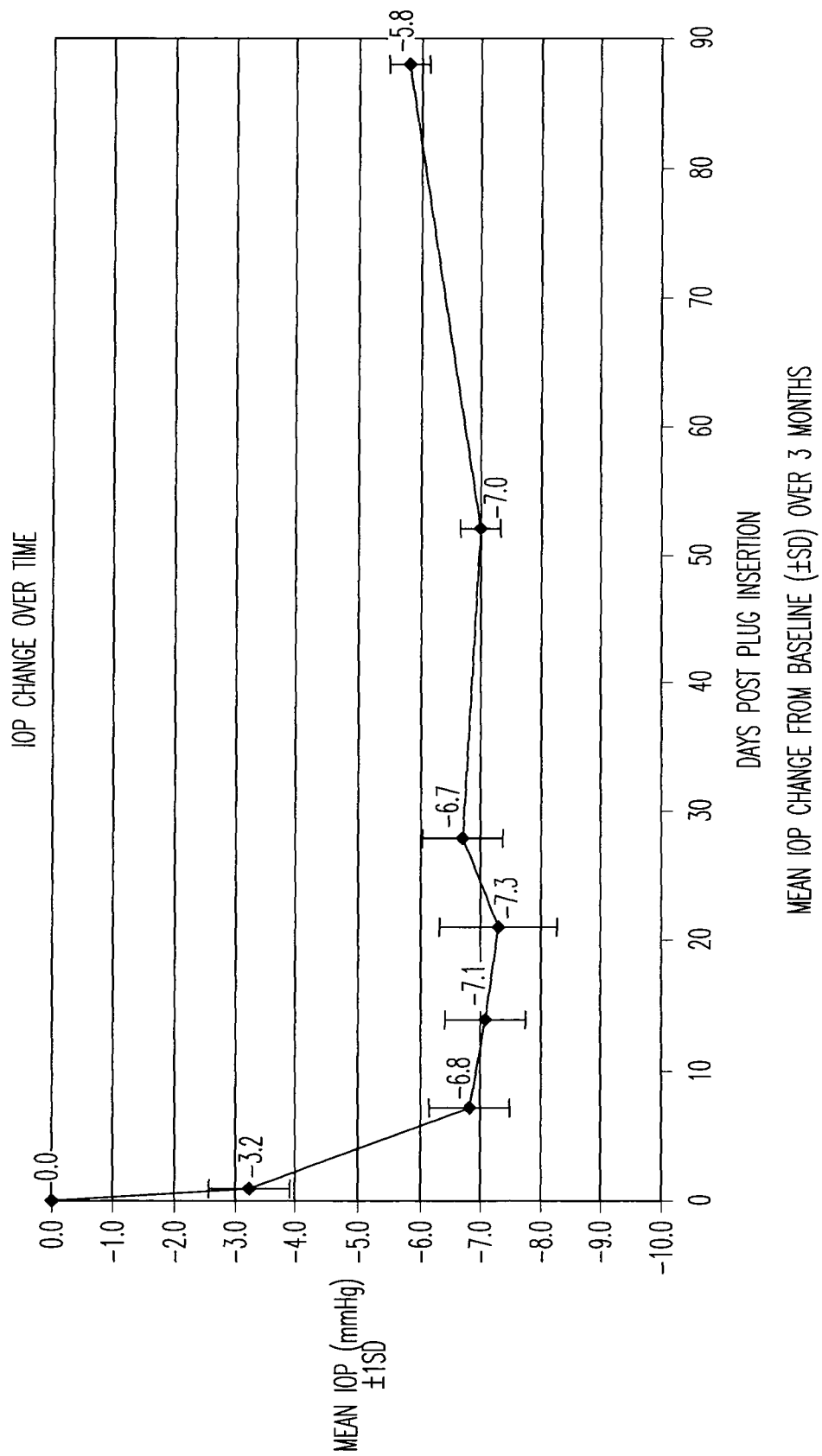
FIG. 8 illustrates mean intraocular pressure change from baseline (+/−SD) over three months time.

FIG. 5 illustrates an example embodiment of a cross-sectional view of a punctal implant 500 taken along a line parallel to a longitudinal axis of the implant. As shown in FIG. 5, the punctal implant 500 comprises an implant body 502. In the embodiment shown, the implant body 502 includes an integral feedback or other projection 522, such as a projection extending laterally at least partially from or around a proximal end 518 of the implant body 502. The projection 522 is in the form of a head portion extending radially outwardly from the implant body 502 to a degree sufficient so that at least a portion of the head portion will extend beyond and be exterior to the punctum after insertion of the implant body 502 distal portions into the canaliculus.

In this embodiment, the implant body 502 is at least partially impregnated with a drug-releasing or other agent-releasing drug supply 520. In certain embodiments, the drug supply 520 is disposed within, dispersed throughout, or otherwise contained in the implant body 502. For instance, the implant body 502 can comprise a matrix of a polymeric component and one or more agent-releasing drug supplies 520. The one or more agent-releasing drug supplies 520 can be distributed substantially thought the matrix and released over time. In this way, the implant body 502 can be effective in providing prolonged delivery of one or more therapeutic agents to an eye, for example, to the outer surface of the eye. As shown in FIG. 5, the implant body 502 can be sized, shaped or otherwise configured to be at least partially retained in a lacrimal canaliculus while the therapeutic agent is being released. As discussed in commonly-owned Odrich, application Ser. No. 10/825,047 (filed April 15, 200 and entitled Drug Delivery via Punctal Plug), which is herein incorporated by reference in its entirety, the agent of the drug supply 520 can be saturated in and released from the implant body 502, such as released into tear fluid of the eye or into the nasolacrimal duct system.

In various embodiments, an impermeable sheath or coating is disposed over one or more portions of the implant body 502 to control drug supply 520 release therefrom. For instance, a non-biodegradable polymer that is substantially impermeable to the drug supply 520 can be coated around a periphery of the implant body 502. In some examples, at least one surface of the implant body 502 is left uncoated or unsheathed to allow the drug supply 520 stored in the body 502 to release to surrounding bodily tissue or structures. In some examples, the impermeable sheath or coating includes at least one pore extending from the outer surface of the coating to the outer surface of the implant body 502. The at least one pore can be sized, shaped or otherwise configured to allow drug supply 520 stored in the body 502 to release to the surrounding bodily tissue or structures, such as unidirectional release to an eye. In some examples, the at least one pore is etched into the coating, such as using a laser. In some examples, the at least one pore is formed into the coating upon the implant dissolving of a salt-impregnated portion of the coating. In an example, the impermeable sheath or coating includes parylene.

Making the Implant:

Those of skill in the art will be familiar with various methods useful for making the implants described herein. Particular methods are described in the above-identified patent documents, the disclosures of which are incorporated herein by reference in their entirety.

For example, drug cores as described above may be fabricated with different cross sectional sizes of 0.006 inches, 0.012 inches, and 0.025 inches. Drug concentrations in the core may be 5%, 10%, 20%, 30% in a silicone matrix. These drug cores can be made with a syringe tube and cartridge assembly, mixing latanoprost or other therapeutic agent(s) with silicone, and injecting the mixture into a polyimide tube which is cut to desired lengths and sealed. The length of the drug cores can be approximately 0.80 to 0.95 mm, which for a diameter of 0.012 inches (0.32 mm) corresponds to total latanoprost or other therapeutic agent(s) content in the drug cores of approximately 3.5 micrograms, 7 micrograms, 14 micrograms and 21 micrograms for concentrations of 5%, 10%, 20% and 30%, respectively.

Syringe Tube and Cartridge Assembly: 1. Polyimide tubing of various diameters (for example 0.006 inches, 0.0125 inches and 0.025 inches) can be cut to 15 cm length. 2. The polyimide tubes can be inserted into a Syringe Adapter. 3. The polyimide tube can be adhesive bonded into luer adapter (Loctite, low viscosity UV cure). 4. The end of the assembly can then be trimmed. 5. The cartridge assembly can be cleaned using distilled water and then with methanol and dried in oven at 60.degree. C.

The latanoprost or other therapeutic agent(s) can be mixed with silicone. Latanoprost or other therapeutic agent(s) may be provided as a 1% solution in methylacetate. The appropriate amount of solution can be placed into a dish and using a nitrogen stream, the solution can be evaporated until only the latanoprost or other therapeutic agent(s) remains. The dish with the latanoprost or other therapeutic agent(s) oil can be placed under vacuum for 30 minutes. This latanoprost or other therapeutic agent(s) can then be combined with silicone, with three different concentrations of latanoprost or other therapeutic agent(s) (5%, 10% and 20%) in silicone NuSil 6385 being injected into tubing of different diameters (0.006 in, 0.012 in and 0.025 inches) to generate 3×3 matrixes. The percent of latanoprost or other therapeutic agent(s) to silicone is determined by the total weight of the drug matrix. Calculation: Weight of latanoprost or other therapeutic agent(s)/(weight of latanoprost or other therapeutic agent(s)+weight of silicone)×100=percent drug.

The tube can then be injected: 1. The cartridge and polyimide tubes assembly can be inserted into a 1 ml syringe. 2. One drop of catalyst (MED-6385 Curing Agent) can be added in the syringe. 3. Excess catalyst can be forced out of the polyimide tube with clean air. 4. The syringe can then be filled with silicone drug matrix. 5. The tube can then be injected with drug matrix until the tube is filled or the syringe plunger becomes too difficult to push. 6. The distal end of the polyimide tube can be closed off and pressure can be maintained until the silicone begins to solidify. 7. Allow to cure at room temperature for 12 hours. 8. Place under vacuum for 30 minutes. 9. The tube can then be place in the correct size trim fixture (prepared in house to hold different size tubing) and drug inserts can be cut to length (0.80-0.95 mm).

Release of Latanoprost or Other Therapeutic Agent(s) at Effective Levels:

The rate of release of latanoprost or other therapeutic agent(s) can be related to the concentration of latanoprost or other therapeutic agent(s) dissolved in the drug core. In some embodiments, the drug core comprises non-therapeutic agents that are selected to provide a desired solubility of the latanoprost or other therapeutic agent(s) in the drug core. The non-therapeutic agent of the drug core can comprise polymers as described herein, and additives. A polymer of the core can be selected to provide the desired solubility of the latanoprost or other therapeutic agent(s) in the matrix. For example, the core can comprise hydrogel that may promote solubility of hydrophilic treatment agent. In some embodiments, functional groups can be added to the polymer to provide the desired solubility of the latanoprost or other therapeutic agent(s) in the matrix. For example, functional groups can be attached to silicone polymer.

Additives may be used to control the concentration of latanoprost or other therapeutic agent(s) by increasing or decreasing solubility of the latanoprost or other therapeutic agent(s) in the drug core so as to control the release kinetics of the latanoprost or other therapeutic agent(s). The solubility may be controlled by providing appropriate molecules or substances that increase or decrease the content of latanoprost or other therapeutic agent(s) in the matrix. The latanoprost or other therapeutic agent(s) content may be related to the hydrophobic or hydrophilic properties of the matrix and latanoprost or other therapeutic agent(s). For example, surfactants and salts can be added to the matrix and may increase the content of hydrophobic latanoprost in the matrix. In addition, oils and hydrophobic molecules can be added to the matrix and may increase the solubility of hydrophobic treatment agent in the matrix.

Instead of or in addition to controlling the rate of migration based on the concentration of latanoprost or other therapeutic agent(s) dissolved in the matrix, the surface area of the drug core can also be controlled to attain the desired rate of drug migration from the core to the target site. For example, a larger exposed surface area of the core will increase the rate of migration of the treatment agent from the drug core to the target site, and a smaller exposed surface area of the drug core will decrease the rate of migration of the latanoprost or other therapeutic agent(s) from the drug core to the target site. The exposed surface area of the drug core can be increased in any number of ways, for example by any of castellation of the exposed surface, a porous surface having exposed channels connected with the tear or tear film, indentation of the exposed surface, protrusion of the exposed surface. The exposed surface can be made porous by the addition of salts that dissolve and leave a porous cavity once the salt dissolves. Hydrogels may also be used, and can swell in size to provide a larger exposed surface area. Such hydrogels can also be made porous to further increase the rate of migration of the latanoprost or other therapeutic agent(s).

Further, an implant may be used that includes the ability to release two or more drugs in combination, such as the structure disclosed in U.S. Pat. No. 4,281,654 (Shell). For example, in the case of glaucoma treatment, it may be desirable to treat a patient with multiple prostaglandins or a prostaglandin and a cholinergic agent or an adrenergic antagonist (beta blocker), such as Alphagan™, or latanoprost and a carbonic anhydrase inhibitor.

In addition, drug impregnated meshes may be used such as those disclosed in US Patent Publication No. 2002/0055701 (serial no. 77/2693) or layering of biostable polymers as described in US Patent Publication No. 2005/0129731 (serial no. 97/9977), the disclosures of which are incorporated herein in their entirety. Certain polymer processes may be used to incorporate latanoprost or other therapeutic agent(s) into the devices of the present invention; such as so-called "self-delivering drugs" or PolymerDrugs (Polymerix Corporation, Piscataway, N.J.) are designed to degrade only into therapeutically useful compounds and physiologically inert linker molecules, further detailed in US Patent Publication No. 2005/0048121 (serial no. 86/1881; East), hereby incorporated by reference in its entirety. Such delivery polymers may be employed in the devices of the present invention to provide a release rate that is equal to the rate of polymer erosion and degradation and is constant throughout the course of therapy. Such delivery polymers may be used as device coatings or in the form of microspheres for a drug depot injectable (such as a reservoir of the present invention). A further polymer delivery technology may also be configured to the devices of the present invention such as that described in US Patent Publication No. 2004/0170685 (serial no. 78/8747; Carpenter), and technologies available from Medivas (San Diego, Calif.).

In specific embodiments, the drug core matrix comprises a solid material, for example silicone, that encapsulates inclusions of the latanoprost or other therapeutic agent(s). The drug comprises molecules which are very insoluble in water and slightly soluble in the encapsulating drug core matrix. The inclusions encapsulated by the drug core can be micro-particles having dimensions from about 1 micrometer to about 100 micrometers across. The drug inclusions can comprise droplets of oil, for example latanoprost oil. The drug inclusions can dissolve into the solid drug core matrix and substantially saturate the drug core matrix with the drug, for example dissolution of latanoprost oil into the solid drug core matrix. The drug dissolved in the drug core matrix is transported, often by diffusion, from the exposed surface of the drug core into the tear film. As the drug core is substantially saturated with the drug, in many embodiments the rate limiting step of drug delivery is transport of the drug from the surface of the drug core matrix exposed to the tear film. As the drug core matrix is substantially saturated with the drug, gradients in drug concentration within the matrix are minimal and do not contribute significantly to the rate of drug delivery. As surface area of the drug core exposed to the tear film is nearly constant, the rate of drug transport from the drug core into the tear film can be substantially constant. Naturally occurring surfactants may affect the solubility of the latanoprost or other therapeutic agent(s) in water and molecular weight of the drug can affect transport of the drug from the solid matrix to the tear. In many embodiments, the latanoprost or other therapeutic agent(s) is nearly insoluble in water and has a solubility in water of about 0.03% to 0.002% by weight and a molecular weight from about 400 grams/mol. to about 1200 grams/mol.

In many embodiments the latanoprost or other therapeutic agent(s) has a very low solubility in water, for example from about 0.03% by weight to about 0.002% by weight, a molecular weight from about 400 grams per mole (g/mol) to about 1200 g/mol, and is readily soluble in an organic solvent. Latanoprost is a liquid oil at room temperature, and has an aqueous solubility of 50 micrograms/mL in water at 25 degrees C., or about 0.005% by weight and a M.W. of 432.6 g/mol.

Naturally occurring surfactants in the tear film, for example surfactant D and phospholipids, may effect transport of the drug dissolved in the solid matrix from the core to the tear film. In some embodiments the drug core can be configured in response to the surfactant in the tear film to provide sustained delivery of latanoprost or other therapeutic agent(s) into the tear film at therapeutic levels. For example, empirical data can be generated from a patient population, for example 10 patients whose tears are collected and analyzed for surfactant content. Elution profiles in the collected tears for a drug that is sparingly soluble in water can also be measured and compared with elution profiles in buffer and surfactant such that an in vitro model of tear surfactant is developed. An in vitro solution with surfactant based on this empirical data can be used to adjust the drug core in response to the surfactant of the tear film.

The drug cores may also be modified to utilize carrier vehicles such as nanoparticles or microparticles depending on the size of the molecule to be delivered such as latent-reactive nanofiber compositions for composites and nano-textured surfaces (Innovative Surface Technologies, LLC, St. Paul, Minn.), nanostructured porous silicon, known as BioSilicon™, including micron sized particles, membranes, woven fibers or micromachined implant devices (pSividia, Limited, UK) and protein nanocage systems that target selective cells to deliver a drug (Chimeracore).

In many embodiments, the drug insert comprises of a thin-walled polyimide tube sheath with a drug core comprising latanoprost dispersed in Nusil 6385 (MAF 970), a medical grade solid silicone that serves as the matrix for drug delivery. The distal end of the drug insert is sealed with a cured film of solid Loctite 4305 medical grade adhesive. The drug insert may be placed within the bore of the punctal implant, the Loctite 4305 adhesive does not come into contact with either tissue or the tear film. The inner diameter of the drug insert can be 0.32 mm; and the length can be 0.95 mm. At least four latanoprost concentrations in the finished drug product can be employed: Drug cores can comprise 3.5, 7, 14 or 21 micrograms latanoprost, with percent by weight concentrations of 5, 10, 20, or 30% respectively. Assuming an overall elution rate of approximately 100 ng/day, the drug core comprising 14 micrograms of latanoprost is configured to deliver drug for approximately at least 100 days, for example 120 days. The overall weight of the drug core, including latanoprost or other therapeutic agent(s), can be about 70 micrograms. The weight of the drug insert including the polyimide sleeve can be approximately 100 micrograms.

In many embodiments, the drug core may elute with an initial elevated level of latanoprost or other therapeutic agent(s) followed by substantially constant elution of the latanoprost or other therapeutic agent(s). In many instances, an amount of latanoprost or other therapeutic agent(s) released daily from the core may be below the therapeutic levels and still provide a benefit to the patient. An elevated level of eluted latanoprost or other therapeutic agent(s) can result in a residual amount of latanoprost or other therapeutic agent(s) or residual effect of the latanoprost or other therapeutic agent(s) that is combined with a sub-therapeutic amount of latanoprost or other therapeutic agent(s) to provide relief to the patient. In embodiments where therapeutic level is about 80 ng per day, the device may deliver about 100 ng per day for an initial delivery period. The extra 20 ng delivered per day can have a beneficial effect when latanoprost or other therapeutic agent(s) is released at levels below the therapeutic level, for example at 60 ng per day. As the amount of drug delivered can be precisely controlled, an initial elevated dose may not result in complications or adverse events to the patient.

In certain embodiments, the methods of the invention result in a percentage reduction in intraocular pressure of approximately 28%. In some embodiments, the methods of the invention results in a percentage reduction or decrease in intraocular pressure of approximately 30%, approximately 29%, approximately 28%, approximately 27%, approximately 26%, approximately 25%, approximately 24%, approximately 23%, approximately 22%, approximately 21%, or approximately 20%. In certain embodiments, the methods of the invention result in a percentage reduction or decrease in intraocular pressure of at least 30%, at least 29%, at least 28%, at least 27%, at least 26%, at least 25%, at least 24%, at least 23%, at least 22%, at least 21%, at least 20%, at least 15%, or at least 10%.

In certain embodiments, the methods of the invention result in a reduction in intraocular pressure from baseline over a treatment period of about 6 mm Hg, about 5 mm Hg, about 4 mm Hg, about 3 mm Hg or about 2 mm Hg. In certain embodiments, the methods of the invention result in a reduction in intraocular pressure from baseline of at least 2 mm Hg, at least 3 mm Hg, at least 4 mm Hg, at least 5 mm Hg, at least 6 mm Hg, or at least 7 mm Hg. In some embodiments, intraocular pressure is reduced to less than or equal to 21 mm Hg, less than or equal to 20 mm Hg, less than or equal to 19 mm Hg, less than or equal to 18 mm Hg, less than or equal to 17 mm Hg, less than or equal to 16 mm Hg, less than or equal to 15 mm Hg, less than or equal to 14 mm Hg, less than or equal to 13 mm Hg, or less than or equal to 12 mm Hg.

In an embodiment, the implants and methods of the invention provide a 90-day course of treatment. In other embodiments, the implants and methods of the invention provide a 60-day course of treatment. In still other embodiments, the implants and methods of the invention provide a 45-day course of treatment. In still other embodiments, the implants and methods of the invention provide a 30-day course of treatment, depending upon the disease to be treated and the therapeutic agent to be delivered. Other embodiments include one week, two weeks, three weeks, four weeks, five weeks, six weeks, seven weeks, eight weeks, nine weeks, ten weeks, eleven weeks, or twelve weeks of treatment. In some embodiments, effective levels of latanoprost or other therapeutic agent(s) release during the entire course of treatment. In a further embodiment, the variability in intraocular pressure over the course of treatment is less than about 1 mm Hg. In other embodiments, the variability in intraocular pressure over the course of treatment is less than about 2 mm Hg. In other embodiments, the variability in intraocular pressure over the course of treatment is less than about 3 mm Hg.

The implants described herein may be inserted into the superior punctum, the inferior punctum, or both, and may be inserted into one or both eyes of the subject.

As described below, a study was conducted using five test subjects ≥18 years of age who had a diagnosis of ocular hypertension or glaucoma at baseline. Sustained release implants comprising 14 micrograms latanoprost were inserted into the puncta of the subjects. Within seven days, a mean reduction in intraocular pressure of 6 mm Hg was observed. This reduction was maintained over approximately three months.

The invention can be described by the following non-limiting examples.

Example 1

An open-label, prospective study was conducted with patients being followed for up to 3 months post-placement. Patients were males or females 18 years of age or older, with a diagnosis of ocular hypertension or glaucoma, who had two sequential measurements (at least 48 hours apart) of intra-ocular pressure of 22 mmHg or greater after an appropriate drug washout period (see Table 2 below).

Implant:

The Punctal Plug Drug Delivery System (PPDS) consisted of a drug insert configured to be placed in a suitable commercially available punctal implant with a pre-existing bore. All materials used in the construction of the drug insert were medical grade materials that passed a battery of safety/toxicity tests. The drug insert was a thin-walled polyimide tube that was filled with latanoprost dispersed in Nusil 6385, a cured medical grade solid silicone. The cured silicone served as the solid, non-erodible matrix from which latanoprost slowly eluted. The drug insert was sealed at the distal end with a cured film of solid Loctite 4305 medical grade adhesive (cyanoacrylate). The polyimide sleeve was inert and, together with the adhesive, provided structural support and a barrier to both lateral drug diffusion and drug diffusion through the distal end of the drug insert. The drug insert was seated in the bore of the punctal implant and was held in place via an interference fit. The assembled system was packaged and sterilized.

Procedures:

Patients were fitted with a punctal implant after the first visit where ocular hypertension was demonstrated. Patients were evaluated at the following qualification visit to determine if the punctal implant was still in place. Following a subsequent baseline visit, subjects received one Punctal Plug Drug Delivery System in the inferior punctum of both eyes. If at any exam a punctal implant was not in place, a new Punctal Plug Drug Delivery System was inserted. The delivery system was placed in the inferior or superior punctum after the appropriate washout period, as defined in Table 2 below. If during subsequent visits the Punctal Plug System was not present a replacement device was inserted.

Placement and removal of the Punctum Plug Drug Delivery System was accomplished in the same manner as for other commercially available punctal implants. Generally, for placement the size of a punctal implant to be used was determined by using suitable magnification or, if provided, using a sizing tool that accompanied the punctal implant. The patient's punctum was dilated if necessary to fit the punctal implant. A drop of lubricant was applied if necessary to facilitate placement of the implant into the punctum. Using an appropriate placement instrument the implant was inserted into the superior or inferior punctum of the eye. After placement, the cap of the implant was visible. This process was repeated for the patient's other eye. For removal of the implant, small surgical forceps were used to securely grasp the implant at the tube section below the cap. Using a gentle tugging motion the implant was gently retrieved.

TABLE 2

Recommended Washout Period

| Drug Class | Sample Agent(s) | Washout Period |
|---|---|---|
| Prostaglandin analogs | Latanoprost (Xalatan), Bimatoprost (Lumigan), Travoprost (Travatan) | 4 weeks |
| Beta blocker | Betaxolol (Betoptic) Timolol (Betimol) | 3 weeks |
| Adrenergic agonists | Apraclonidine (Iopidine) Dipivefrin (Propine) | 2 weeks |
| AH other IOP lowering medications | Brinzolamide (Azopt) Dorzolamide (Trusopt) Pilocarpine (Pilocar) | 72 hours |

During the course of the study, intraocular pressure was measured by Goldmann applanation tonometry. Both a topical anesthetic and fluorescein were applied. This was accomplished by use of a combination product (e.g., Fluress®, benoxinate and fluorescein), or by separate application of a local anesthetic and fluorescein for corneal assessments. Immediately thereafter, intraocular pressure was measured using an applanation method. Efficacy was evaluated as change in IOP from the baseline.

Drug Release Kinetics In Vitro:

Multiple in vitro experiments have been performed with several medical grade silicone formulations to demonstrate the ability to control latanoprost elution rates. The amount of latanoprost in the commercially available product Xalatan® is approximately 1.5 micrograms/drop. A punctal implant delivery system that elutes approximately 100 ng/day of latanoprost therefore delivers only about 6% of the amount of drug as in Xalatan®. For this reason the punctal implant device should not pose any drug safety risk to the patient.

Adverse Events:

The risks associated with the device are possible ocular irritation due to the punctal implant or ineffective relief of ocular hypertension. The total drug content for the punctal implant system is equivalent to 10-20 drops of Xalatan®. Safety was evaluated by assessment of the ocular signs at slit lamp examination, intraocular pressure (IOP), visual acuity, and by determining the incidence and severity of adverse events.

Results:

The IOP for each subject is the average IOP of 2 eyes, unless only 1 eye is treated. Thus, N=10 eyes equated to 5 subjects. N=10 eyes on Days 0-28, N=9 eyes on Day 52, N=6 eyes on Day 88-105 (2 subjects excluded at Day 88 and beyond for starting Xalatan® in fellow eye, which had lost the implant; thus 3 subjects remained in the study from day 88-105). At Day 105, 1 subject out of the 3 subjects lost efficacy (IOP is within 2 mmHg below baseline).

As shown in FIG. 1 and Table 3, post wash-out mean baseline IOP was 22.9±0.9 mmHg. Seven days after PPDS placement, mean IOP decreased to 16.1±1.1 mmHg and remained stable throughout the follow-up period. At Day 88, mean IOP was 16.5±1.2 mmHg representing a 28% pressure decrease from baseline (p<0.05). These results demonstrate that treatment with the sustained release punctal implant delivery system is safe and effective in the studied subject population.

TABLE 3

Mean intraocular pressure in subjects treated with 14 μg Latanoprost Punctal Plug Delivery System

| Study Day | N | Mean IOP | Standard Deviation |
|---|---|---|---|
| 0 | 5 subjects (10 eyes) | 22.9 | 0.9 |
| 1 | 5 subjects (10 eyes) | 19.7 | 1.2 |
| 7 | 5 subjects (10 eyes) | 16.1 | 1.1 |
| 14 | 5 subjects (10 eyes) | 15.8 | 1.2 |
| 21 | 5 subjects (10 eyes) | 15.8 | 1.6 |
| 28 | 5 subjects (10 eyes) | 16.2 | 1.4 |
| 52 | 5 subjects (9 eyes) | 15.9 | 0.7 |
| 88 | 3 subjects (6 eyes) | 16.8 | 1.4 |
| 105 | 3 subjects (6 eyes) | 19.0 | 3.0 |

Example 2

A randomized, masked, phase 2 study ("CORE study") was conducted to assess the IOP lowering effect of a Latanoprost Punctal Plug Delivery System (L-PPDS) with a sustained-release drug-eluting core. Sixty-one open-angle glaucoma or ocular hypertension patients with post wash-out IOP between 21 and 30 mmHg were randomized equally to one of three treatment groups, L-PPDS containing a dose of 3.5, 14, or 21 μg of latanoprost, and followed for up to 12 weeks. Main outcome measures were IOP change from baseline and safety.

Efficacy Results:

The analysis of preliminary efficacy was based on the proportion of subjects in each treatment group who did not lose efficacy, IOP, and the IOP changes and percentage changes from baseline at each visit. The intent-to-treat (ITT) data set includes data from all randomized subjects. No subjects were excluded because of protocol violations. The ITT data set was used for analyzing all study variables.

Figure 9:
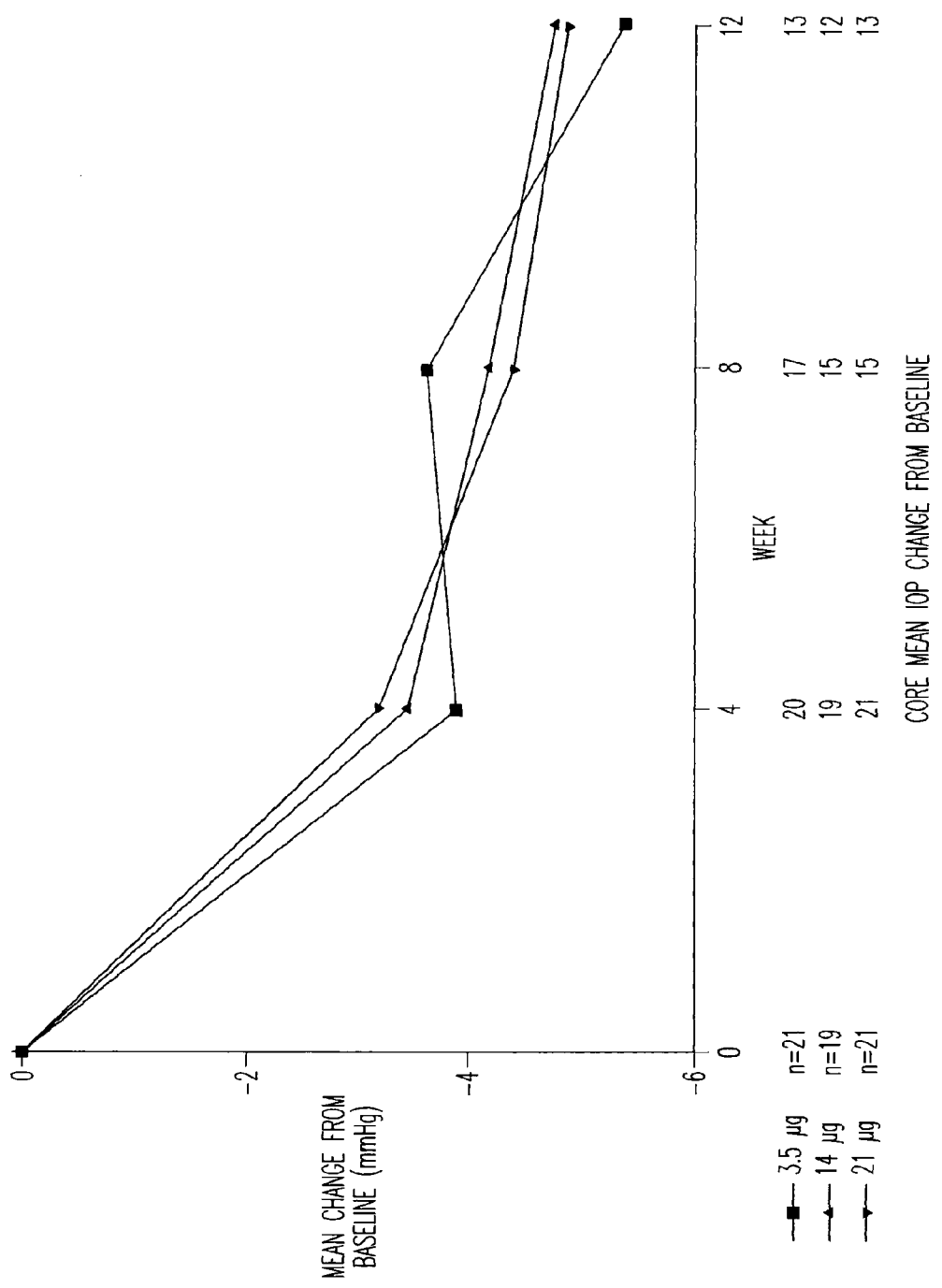
FIG. 9 illustrates mean IOP changes from baseline in the CORE study.

Study findings show that there was an IOP lowering effect among all three doses, with a mean decrease from baseline of 20% at week 12. Mean IOP at screening was 16.8 mmHg; after washout, mean IOP was 24.4±2.1 mmHg. FIGS. 9 and 10 show mean IOP change from baseline for 3.5, 14, and 21 microgram implants at 4, 8 and 12 weeks. At week 8, patients had a mean reduction in IOP of −3.6±2.4, 4.2±3.7, and 4.4±2.4 mmHg in the 3.5, 14, and 21 μg groups respectively (n=17, 15, and 15). At week 12, mean reduction in IOP was −5.4±2.7; −4.8±3.2; and −4.9±2.1 respectively (n=13, 12, and 13), representing a 20% drop from baseline at Week 12. The retention rate of the L-PPDS was 75%.

Figure 11:
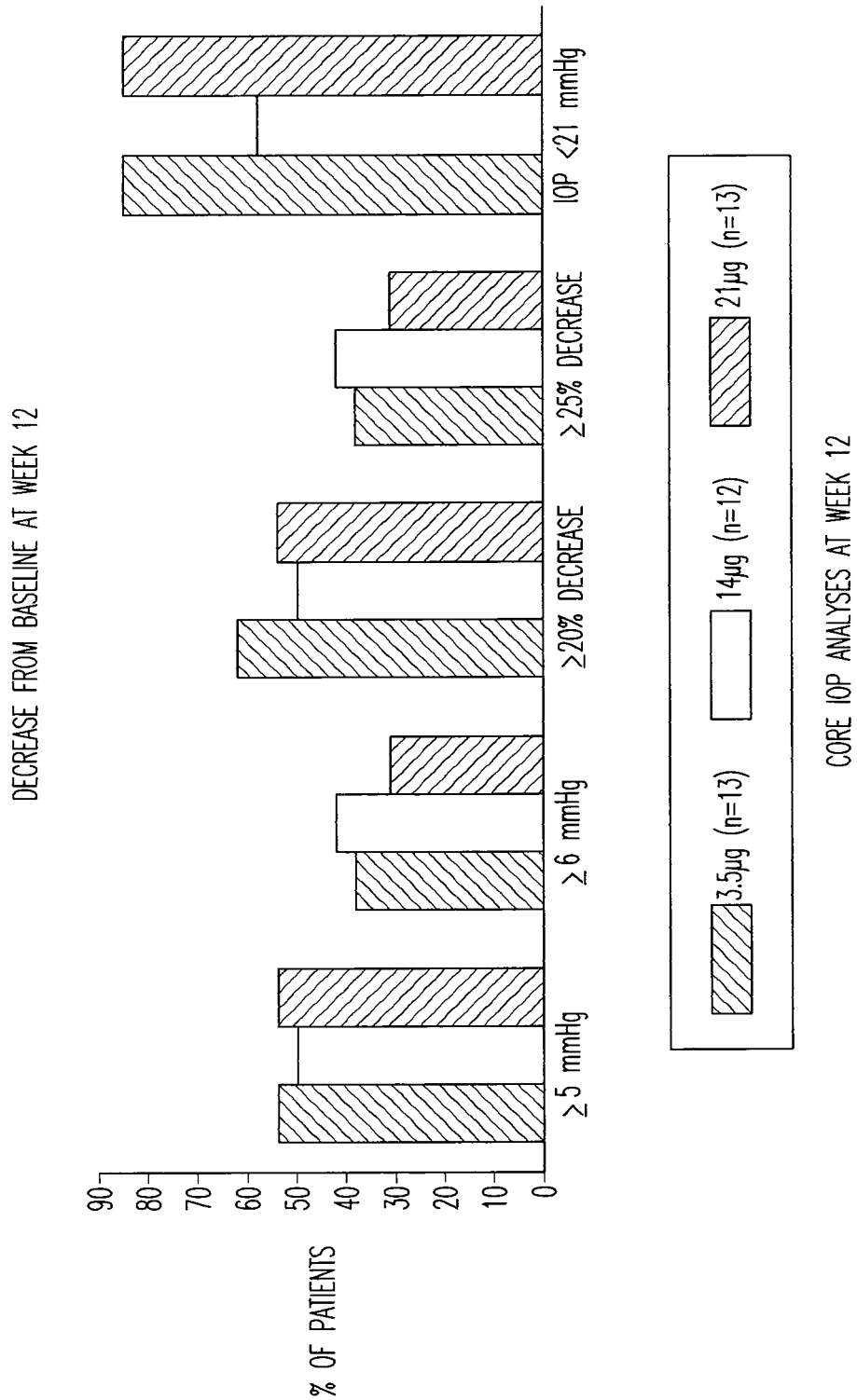
FIG. 11 illustrates decreases in IOP at Week 12 in the CORE study.
Figure 12:
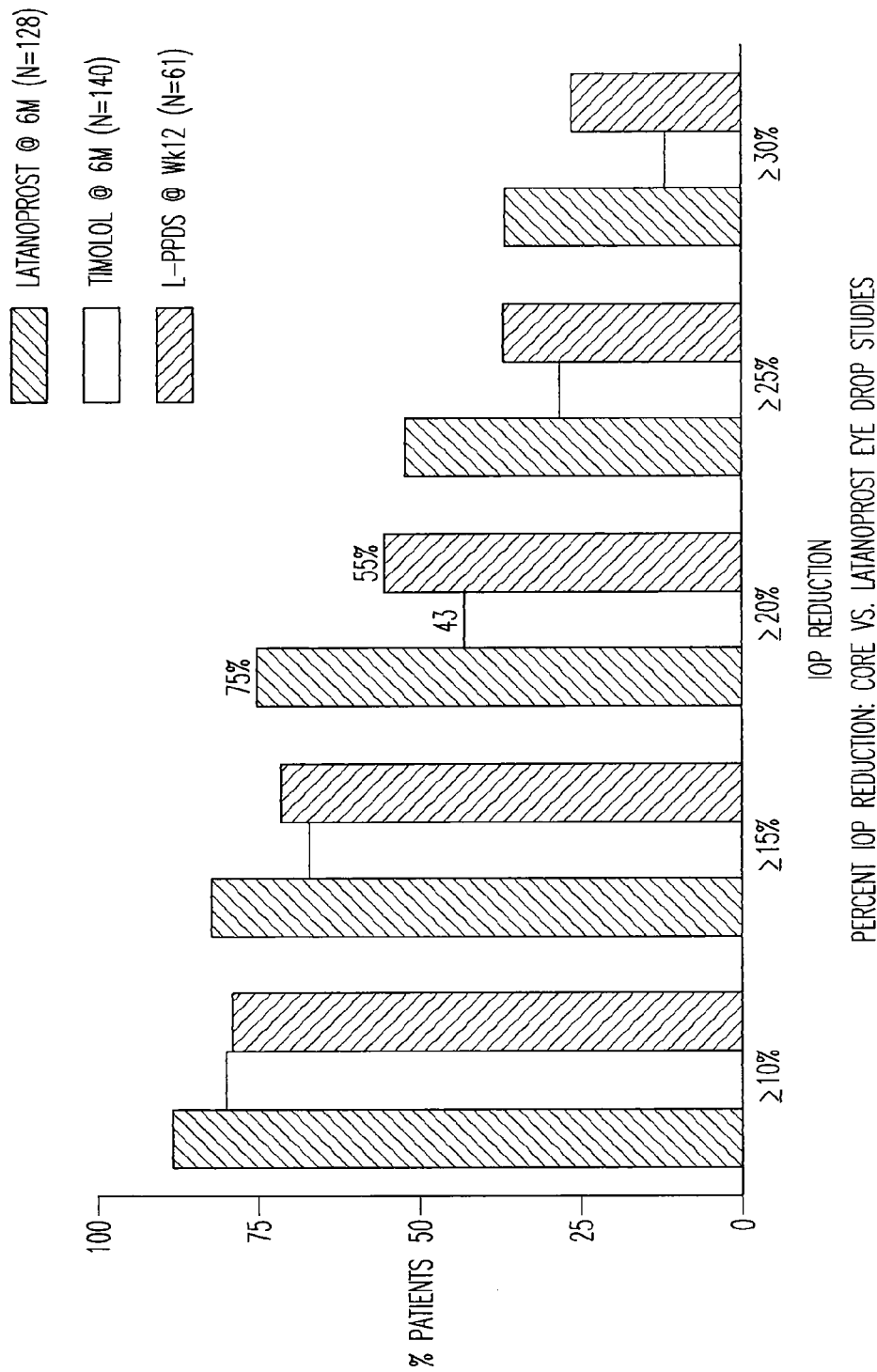
FIG. 12 illustrates percent reduction in IOP in the CORE study compared to a published latanoprost and timolol-eye drop study (Source: US Latanoprost Study Group. Rate of Response to Latanoprost or Timolol in Patients with Ocular Hypertension or Glaucoma. J Glaucoma 2003; 12:466-469). Note, percentages for latanoprost and timolol are estimates from graphs in source.
Figure 14:
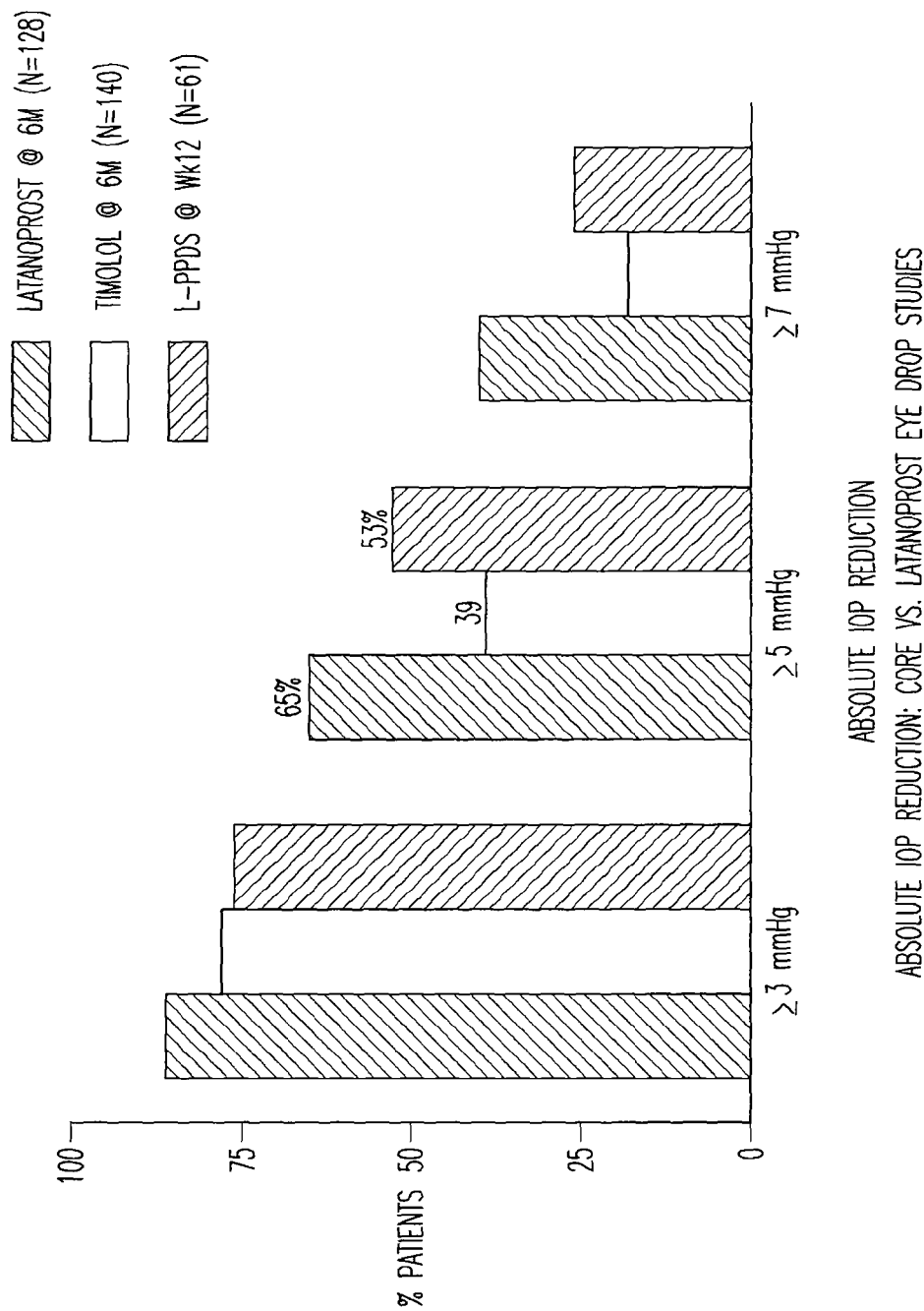
FIG. 14 illustrates absolute reduction in IOP in the CORE study compared to a published latanoprost and timolol eye drop study. Source: US Latanoprost Study Group. Rate of Response to Latanoprost or Timolol in Patients with Ocular Hypertension or Glaucoma. J Glaucoma 2003; 12:466-469. Note: Percentages for latanoprost and timolol are estimates from graphs in source.
Figure 15:
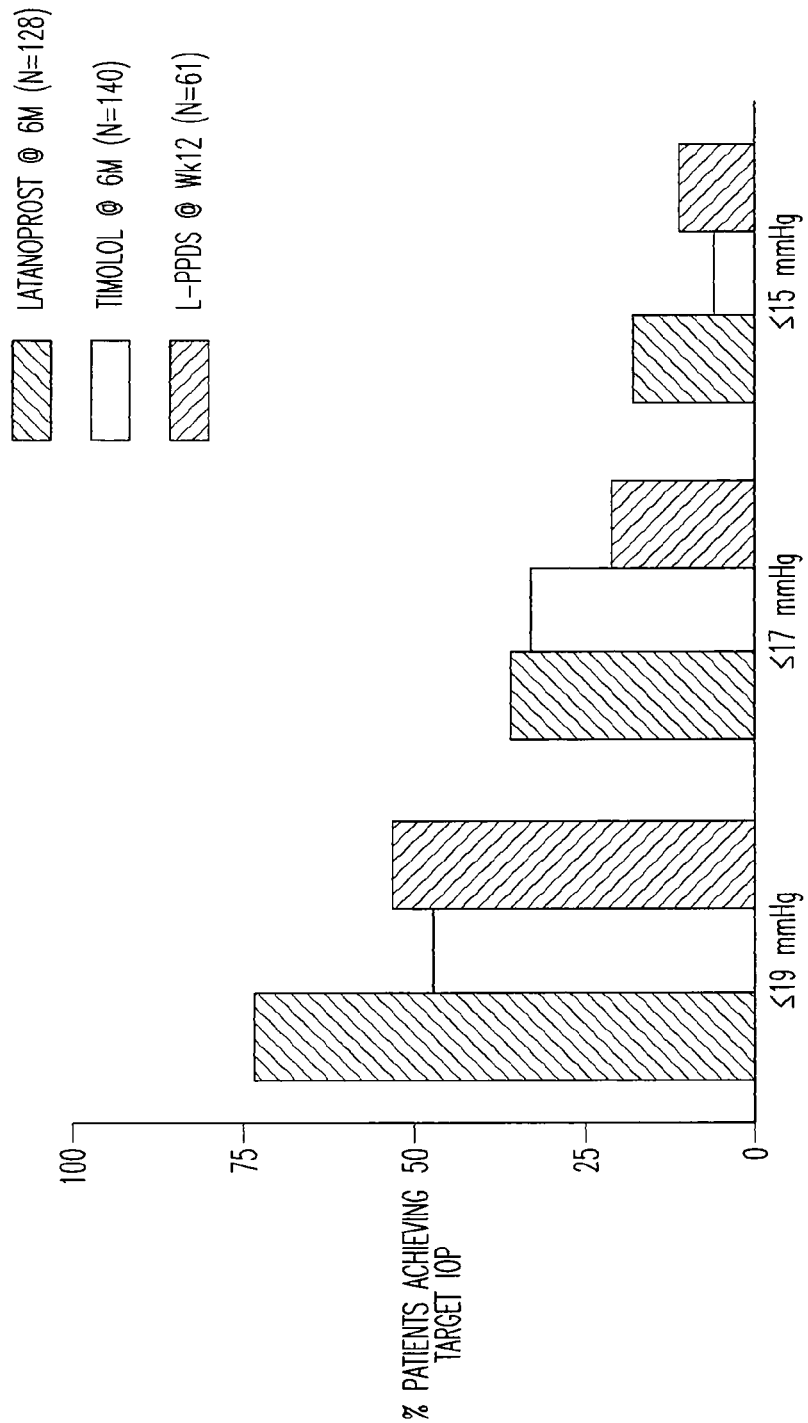
FIG. 15 illustrates the percentage of patients reaching target IOP in the CORE study compared to a published latanoprost and timolol eye drop study. Source: US Latanoprost Study Group. Rate of Response to Latanoprost or Timolol in Patients with Ocular Hypertension or Glaucoma. J Glaucoma 2003; 12:466-469. Note: Percentages for latanoprost and timolol are estimates from graphs in source.

FIG. 11 shows decrease in IOP from baseline at week 12 for each of the treatment groups. Certain reductions in IOP are shown on the X axis. The percentage of patients in each treatment group exhibiting those reductions are shown on the Y axis.

FIGS. 12-15 compare the efficacy of the L-PPDS to other topical glaucoma medication.

Safety Results:

The L-PPDS was well-tolerated over the testing period (see FIG. 16). The overall adverse events ranged from 1.6% to 14.8% and were not dose dependent. The most common adverse events were increased lacrimation (tear production) and ocular discomfort (14.8% and 9.8%, respectively) which were mild and transient in nature and were most likely resolved during the adaptation period to punctal implant wear. Ocular hyperemia and punctate keratitis rates were 1.6% each. At Week 12, 89% of patients rated L-PPDS comfort as 'no awareness' and 8% 'mild awareness,' while tearing was rated 'none' (78%), 'occasional' (14%), or 'mild' (5%). The remaining 3% of patients did not have a comfort and tearing assessment at Week 12. Nineteen patients discontinued before the Week 12 visit due to loss of efficacy/inadequate IOP control.

FIG. 16 shows adverse events associated with the L-PPDS for each treatment group and all treatment groups combined. Reported adverse events included conjunctival hyperemia, eye pruritus, eyelid margin crusting, foreign body sensation, increase in lacrimation, ocular discomfort, ocular hyperemia and punctate keratitis.

FIGS. 17 and 18 compare adverse events of the L-PPDS to adverse events previously reported for eye drop formulations of other medications including travoprost, timolol, latanoprost, and bimatoprost. The following were used for comparison with L-PPDS and are incorporated by reference herein in their entirety: Travoprost Compared With Latanoprost and Timolol in Patients With Open-angle Glaucoma or Ocular Hypertension. *Am J Opthalmol* 2001; 132:472-484 (additional reported AEs included ocular pain, cataract, dry eye, blepharitis, blurred vision); A Six-month Randomized Clinical Trial Comparing the Intraocular Pressure-lowering efficacy of Bimatoprost and Latanoprost in Patients With Ocular Hypertension or Glaucoma. *Am J Opthalmol* 2003; 135:55-63 (additional reported AEs included eyelash growth); One-Year, Randomized Study Comparing Bimatoprost and Timolol in Glaucoma and Ocular Hypertension. *Arch Opthalmol* V120 October 2002 1286-1293 (additional reported AEs included eyelash growth, eye dryness, eye pain; a bimatoprost BID group was also included and showed a higher incidence of adverse events); and Xalatan Ophthalmic Solution 0.005% (50 mg/mL) (Pharmacia) Jun. 5, 1996 Approval: Medical Officers Review, pp. 93, 98-100. Provided by FOI Services.

Summary:

CORE is the first known randomized, parallel group, multicenter US trial investigating a sustained and controlled punctal implant drug delivery system for glaucoma. A mean IOP decrease of 20% was seen at 3 months. The ocular implants were well tolerated; no notable safety issues were observed.

BIBLIOGRAPHY

1. Allen R C. Medical management of glaucoma. In: Albert D M, Jakobiec F A, eds. Principles and Practice of Opthalmology. Philadelphia, Pa.: WB Saunders and Co.; 1994: 1569-1588.
2. AlphaMed punctum plug [product label]. Wauwatosa, Wis.: AlphaMed.
3. Anderson D R, Chauhan B, Johnson C, Katz J, Patella V M, Drance S M. Criteria for progression of glaucoma in clinical management and in outcome studies. Am J Opthalmol 2000; 130(6):827-829.
4. Anderson D R. Collaborative normal tension glaucoma study. Curr Opin Opthalmol. 2003; 14(2):86-90.
5. Bailey I L, Lovie J E. New design principles for visual acuity letter charts. Am J Optom Physiol Opt 1976 November; 53(11):740-745.
6. Balaram M, Schaumberg D A, Dana M R. Efficacy and tolerability outcomes after punctal occlusion with silicone plugs in dry eye syndrome. Am J. Opthalmol. 2001; 131(1):30-36.
7. Baudouin C, Rouland J F, Nordmann J P, Bron A, Pelen F. Efficacy of first- or second-line latanoprost on intraocular pressure and ocular symptoms in patients with open-angle glaucoma or ocular hypertension [in French]. J Fr Ophtalmol. 2006; 29(6):615-624.
8. Bengtsson B, Heijl A. A long-term prospective study of risk factors for glaucomatous visual field loss in patients with ocular hypertension. J Glaucoma. 2005; 14(2):135-138.
9. Brown M M, Brown G C, Spaeth G L. Improper topical self-administration of ocular medication among patients with glaucoma. Can J Opthalmol. 1984; 19(1):2-5.
10. Coleman A L. Glaucoma. Lancet 1999; 354:1803-10.
11. Dasgupta S, Oates V, Bookhart B K, Vaziri B, Schwartz G F, Mozaffari E. Population-based persistency rates for topical glaucoma medications measured with pharmacy claims data. Am J Manag Care. 2002; 8(suppl 10):S255-S261.
12. Diestelhorst M, Schaefer C P, Beusterien K M, et al. Persistency and clinical outcomes associated with latanoprost and beta-blocker monotherapy: evidence from a European retrospective cohort study. Eur J Opthalmol. 2003; 13(suppl 4):S21-S29.
13. Fiscella R G, Geller J L, Gryz L L, Wilensky J, Viana M. Cost considerations of medical therapy for glaucoma. Am J Opthalmol. 1999; 128(4):426-433.
14. Fremont A M, Lee P P, Mangione C M, et al. Patterns of care for open-angle glaucoma in managed care. Arch Opthalmol. 2003; 121(6):777-783.
15. Gordon M O, Beiser J A, Brandt J D, et al. The Ocular Hypertension Treatment Study: baseline factors that predict the onset of primary open-angle glaucoma. Arch Opthalmol. 2002; 120(6):714-720; discussion 829-830.
16. Gordon M O, Kass M A. The Ocular Hypertension Treatment Study: design and baseline description of the participants. Arch Opthalmol 1999; 117(5):573-583.
17. Gurwitz J H, Glynn R J, Monane M, et al. Treatment for glaucoma: adherence by the elderly. Am J Public Health. 1993; 83(5):711-716.
18. Heijl A, Leske M C, Bengtsson B, Hyman L, Bengtsson B, Hussein M, for the Early Manifest Glaucoma Trial Group. Reduction of intraocular pressure and glaucoma progression: results from the Early Manifest Glaucoma Trial. Arch Ophthalmol. 2002; 120(10): 1268-1279.
19. Higginbotham E J, Gordon M O, Beiser J A, et al. The Ocular Hypertension Treatment Study: topical medication delays or prevents primary open-angle glaucoma in African American individuals. Arch Opthalmol. 2004; 122(6): 813-820.
20. Javitt J C, Metrick S, Wang F: Costs of glaucoma in the United States. Invest Opthalmol Vis Sci 1995; 36:S429.
21. Kass M A, Gordon M O, Kymes S M. Incorporating the results of the Ocular Hypertension Treatment Study into clinical practice. Arch Opthalmol. 2005; 123(7):1021-1022.
22. Kass M A, Heuer D K, Higginbotham E J, et al. The Ocular Hypertension Treatment Study: a randomized trial determines that topical ocular hypotensive medication delays or prevents the onset of primary open-angle glaucoma. Arch Opthalmol 2002; 120(6):701-713.
23. Kim B M, Osmanovic S S, Edward D P. Pyogenic granulomas after silicone punctal plugs: a clinical and histopathologic study. Am J Opthalmol. 2005; 139(4): 678-684.
24. Kobelt-Nguyen G, Gerdtham U G, Alm A: Costs of treating primary open-angle glaucoma and ocular hypertension: a retrospective, observational two-year chart review of newly diagnosed patients in Sweden and the United States. J Glaucoma 1998; 7:95.

25. Leibowitz H M, Krueger D E, Maunder L R, et al. The Framingham Eye Study monograph: An opthalmological and epidemiological study of cataract, glaucoma, diabetic retinopathy, macular degeneration, and visual acuity in a general population of 2631 adults, 1973-1975. Surv Opthalmol. 1980; 24(Suppl):335-610.

26. Leonard R. Statistics on Vision Impairment: A Resource Manual (5$^{th}$ Edition). New York: Arlene R. Gordon Research Institute of Lighthouse International; 2002.

27. Leske M C, Heiji A, Hyman L, Bengtsson B, Komaroff E. Factors for progression and glaucoma treatment: the Early Manifest Glaucoma Trial. Curr Opin Opthalmol. 2004; 15(2):102-106.

28. Lichter P R, Musch D C, Gillespie B W, et al, and the CIGTS Study Group. Interim clinical outcomes in the Collaborative Initial Glaucoma Treatment Study comparing initial treatment randomized to medications or surgery. Opthalmology. 2001; 108(11):1943-1953.

29. Liu J H K, Krpike D F, Twa M D, et al. Twenty-four-hour pattern of intraocular pressure in the aging population. Invest Opthalmol V is Sci. 1999; 40(12):2912-2917.

30. Maier P C, Funk J, Schwarzer G, Antes G, Falck-Ytter Y T. Treatment of ocular hypertension and open angle glaucoma: meta-analysis of randomised controlled trials. BMJ. 2005; 331(7509):134. Epub 2005 Jul. 1.

31. Mindel J S. Pharmacokinetics. In: Tasman W, Jaeger E A, eds. Duane's Foundations of Clinical Opthalmology. Vol. 3: Lippincott Williams & Wilkins, 1995: 1-17.

32. Musch D C, Lichter P R, Guire K E, Standardi C L, The CIGTS Study Group. The Collaborative Initial Glaucoma Treatment Study Design, Methods, and Baseline Characteristics of Enrolled Patients. Opthalmology 1999; 106: 653-662.

33. Nordstrom B L, Friedman D S, Mozaffari E, Quigley H A, Walker A M. Persistence and adherence with topical glaucoma therapy. Am J Opthalmol. 2005; 140(4):598-606.

34. Norell S E, Granström P A. Self-medication with pilocarpine among outpatients in a glaucoma clinic. Br J. Opthalmol. 1980 February; 64(2): 137-41.

35. O'Donoghue E P, and the UK and Ireland Latanoprost Study Group. A comparison of latanoprost and dorzolamide in patients with glaucoma and ocular hypertension: a 3 month, randomised study. Br J Opthalmol. 2000; 84:579-582.

36. Parrish R K, Palmberg P, Sheu W P, XLT Study Group. A comparison of latanoprost, bimatoprost, and travoprost in patients with elevated intraocular pressure: a 12-week, randomized, masked-evaluator multicenter study. Am J Opthalmol. 2003; 135(5):688-703.

37. Patel S S, Spencer C M. Latanoprost. A review of its pharmacological properties, clinical efficacy and tolerability in the management of primary open-angle glaucoma and ocular hypertension. Drugs Aging. 1996; 9(5): 363-378.

38. Preferred practice pattern—Primary Open-Angle Glaucoma. American Academy of Opthalmology. (Limited Revision). 2005.

39. Quigley H A: The number of persons with glaucoma worldwide. Br J Opthalmol 1996; 80:389.

40. Reardon G, Schwartz G F, Mozaffari E. Patient persistency with pharmacotherapy in the management of glaucoma. Eur J Opthalmol. 2003; 13(suppl 4):S44-S52.

41. Regnier, et al. Ocular Effects of Topical 0.03% Latanoprost Solution in Normotensive Feline Eyes. Vet Opthalmol 2006; 9(1):39-43.

42. Rouland J F, Berdeaux G, Lafuma A. The economic burden of glaucoma and ocular hypertension: implications for patient management: a review. Drugs Aging 2005; 22(4):315-321.

43. Sakamoto A, Kitagawa K, Tatami A. Efficacy and retention rate of two types of silicone punctal plugs in patients with and without Sjögren's Syndrome. Cornea. 2004; 23(3):249-254.

44. Schwartz G F, Reardon G, Mozaffari E. Persistency with latanoprost or timolol in primary open angle glaucoma suspects. Am J Opthalmol. 2004; 137(suppl 1):S13-S16.

45. Shaya F T, Mullins C D, Wong W, Cho J. Discontinuation rates of topical glaucoma medications in a managed care population. Am J Manag Care. 2002; 8(suppl 10): S271-S277.

46. Silliman N P. Xalatan Ophthalmic Solution 0.005% (50 mg/mL) (Pharmacia) Jun. 6, 1996 Approval: Statistical Review. 1995.

47. Spooner J J, Bullano M F, Ikeda L I, et al. Rates of discontinuation and change of glaucoma therapy in a managed care setting. Am J Manag Care. 2002; 8(suppl 10):S262-S270.

48. The AGIS Investigators. The Advanced Glaucoma Intervention Study (AGIS): 7. The relationship between control of intraocular pressure and visual field deterioration. Am J Opthalmol. 2000; 130(4):429-440.

49. Thomas J V. Primary open angle glaucoma. In: Albert D M, Jakobiec F A, eds. Principles and Practice of Opthalmology. Philadelphia, Pa.: WB Saunders and Co.; 1994: 1342-1345.

50. Thylefors B, Negrel A-D, Pararajasegaram R, Dadzie K Y: Global data on blindness. Bull World Health Org 1995; 73:115-121.

51. Urquhart J. The odds of the three nons when an aptly prescribed medicine isn't working: non-compliance, non-absorption, non-response. Br J Clin Pharmacol. 2002; 54(2):212-220.

52. Waldock A, Snape J, Graham C M. Effects of glaucoma medications on the cardiorespiratory and intraocular pressure status of newly diagnosed glaucoma patients. Br J Opthalmol. 2000; 84(7):710-713.

53. Whitcup S M, et al. A randomized, doube masked, multicenter clinical trial comparing latanoprost and timolol for the treatment of glaucoma and acular hypertension. Br J Opthalmol 2003; 87:57-62.

54. Winfield A J, et al. A study of the causes of non-compliance by patients prescribed eyedrops. Br J Opthalmol. 1990 August; 74(8):477-80.

55. Woodward D F, et al. Pharmalogical Characterization of a Novel Antiglaucoma Agent, (AGN 192024). J Pharmacology and Experimental Therapeutics 2003; 305(2):772-785.

56. Xalatan® (latanoprost ophthalmic solution) 0.005% (50 μg/mL) prescribing information. Division of Pfizer Inc. New York, N.Y.: Pharmacia & Upjohn Company; 2007. http://www.xalatan.com/consumer/prescribinginfo.asp. Accessed Oct. 1, 2007.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable Inconsistencies, the usage in this document controls.

The above description is intended to be illustrative, and not restrictive. For example, the above-described examples (or one or more features thereof) can be used in combination with each other. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Concentrations, amounts, percentages, time periods, etc., of various components or use or effects of various components of this invention, including but not limited to the drug core, indications of reduction in IOP, and treatment time periods, are often presented in a range or baseline threshold format throughout this patent document. The description in range or baseline threshold format is merely for convenience and brevity and should not be construed as an inflexible limitation on the scope of the invention. Accordingly, the description of a range or baseline threshold should be considered to have specifically disclosed all the possible subranges as well as individual numerical values within that range or above that baseline threshold. For example, description of a drug core having a drug or other agent concentration range of 3.5 micrograms to 135 micrograms should be considered to have specifically disclosed subranges, such as 5 micrograms to 134 micrograms, 6 micrograms to 135 micrograms, 40 micrograms to 100 micrograms, 44 micrograms to 46 micrograms, etc., as well as individuals numbers within that range, such as 41 micrograms, 42 micrograms, 43 micrograms, 44 micrograms, 45 micrograms, 46 micrograms, 47 micrograms, 48 micrograms, etc. This construction applies regardless of the breadth of the range or baseline threshold and in all contexts throughout this disclosure.

What is claimed is:

1. A method to reduce intraocular pressure in an eye of a patient having open angle glaucoma or ocular hypertension and a baseline intraocular pressure of 21-30 mmHg, the method comprising:
administering to the eye of the patient having open angle glaucoma or ocular hypertension and a baseline intraocular pressure of 21-30 mmHg, an intraocular pressure-reducing therapeutic agent sustained release topical formulation, wherein the sustained release topical formulation is capable of continuously releasing the intraocular pressure-reducing therapeutic agent over at least 7 days to the eye from a punctal implant wherein the intraocular pressure is reduced at least 10% from baseline, and
wherein the punctal implant comprises a first, second and intermediate portion, wherein the implant extends from a proximal end of the first portion, defining a proximal axis, to a distal end of the second portion, defining a distal axis, and when implanted, is configured with an at least 45 degree angled intersection between the proximal axis and the distal axis for biasing at least a portion of the implant against at least a portion of a lacrimal canaliculus located at or more distal to a canaliculus curvature and wherein the intermediate portion projects proximally from the intersection between the first and second implant body portions and is configured to bias against a portion of a lacrimal canaliculus ampulla.

2. The method of claim 1, wherein the intraocular pressure is reduced an amount selected from the group consisting of at least 15% from baseline, at least 20% from baseline, and at least 25% from baseline.

3. The method of claim 1, wherein the intraocular pressure-reducing therapeutic agent is released for a period of time selected from the group consisting of at least about 30 days, at least about 60 days, and at least about 90 days.

4. The method of claim 1, wherein the formulation is dispersed throughout a body of the punctal implant.

5. The method of claim 1, wherein the formulation is contained within a drug core disposed in the punctal implant, wherein the drug insert comprises a matrix and therapeutic agent.

6. The method of claim 1, wherein the punctal implant is inserted into one punctum of each of both eyes of the patient.

7. The method of claim 1, wherein the reduction in intraocular pressure is maintained for a continuous period of time selected from the group consisting of: up to about 14 days, up to about 21 days, up to about 28 days, up to about 56 days, up to about 84 days, and up to about 105 days.

8. A method to reduce intraocular pressure in an eye of a patient having open angle glaucoma or ocular hypertension and a baseline intraocular pressure of 21-30 mmHg, the method comprising:
inserting a punctal implant into at least one punctum of the eye of the patient having open angle glaucoma or ocular hypertension and a baseline intraocular pressure of 21-30 mmHg, wherein the implant comprises an intraocular pressure-reducing therapeutic agent sustained release topical formulation drug core comprising a matrix and the therapeutic agent, wherein the sustained release topical formulation is capable of continuously releasing the intraocular pressure-reducing therapeutic agent over at least 7 days to the eye wherein the intraocular pressure is reduced at least about 10% from baseline, and
wherein the punctal implant comprises a first, second and intermediate portion, wherein the implant extends from a proximal end of the first portion, defining a proximal axis, to a distal end of the second portion, defining a distal axis, and when implanted, is configured with an at least 45 degree angled intersection between the proximal axis and the distal axis for biasing at least a portion of the implant against at least a portion of a lacrimal canaliculus located at or more distal to a canaliculus curvature and wherein the intermediate portion projects proximally from the intersection between the first and second implant body portions and is configured to bias against a portion of a lacrimal canaliculus ampulla.

9. The method of claim 8, wherein the intraocular pressure is reduced by an amount selected from the group consisting of at least 15% from baseline, at least 20% from baseline and at least 25% from baseline.

10. The method of claim 8, wherein the intraocular pressure-reducing therapeutic agent is released for a period of time selected from the group consisting of at least about 30 days, at least about 60 days, and at least about 90 days.

11. The method of claim 8, wherein the punctal implant comprises a retention structure.

12. The method of claim 4, wherein the punctal implant is at least partially coated by an impermeable coating.

13. The method of claim 12, wherein the impermeable coating is parylene.

14. The method of claim 1, wherein the intraocular pressure-reducing therapeutic agent is an anti-glaucoma medication.

15. The method of claim 1, wherein the intraocular pressure-reducing therapeutic agent is bimatoprost, latanoprost, or travoprost.

16. The method of claim 8, wherein the intraocular pressure-reducing therapeutic agent is an anti-glaucoma medication.

17. The method of claim 8, wherein the intraocular pressure-reducing therapeutic agent is bimatoprost, latanoprost, or travoprost.

18. The method of claim 8, wherein the matrix of the drug core is selected from silicone, acrylate, polyethylene, polyurethane, hydrogel, polyester, polypropylene, polytetrafluoroethylene (PTFE), expanded PTFE (ePTFE), polyether ether ketone (PEEK), nylon, extruded collagen, polymer foam, silicone rubber, polyethylene terephthalate, ultra-high molecular weight polyethylene, polycarbonate urethane, polyimides, stainless steel, nickel-titanium alloy, titanium, stainless steel, or cobalt-chrome alloy.

\* \* \* \* \*